United States Patent
Zale et al.

(10) Patent No.: US 9,393,310 B2
(45) Date of Patent: *Jul. 19, 2016

(54) DRUG LOADED POLYMERIC NANOPARTICLES AND METHODS OF MAKING AND USING SAME

(75) Inventors: Stephen E. Zale, Hopkinton, MA (US); Greg Troiano, Pembroke, MA (US); Mir Mukkaram Ali, Woburn, MA (US); Jeff Hrkach, Lexington, MA (US); James Wright, Lexington, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,691

(22) Filed: May 23, 2012

(65) Prior Publication Data

US 2012/0276162 A1 Nov. 1, 2012

Related U.S. Application Data

(63) Continuation of application No. 12/485,399, filed on Jun. 16, 2009, now Pat. No. 8,206,747.

(60) Provisional application No. 61/061,704, filed on Jun. 16, 2008, provisional application No. 61/061,697, (Continued)

(51) Int. Cl.
*A61K 9/14* (2006.01)
*A61K 47/34* (2006.01)
(Continued)

(52) U.S. Cl.
CPC . *A61K 47/34* (2013.01); *A61J 3/00* (2013.01); *A61K 9/10* (2013.01); *A61K 9/14* (2013.01); *A61K 9/145* (2013.01); *A61K 9/146* (2013.01); *A61K 9/19* (2013.01); *A61K 9/5146* (2013.01); *A61K 9/5153* (2013.01); *A61K 31/337* (2013.01); *A61K 31/436* (2013.01); *A61K 31/437* (2013.01); *A61K 31/4355* (2013.01); *A61K 31/475* (2013.01); *A61K 31/704* (2013.01); *A61K 31/7068* (2013.01); *A61K 47/4883* (2013.01); *A61K 47/48869* (2013.01);
(Continued)

(58) Field of Classification Search
None
See application file for complete search history.

(56) References Cited

U.S. PATENT DOCUMENTS

| 5,302,401 A | 4/1994 | Liversidge et al. |
| 5,543,158 A * | 8/1996 | Gref et al. ............ 424/501 |

(Continued)

FOREIGN PATENT DOCUMENTS

| CN | 1957911 A | 5/2007 |
| CN | 1961864 A | 5/2007 |

(Continued)

OTHER PUBLICATIONS

M Tobio, R Gref, A Sanchez, R Langer, MJ Alonso. "Stealth PLA-PEG Nanoparticles as Protein Carriers for Nasal Administration." Pharmaceutical Research, vol. 15 No. 2, 1998, pp. 270-275.*
(Continued)

*Primary Examiner* — Isaac Shomer
(74) *Attorney, Agent, or Firm* — Goodwin Procter LLP

(57) ABSTRACT

The present disclosure generally relates to nanoparticles having about 0.2 to about 35 weight percent of a therapeutic agent; and about 10 to about 99 weight percent of biocompatible polymer such as a diblock poly(lactic) acid-poly(ethylene)glycol. Other aspects of the invention include methods of making such nanoparticles.

20 Claims, 30 Drawing Sheets

Related U.S. Application Data filed on Jun. 16, 2008, provisional application No. 61/061,760, filed on Jun. 16, 2008, provisional application No. 61/088,159, filed on Aug. 12, 2008, provisional application No. 61/105,916, filed on Oct. 16, 2008, provisional application No. 61/106,777, filed on Oct. 20, 2008, provisional application No. 61/169,514, filed on Apr. 15, 2009, provisional application No. 61/169,519, filed on Apr. 15, 2009, provisional application No. 61/169,541, filed on Apr. 15, 2009, provisional application No. 61/173,784, filed on Apr. 29, 2009, provisional application No. 61/173,790, filed on Apr. 29, 2009, provisional application No. 61/175,209, filed on May 4, 2009, provisional application No. 61/175,219, filed on May 4, 2009, provisional application No. 61/175,226, filed on May 4, 2009, provisional application No. 61/182,300, filed on May 29, 2009.

(51) Int. Cl.

| | |
|---|---|
| *A61K 9/10* | (2006.01) |
| *A61K 9/19* | (2006.01) |
| *A61K 9/51* | (2006.01) |
| *A61K 31/337* | (2006.01) |
| *A61K 31/436* | (2006.01) |
| *A61K 31/475* | (2006.01) |
| *A61K 47/48* | (2006.01) |
| *B82Y 5/00* | (2011.01) |
| *A61J 3/00* | (2006.01) |
| *A61K 31/4355* | (2006.01) |
| *A61K 31/437* | (2006.01) |
| *A61K 31/704* | (2006.01) |
| *A61K 31/7068* | (2006.01) |
| *A61K 9/16* | (2006.01) |
| *C07C 59/08* | (2006.01) |

(52) U.S. Cl.
CPC ............... *B82Y 5/00* (2013.01); *A61K 9/1647* (2013.01); *C07C 59/08* (2013.01); *Y10S 977/773* (2013.01)

(56) References Cited

U.S. PATENT DOCUMENTS

| | | | |
|---|---|---|---|
| 5,563,122 A | 10/1996 | Endo et al. | |
| 5,578,325 A | 11/1996 | Domb et al. | |
| 5,766,635 A | 6/1998 | Spenleuhauer et al. | |
| 6,007,845 A | 12/1999 | Domb et al. | |
| 6,136,808 A * | 10/2000 | Abe et al. | 514/253.11 |
| 6,136,846 A | 10/2000 | Rubinfeld et al. | |
| 6,139,870 A | 10/2000 | Verrecchia | |
| 6,194,006 B1 | 2/2001 | Lyons et al. | |
| 6,201,072 B1 | 3/2001 | Rathi et al. | |
| 6,254,890 B1 | 7/2001 | Hirosue et al. | |
| 6,265,609 B1 | 7/2001 | Jackson et al. | |
| 6,346,274 B1 | 2/2002 | Koll et al. | |
| 6,395,718 B1 | 5/2002 | Slusher et al. | |
| 6,528,499 B1 | 3/2003 | Kozikowski et al. | |
| 6,841,547 B2 | 1/2005 | Brown et al. | |
| 6,875,886 B2 | 4/2005 | Frangioni | |
| 6,890,946 B2 | 5/2005 | Nakshatri et al. | |
| 6,890,950 B2 | 5/2005 | Boothman et al. | |
| 6,899,898 B2 | 5/2005 | Albayrak | |
| 6,902,743 B1 | 6/2005 | Setterstrom et al. | |
| 6,916,788 B2 | 7/2005 | Seo et al. | |
| 7,422,902 B1 | 9/2008 | Wheeler et al. | |
| 7,687,071 B1 | 3/2010 | Heger et al. | |
| 8,003,128 B2 | 8/2011 | Kreuter et al. | |
| 8,034,765 B2 | 10/2011 | De et al. | |
| 8,206,747 B2 * | 6/2012 | Zale et al. | 424/489 |
| 8,211,473 B2 | 7/2012 | Troiano et al. | |
| 8,318,208 B1 * | 11/2012 | Zale et al. | 424/489 |
| 8,318,211 B2 * | 11/2012 | Zale et al. | 424/501 |
| 8,357,401 B2 | 1/2013 | Troiano et al. | |
| 8,518,963 B2 | 8/2013 | Ali et al. | |
| 8,563,041 B2 | 10/2013 | Grayson et al. | |
| 8,603,534 B2 * | 12/2013 | Zale et al. | 424/489 |
| 8,603,535 B2 | 12/2013 | Troiano et al. | |
| 8,609,142 B2 | 12/2013 | Troiano et al. | |
| 8,613,951 B2 * | 12/2013 | Zale et al. | 424/489 |
| 8,613,954 B2 * | 12/2013 | Zale et al. | 424/489 |
| 8,617,608 B2 * | 12/2013 | Zale et al. | 424/489 |
| 8,623,417 B1 * | 1/2014 | Zale et al. | 424/489 |
| 8,637,083 B2 | 1/2014 | Troiano et al. | |
| 2002/0045582 A1 | 4/2002 | Margolin et al. | |
| 2002/0119916 A1 | 8/2002 | Hassan | |
| 2003/0068377 A1 | 4/2003 | Fowers et al. | |
| 2003/0143184 A1 | 7/2003 | Seo et al. | |
| 2003/0232887 A1 | 12/2003 | Johnson et al. | |
| 2003/0235619 A1 | 12/2003 | Allen et al. | |
| 2004/0054190 A1 | 3/2004 | Pomper et al. | |
| 2004/0071768 A1 | 4/2004 | Sarris et al. | |
| 2004/0081688 A1 * | 4/2004 | Del Curto et al. | 424/450 |
| 2004/0086544 A1 | 5/2004 | Bezemer et al. | |
| 2004/0185170 A1 | 9/2004 | Chungi et al. | |
| 2004/0219224 A1 | 11/2004 | Yakovlevsky et al. | |
| 2004/0220081 A1 | 11/2004 | Kreitz et al. | |
| 2004/0247624 A1 | 12/2004 | Unger et al. | |
| 2004/0247680 A1 | 12/2004 | Farokhzad et al. | |
| 2005/0037075 A1 * | 2/2005 | Farokhzad et al. | 424/468 |
| 2005/0037086 A1 | 2/2005 | Tyo et al. | |
| 2005/0063976 A1 * | 3/2005 | Schultes et al. | 424/155.1 |
| 2005/0123617 A1 | 6/2005 | Chang et al. | |
| 2005/0136258 A1 | 6/2005 | Nie et al. | |
| 2005/0142205 A1 | 6/2005 | Rashba-Step et al. | |
| 2005/0201972 A1 | 9/2005 | Seo et al. | |
| 2005/0256071 A1 | 11/2005 | Davis | |
| 2005/0266067 A1 | 12/2005 | Sengupta et al. | |
| 2006/0002852 A1 | 1/2006 | Saltzman et al. | |
| 2006/0002971 A1 | 1/2006 | Saltzman et al. | |
| 2006/0034925 A1 | 2/2006 | Au et al. | |
| 2006/0057219 A1 | 3/2006 | Nagasaki et al. | |
| 2006/0094741 A1 * | 5/2006 | Lahav et al. | 514/44 |
| 2006/0110460 A1 | 5/2006 | Ferret et al. | |
| 2006/0165987 A1 | 7/2006 | Hildgen et al. | |
| 2007/0031402 A1 | 2/2007 | Zhang et al. | |
| 2007/0041901 A1 | 2/2007 | Diener et al. | |
| 2007/0043066 A1 | 2/2007 | Sum et al. | |
| 2007/0053845 A1 | 3/2007 | Sengupta et al. | |
| 2007/0154554 A1 | 7/2007 | Burgermeister et al. | |
| 2008/0057102 A1 | 3/2008 | Roorda | |
| 2008/0081074 A1 | 4/2008 | Gu et al. | |
| 2008/0124400 A1 | 5/2008 | Liggins et al. | |
| 2008/0193381 A1 | 8/2008 | Babich et al. | |
| 2008/0267876 A1 | 10/2008 | Benita et al. | |
| 2009/0022806 A1 | 1/2009 | Mousa et al. | |
| 2009/0053293 A1 | 2/2009 | Liang et al. | |
| 2009/0053315 A1 | 2/2009 | Brough et al. | |
| 2009/0061009 A1 | 3/2009 | Schwarz et al. | |
| 2009/0061010 A1 | 3/2009 | Zale et al. | |
| 2009/0074753 A1 | 3/2009 | Lynch | |
| 2009/0074828 A1 | 3/2009 | Alexis et al. | |
| 2009/0155349 A1 | 6/2009 | Heller et al. | |
| 2009/0170753 A1 | 7/2009 | Welz et al. | |
| 2009/0196933 A1 | 8/2009 | De et al. | |
| 2009/0306120 A1 | 12/2009 | Lim et al. | |
| 2009/0317479 A1 | 12/2009 | Ishihara et al. | |
| 2010/0008998 A1 | 1/2010 | Kang et al. | |
| 2010/0015050 A1 | 1/2010 | Panyam et al. | |
| 2010/0040537 A1 | 2/2010 | Gu et al. | |
| 2010/0068285 A1 | 3/2010 | Zale et al. | |
| 2010/0068286 A1 | 3/2010 | Troiano et al. | |
| 2010/0069426 A1 | 3/2010 | Zale et al. | |
| 2010/0087337 A1 | 4/2010 | Dewitt | |
| 2010/0104645 A1 | 4/2010 | Ali et al. | |
| 2010/0104655 A1 | 4/2010 | Zale et al. | |
| 2010/0166866 A1 | 7/2010 | Fischer et al. | |
| 2010/0216804 A1 | 8/2010 | Zale et al. | |
| 2010/0226986 A1 | 9/2010 | Grayson et al. | |

(56) References Cited

U.S. PATENT DOCUMENTS

| | | |
|---|---|---|
| 2010/0266491 A1 | 10/2010 | Farokhzad et al. |
| 2010/0303723 A1 | 12/2010 | Farokhzad et al. |
| 2010/0303900 A1 | 12/2010 | Ramstack et al. |
| 2010/0316725 A1 | 12/2010 | Ryde et al. |
| 2011/0159079 A1 | 6/2011 | Li et al. |
| 2011/0217377 A1 | 9/2011 | Zale et al. |
| 2011/0224288 A1 | 9/2011 | Zale et al. |
| 2011/0274759 A1 | 11/2011 | Troiano et al. |
| 2011/0275704 A1 | 11/2011 | Troiano et al. |
| 2011/0294717 A1 | 12/2011 | Ali et al. |
| 2012/0004293 A1 | 1/2012 | Zale et al. |
| 2012/0027820 A1 | 2/2012 | Troiano et al. |
| 2012/0140790 A1 | 6/2012 | Ali et al. |
| 2013/0034608 A1 | 2/2013 | Zale et al. |
| 2013/0101672 A1 | 4/2013 | Cheng et al. |
| 2013/0108668 A1 | 5/2013 | Figueiredo et al. |
| 2013/0115293 A1 | 5/2013 | Sabnis et al. |
| 2013/0172406 A1 | 7/2013 | Zale et al. |
| 2013/0189315 A1 | 7/2013 | Zale et al. |
| 2013/0230568 A1 | 9/2013 | Troiano et al. |
| 2013/0236500 A1 | 9/2013 | Zale et al. |
| 2013/0243827 A1 | 9/2013 | Troiano et al. |
| 2013/0243863 A1 | 9/2013 | Troiano et al. |
| 2013/0302433 A1 | 11/2013 | Troiano et al. |
| 2014/0030351 A1 | 1/2014 | Zale et al. |
| 2014/0093579 A1 | 4/2014 | Zale et al. |
| 2014/0142165 A1 | 5/2014 | Grayson et al. |
| 2014/0178475 A1 | 6/2014 | Figueiredo et al. |
| 2014/0186452 A1 | 7/2014 | Figueiredo et al. |
| 2014/0186453 A1 | 7/2014 | Zale et al. |
| 2014/0248358 A1 | 9/2014 | Figueiredo et al. |
| 2014/0249158 A1 | 9/2014 | Figueiredo et al. |
| 2014/0308363 A1 | 10/2014 | Zale |
| 2014/0356444 A1 | 12/2014 | Troiano et al. |
| 2015/0017245 A1 | 1/2015 | Zale et al. |

FOREIGN PATENT DOCUMENTS

| | | |
|---|---|---|
| CN | 1969816 A | 5/2007 |
| CN | 1969818 A | 5/2007 |
| CN | 101053553 A | 10/2007 |
| CN | 101396340 A | 4/2009 |
| CN | 101396342 A | 4/2009 |
| CN | 101433520 A | 5/2009 |
| EA | 011594 | 12/2007 |
| EP | 0805678 A1 | 11/1997 |
| EP | 1985309 A1 | 10/2008 |
| EP | 2106806 A1 | 10/2009 |
| JP | H10-194995 A | 7/1998 |
| JP | 2006131577 A | 5/2006 |
| JP | 2006321763 A | 11/2006 |
| KR | 10-0418916 | 3/2002 |
| KR | 20020041712 A | 6/2002 |
| RU | 2007140909 A | 5/2009 |
| WO | WO-8900846 A1 | 2/1989 |
| WO | WO-9428874 A1 | 12/1994 |
| WO | WO-9503357 A1 | 2/1995 |
| WO | WO-9535097 A1 | 12/1995 |
| WO | WO-9741837 A2 | 11/1997 |
| WO | WO-00/00222 | 1/2000 |
| WO | WO-0019996 A1 | 4/2000 |
| WO | WO-0187345 A1 | 11/2001 |
| WO | WO-0245689 A1 | 6/2002 |
| WO | WO-02080846 A2 | 10/2002 |
| WO | WO-02098885 A1 | 12/2002 |
| WO | WO-03017987 A1 | 3/2003 |
| WO | WO-03032906 A2 | 4/2003 |
| WO | WO-03/055469 A1 | 7/2003 |
| WO | WO-03/086369 A2 | 10/2003 |
| WO | WO-2004060059 A2 | 7/2004 |
| WO | WO-2004/084871 A1 | 10/2004 |
| WO | WO-2004089291 A2 | 10/2004 |
| WO | WO-2005009357 A2 | 2/2005 |
| WO | WO-2005020989 A1 | 3/2005 |
| WO | WO-2005/046572 A2 | 5/2005 |
| WO | WO-2006/093991 A1 | 9/2006 |
| WO | WO-2007/024323 A2 | 3/2007 |
| WO | WO-2007/028341 A1 | 3/2007 |
| WO | WO-2007/034479 A2 | 3/2007 |
| WO | WO-2007/074604 A1 | 7/2007 |
| WO | WO-2007/110152 A2 | 10/2007 |
| WO | WO-2007/133807 A2 | 11/2007 |
| WO | WO-2008/019142 A2 | 2/2008 |
| WO | WO-2008016602 A2 | 2/2008 |
| WO | WO-2008/058192 A2 | 5/2008 |
| WO | WO-2008051245 A2 | 5/2008 |
| WO | WO-2008/105773 A2 | 9/2008 |
| WO | WO-2008109163 A1 | 9/2008 |
| WO | WO-2008/121949 A1 | 10/2008 |
| WO | WO-2008/124632 A1 | 10/2008 |
| WO | WO-2008/124634 A1 | 10/2008 |
| WO | WO-2008/124639 A2 | 10/2008 |
| WO | WO-2008/139804 A1 | 11/2008 |
| WO | WO-2009/070302 A1 | 6/2009 |
| WO | WO-2009074274 A1 | 6/2009 |
| WO | WO-2009/084801 A1 | 7/2009 |
| WO | WO-2009121631 | 10/2009 |
| WO | WO-2010/005721 A2 | 1/2010 |
| WO | WO-2010/005723 A2 | 1/2010 |
| WO | WO-2010/005725 A2 | 1/2010 |
| WO | WO-2010/005726 A2 | 1/2010 |
| WO | WO-2010/068866 A2 | 6/2010 |
| WO | WO-2010/075072 A2 | 7/2010 |
| WO | WO-2010/114768 A1 | 10/2010 |
| WO | WO-2010/114770 A1 | 10/2010 |
| WO | WO-2010117668 A1 | 10/2010 |
| WO | WO-2011/072218 A2 | 6/2011 |
| WO | WO-2011079279 A2 | 6/2011 |
| WO | WO-2011/084513 A2 | 7/2011 |
| WO | WO-2011/084518 A2 | 7/2011 |
| WO | WO-2011/084521 A2 | 7/2011 |
| WO | WO-2011/119995 A2 | 9/2011 |
| WO | WO-2012040513 A1 | 3/2012 |
| WO | WO-2012/054923 A2 | 4/2012 |
| WO | WO-2012166923 A2 | 12/2012 |
| WO | WO-2013044219 A1 | 3/2013 |
| WO | WO-2013127490 A1 | 9/2013 |
| WO | WO-2014043618 A1 | 3/2014 |
| WO | WO-2014043625 A1 | 3/2014 |
| WO | WO-2014210485 A1 | 12/2014 |

OTHER PUBLICATIONS

CR Heald, S Stolnik, KS Kujawinski, CD Matteis, MC Garnett, L Illum, SS Davis, SS Purkiss, RJ Barlow, PR Gellert. "Poly(lactic acid)-Poly(ethylene oxide) (PLA-PEG) Nanoparticles: NMR Studies of the Central Solidlike PLA Core and the Liquid PEG Corona." Langmuir, vol. 18, 2002, pp. 3669-3675.*

F De Jaeghere, E Allemann, J Feijen, T Kissel, E Doelker, R Gurny. "Freeze-Drying and Lyopreservation of Diblock and Triblock Poly(Lactic Acid)-Poly(Ethylene Oxide) (PLA-PEO) Copolymer Nanoparticles." Pharmaceutical Development and Technology, vol. 5(4), 2000, pp. 473-483.*

S Murugesan, S Ganesan, RK Averineni, M Nahar, P Mishra, NK Jain. "PEGylated Poly(Lactide-co-Glycolide) (PLGA) Nanoparticulate Delivery of Docetaxel: Synthesis of Diblock Copolymers, Optimization of Preparation Variables on Formulation Characteristics and In Vitro Release Studies." Journal of Biomedical Nanotechnology, vol. 3, 2007, pp. 52-60.*

Adams, Monica et al, "Amphiphilic Block Copolymers for Drug Delivery" *J. Pharm. Sci.* (2003) 92, 1343-1355.

Barinka et al., "Interactions Between Human Glutamate Carboxypeptidase II and Urea-Based Inhibitors: Structural Characterization," *J. Med. Chem.* (2008) 51:7737-7743.

Barinka et al., "Structural Insight into the Pharmacophore Pocket of Human Glutamate Carboxypeptidase II," *J. Med. Chem.* (2007) 50:3267-3273.

Bilati et al., "Nanoprecipitation Versus Emulsion-based Techniques for the Encapsulation of Proteins into Biodegradable Nanoparticles and Process-related Stability Issues," AAPS *PharmSciTech.* (2005) 6(4):E594-E604.

(56) References Cited

OTHER PUBLICATIONS

Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells," *J. Amer. Coll. Cardiol.* (2006) 47(9):1786-1795.
Caliceti, P., et al., "Effective Protein Release from PEG/PLA Nanoparticles Produced by Compressed Gas Anti-Solvent Precipitation Techniques," Journal of Controlled Release, 2004, vol. 94, pp. 195-205.
Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.
Chen et al., "Radiohalogenated Prostate-Specific Membrane Antigen (PSMA)-Based Ureas as Imaging Agents for Prostate Cancer," *J. Med. Chem.* (2008) 51(24):7933-7943.
Cheng et al., "Formulation of Functionalized PLGA-PEG Nanoparticles for in Vivo Targeted Drug Delivery," *Biomaterials* (2007) 28:869-879.
Dancey et al., "Therapeutic Targets" mTOR and Related Pathways, *Cancer Biol. Ther.* (2006) 5:9: 1065-1073.
Davaran, "Preparation and in Vitro Evaluation of Linear and Star-Branched PLGA Nanoparticles for Insulin Delivery," *J. Bioact. Compat. Polvm.* (2008) 23:115-131.
De Jaeghere et al., "Formulation and Lyoprotection of Poly(lactic acid-co-ethylene oxide) Nanoparticles: Influence on Physical Stability and in Vitro Cell Uptake," *Pharm. Res.* (1999) 16(6):859-866.
De Jaeghere, F. et al., "Freeze-Drying and Lyopreservation of Diblock and Triblock Poly(Lactic Acid)-Poly(Ethylene Oxide) (PLA-PEO) Copolymer Nanoparticles," Pharmaceutical Development and Technology, vol. 5(4), 2000, pp. 473-483.
Eurasian Search Report for Application No. EA 201170038, dated Jul. 8, 2011.
Eurasian Search Report for Application No. EA 201170039, dated Nov. 21, 2011.
Ewesuedo et al., "Chapter 1: Systemically Administered Drugs." *Drug Delivery Systems in Cancer Therapy.* Ed. D.M. Brown. Totowa:Humana, 2003, pp. 3-14.
Extended European Search Report for Application No. EP 09794913.5 mailed Jul. 8, 2011.
Extended European Search Report for Application No. EP 09794915.0, mailed Jan. 25, 2012.
Extended European Search Report for Application No. EP 09835578.7, mailed May 18, 2012.
Farokhzad et al., "Nanoparticle-Aptamer Bioconjugates: A New Approach for Targeting Prostate Cancer Cells," *Cancer Res.* (Nov. 1, 2004) 64:7668-7672.
Farokhzad et al., "Targeted Nanoparticle-Aptamer Bioconjugates for Cancer Chemotherapy In Vivo," *Proc. Natl. Acad. Sci. USA* (2006) 103,16:6315-6320.
Foss et al., "Radiolabeled Small-Molecule Ligands for Prostate-Specific Membrane Antigen: In Vivo Imaging in Experimental Models of Prostate Cancer," *Clin. Cancer Res.* (2005)11(11):4022-4028.
Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005.).
Gao et al., "In Vivo Cancer Targeting and Imaging with Semiconductor Quantum Dots," *Nat. Biotechnol.,* (2004) 22, 8: 969-976.
Govender et al., "Defining the Drug Incorporation Properties of PLA-PEG Nanoparticles," *Int. J. Pharm.* (2000) 199:95-110.
Gref et al., "Biodegradable Long-Circulating Polymeric Nanospheres," *Science* (1994) 263:1600-1603.
Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm.* (2001) 51:111-118.
Gu, F. et al. "Precise Engineering of Targeted Nanoparticles by Using Self-Assembled Biointegrated Block Copolymers", *Proc. Natl. Acad. Sci. USA.* (2008) 105, 2586-2591.
Heald et al., "Poly(lactic acid)-Poly(ethylene oxide) (PLA-PEG) Nanoparticles: NMR Studies of the Central Solidlike PLA Core and the Liquid PEG Corona," *Langmuir* (2002) 18:3669-3675.
Hederstrom et al., "Purification and Surface Modification of Polymeric Nanoparticles for Medical Applications" Master's Thesis. SINTEF Materials and Chemistry, Trondheim, Norway, Mar. 3, 2008.
Heldman, Alan et al., "Paclitaxel stent coating inhibits neointimal hyperplasia at 4 weeks in a porcine model of coronary restenosis," Circulation, 103, pp. 2289-2295 (2001).
Hrkach et al., "Preclinical Development and Clinical Translation of a PSMA-Targeted Docetaxel Nanoparticle with a Differentiated Pharmacological Profile " *Sci. Trans. Med.* (2012) 4:1-11.
Humblet et al., "An HPLC/Mass Spectrometry Platform for the Development of Multimodality Contrast Agents and Targeted Therapeutics: Prostate-Specific Membrane Antigen Small Molecule Derivatives, " *Contrast Med. Mol. Imaging* (2006) 1:196-211.
Humblet et al., "High-Affinity Near-Infrared Fluorescent Small-Molecule Contrast Agents for In Vivo Imaging of Prostate-Specific Membrane Antigen," *Mol. Imaging* ( 2005) 4:448-462.
International Search Report for Application No. PCT/US08/13158 dated Jan. 20, 2009 and mailed Feb. 17, 2009.
International Search Report for Application No. PCT/US08/58873 dated Aug. 15, 2008 and mailed Aug. 28, 2008.
International Search Report for Application No. PCT/US09/47513 dated Jan. 18, 2010 and mailed Jan. 18, 2010.
International Search Report for Application No. PCT/US09/67672 dated Aug. 20, 2010 and mailed Aug. 23, 2010.
International Search Report for Application No. PCT/US09/68028 dated Aug. 9, 2010 and mailed Aug. 23, 2010.
International Search Report for Application No. PCT/US10/59879 dated Aug. 30, 2011 and mailed Aug. 30, 2011.
International Search Report for Application No. PCT/US10/60564 dated Sep. 29, 2011 and mailed Sep. 29, 2011.
International Search Report for Application No. PCT/US10/60570 dated Aug. 25, 2011 and mailed Aug. 25, 2011.
International Search Report for Application No. PCT/US10/60575 dated Aug. 25, 2011 and mailed Aug. 25, 2011.
International Search Report for Application No. PCT/US11/057498 dated May 9, 2012 and mailed May 10, 2012.
International Search Report for PCT/US09/47515 dated Jan. 18, 2010 and mailed Jan. 19, 2010.
International Search Report for PCT/US09/47517 dated Feb. 25, 2010 and mailed Mar. 2, 2010.
International Search Report for PCT/US09/47518 dated Mar. 5, 2010 and mailed Mar. 5, 2010.
Jayaprakash, Sarva, et al., "Design and Synthesis of a PSMA Inhibitor-Doxorubicin Conjugate for Targeted Prostrate Cancer Therapy," ChemMedChem 2006, 1, pp. 299-302.
Jiang et al., "Preparation of PLA and PLGA Nanoparticles by Binary Organic Solvent Diffusion Method," *J. Cent. South Univ. Technol.,* (2003) 10, 3:202-206.
Koziara, et al. "Blood Compatibility of Cetyl Alcohol/Polysorbate-Based Nanoparticles," *Pharma. Res.* (2005) 22(11):1821-1828.
Kozikowski et al., Design of Remarkably Simple, Yet Potent Urea-Based Inhibitors of Glutamate Carboxypeptidase II (NAALADase), *J. Med. Chem.* (2001) 44:298-301.
Kozikowski et al., "Synthesis of Urea-Based Inhibitors as Active Site Probes of Glutamate Carboxypeptidase II: Efficacy as Analgesic Agents," *J. Med. Chem.* (2004) 47:1729-1738.
Kwon, "Long Acting Porous Microparticle for Pulmonary Protein Delivery," *Int. J. Pharm.* (2007) 333:5-9.
Maresca, K.P., et al., "A Series of Halogenated Heterodimeric Inhibitors of Prostate Specific Membrane Antigen (PSMA) as Radiolabeled Probes for Targeting Prostate Cancer," J. Med. Chem. (2009) 52(2): 347-57.
Mease et al., "N-[N-[(S)-1,3-Dicarboxypropyl] Carbamoyl]-4-[$^{18}$F] Fluorobenzyl-L-Cysteine, [$^{18}$F] DCFBC: A New Imaging Probe for Prostate Cancer," *Clin. Cancer Res.* (2008) 14, 10:3036-3043.
Misra et al., "Production of Multimeric Prostate-Specific Membrane Antigen Small-Molecule Radiotracers Using a Solid-Phase $^{99m}$Tc Preloading Strategy," *J. Nuclear Med.* (2007) 48, 8:379-1389.

(56) References Cited

OTHER PUBLICATIONS

Murugesan et al., Pegylated Poly(lactide-co-glycolidel (PLGA) Nanoparticulate Delivery of Docetaxel: Synthesis of Diblock Copolymers, Optimization of Preparation Variables on Formulation Characteristics and in Vitro Release Studies. *J. Biomed. Nanotechnol.* (2007) 3:52-60.
Musumeci et al., "Lyoprotected Nanosphere Formulations for Paclitaxel Controlled Delivery." *J. Nanosci. Nanotech.* (2006) 6:3118-3125.
Ojer, "Spray-Drying of Poly(anhydride) Nanoparticles for Drug/Antigen Delivery," *J. Drug Del. Sci. Tech.* (2010) 20(5):353-359.
Oliver et al., "Conformational and SAR Analysis of NAALADase and PSMA Inhibitors," *Biorg. Med. Chem.* (2003) 11:4455-4461.
Olivier, "Drug Transport to Brain with Targeted Nanoparticles," *The Journal of the American Society for Experimental NeuroTherapeutics*, (2005) 2:108-119.
Omelczuk et al., "The Influence of Polymer Glass Transition Temperature and Molecular Weight on Drug Release from Tablets Containing Poly(DL-lactic acid)." *Pharm. Res.* (1992) 9(1):26-32.
Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.
Pourcelle, "PCL-PEG-based Nanoparticles Grafted with GRGDS Peptide: Preparation and Surface Analysis by XPS," *Biomacromolecules* (2007) 8:3977-3983.
Pulkkinen, M et al. "Three-Step Tumor Targeting of Paclitaxel Using Biotinylated PLA-PEG Nanoparticles and Avidin-Biotin Technology: Formulation Development and In Vitro Anticancer Activity", *Eur. J. Pharm. Biopharm.* (2008) 70, 66-74.
Riley et al. "Colloidal Stability and Drug Incorporation Aspects of Micellar-like PLA-PEG Nanoparticles," *Colloids Surf. B: Biointer.* (1999) 16:147-59.
Sapra et al., "Ligand-Targeted Liposomal Anticancer Drugs," *Prog. Lipid Res.* (2003) 42:439-462.
Sweetman, "Martindale: The Complete Drug Reference," 33rd ed., 2002, Pharmaceutical Press, entry for Docetaxel, p. 534.
Tamilvanan et al., "Manufacturing Techniques and Excipients Used During the Design of Biodegradable Polymer-Based Microspheres Containing Therapeutic Peptide/Protein for Parenteral Controlled Drug Delivery " *J. Pharm. Sci. Tech.* (2008) 62(2):125-154.
Tang, Hailun, et al., "Prostate Targeting Ligands Based on N-Acetylated α-Linked Acidic Dipeptidase," Biochem. Biophys. Res. Comm. 307 (2003), pp. 8-14.
Tobio, M. et al., "Stealth PLA-PEG Nanoparticles as Protein Carriers for Nasal Administration," *Pharm. Res.* (1998) 15, 2:270-275.
Vicari et al., "Paclitaxel Loading in PLGA Nanospheres Affected the in Vitro Drug Cell Accumulation and Antiproliferative Activity," *BMC Cancer* (2008) 8:212.
Yamamoto, Y., et al., "Long-Circulating Poly(ethylene glycol)-poly(D,L-lactide) block copolymer micelles with Modulated Surface Charge," Journal of Controlled Release, 2001, vol. 77, pp. 27-38.
Zhang et al., "Neointimal Hyperplasia Persists at Six Months after Siroli Mus-Eluting Stent Implantation in Diabetic Porcine," *Cardiovasc. Diabetol.* (2007) 6, 16:1-7.
Zhou, Jia, et al., "NAAG Peptidase Inhibitors and Their Potential for Diagnosis and Therapy," Nature Reviews/Drug Discovery, vol. 4, Dec. 2005, pp. 1015-1026.
Abdelwahed et al., "Freeze-Drying of Nanoparticles: Formulation, Process and Storage Considerations," *Adv. Drug Deliv. Rev.* (2006) 58:1688-1713.
Abizaid et al., "Sirolimus-Eluting Stents Inhibits Neointimal Hyperplasia in Diabetic Patients," Eur. Heart J., (2006) 25:104-112.
Extended European Search Report for Application No. EP 11186037.5, mailed Mar. 2, 2012.
Fournier et al., "Experimental Studies and Preliminary Clinical Trial of Vinorelbine-loaded Polymeric Bioresorbable Implants for the Local Treatment of Solid Tumors," *Can. Res.* (1991) 51: 5384-5391.

Lyseng-Williamson et al., "Docetaxel A Review of its Use in Metastatic Breast Cancer" *Drugs*. (2005) 65(17):2513-16.
Musumeci et al., "PLA/PLGA Nanoparticles for Sustained Release of Docetaxel," Int. J. Pharm. (2006) 325:172-179.
Senthilkumar et al., "Long Circulating PEGylated Poly(D,L-lactide-co-glycolide) Nanoparticulate Delivery of Docetaxel to Solid Tumors," *J. Drug Target.* (2008) 424-435.
Gill et al., "Modulated Differential Scanning Calorimetry," *J. Thermal Analysis.* (1993) 40:931-939.
Peracchia et al., "PEG-coated nanospheres from amphiphilic diblock and multiblock copolymers: Investigation of their drug encapsulation and release characteristics," *J. of Controlled Release.* (1996) 46:223-231.
Galsky et al., "Cabazitaxel," *Nature Reviews.* (2010) 9:677-678.
International Search Report for Application No. PCT/US2012/040215 dated Nov. 16, 2012 and mailed Nov. 16, 2012.
Gref et al., "'Stealth' Corona-Core Nanoparticles Surface Modified by Polyethylene Glycol (PEG): Influences of the Corona (PEG Chaing Length and Surface Density) and of the Core Composition on Phagocytic Uptake and Plasma Protein Adsorption," *Colloids and Surfaces B: Biointerfaces.* (2000) 301-313.
Extended European Search Report for EP 09794913.5 mailed Jul. 4, 2013, 9 pages.
Extended European Search Report for EP 10842556.2 mailed Jul. 8, 2013, 9 pages.
Extended European Search Report for EP 10842554.7 mailed Jul. 10, 2013, 9 pages.
Matsumoto et al., "Preparation of Nanoparticles consisted of poly(L-lactide)-poly(ethylene glycol)poly(L-lactide) and Their Evaluation In Vitro," *International J. of Pharmaceutics.* (1999) 185:93-101.
Extended European Search Report for EP 09794917.6 mailed Aug. 7, 2013, 8 pages.
Verrecchia et al., "Non-Stealth (poly(lactic acid/albumin) ) and stealth (poly(lactic acid-polyethylene glycol) ) nanoparticles as injectable drug carriers," *J. of Controlled Release.* (1995) 36:49-61.
Extended European Search Report for EP 10842557.0 mailed Jul. 8, 2013, 11 pages.
Altmann (Epothilone B and its analogs—a new family of anticancer agents, *Mini Rev Med Chem.* (2003) 3(2):149-158; Abstract Only [retrieved from Bentham Science, < URL: http://www.eurekaselect.com/80911/artcile>], 1 page.
Altmann (Epothilone B and its analogs—a new family of anticancer agents, *Mini Rev Med Chem.* (2003) 3(2):149-158; Abstract Only [retrieved from PUBMED, < URL: http://www.ncbi.nlm.nih.gov/pubmed/12570848>]), 1 page.
Avgoustakis, "Pegylated poly(lactide) and poly(lactide-co-glycolide) nanoparticles: Preparation, properties and possible applications in drug delivery," Current Drug Delivery. (2004) 1(4):321-333.
"Docetaxel Dosage," [retrieved on Mar. 28, 2013] http://www.drugs.com/dosage/docetaxel.html.
Extended European Search Report for Application No. EP 10836748.3, mailed Mar. 21, 2013.
Feng et al., "Nanoparticles of Biodegradable Polymers for Clinical Administration of Paclitaxel," *Current Medicinal Chemistry.* (2004) 11:413-424.
International Preliminary Report on Patentability for PCT/US2010/060575 dated Jun. 19, 2012, 11 pages.
International Search Report for Application No. PCT/US2012/056891 dated Jan. 4, 2013 and mailed Jan. 4, 2013.
Jeong et al., "Effect of cryoprotectants on the reconstitution of surfactant-free nanoparticles of poly(DL-lactide-co-glycolide)," *J. of Microencapsulation.* (2005) 22(6):593-601.
Majer et al., "Synthesis and Biological Evaluation of Thiol-Based Inhibitors of Glutamate Carboxypeptidase II: Discovery of an Orally Active GCP II Inhibitor," *J. Med. Chem.* (2003).46:1989-1996.
Merck (Betamethasone, Merck Index (Knovel, copyright 2006, 2012)), 3 pages.
"Taxotere Dosage," [retrieved on Mar. 28, 2013]. http://www.drugs.com/dosage/taxotere.html.
Allémann et al., "In vitro extended-release properties of drug-loaded poly(DL-Lactic Acid) nanoparticles produced by a salting-out procedure," *Pharmaceutical Research.* (1993) 10(12):1732-1737.

(56) References Cited

OTHER PUBLICATIONS

Allémann et al., "Preparation of aqueous polymeric nanodispersions by a reversible salting-out process: influence of process parameters on particle size," *Int. J. of Pharmaceutics.* (1992) 87:247-253.
Cayman Chemical, "Risperidone—Product Information" (https://www.caymanchem/pdfs/13629.pdf), 1 page, [Mar. 13, 2013].
Clinical Trials, "A Study of BIND-014 Given to Patients with Advanced or Mestastatic Cancer," [retrieved on May 9, 2014] Retrived from the internet <URL: http://clinicaltrials.gov/archive/NCT01300533/2013_04_30>, 4 pages.
Drug Bank (Canadian Institutes of Drug Research, Budesonide (DB01222) (2013) [Retrieved from internet <URL:http://www.drugbank.ca/drugs/DB01222 >], 9 pages.
International Search Report and Written Opinion for Application No. PCT/US2014/044617, dated Oct. 3, 2014 and mailed Oct. 3, 2014, 13 pages.
Notice of opposition for European Patent No. 2309990 dated Oct. 15, 2014, 5 pages.
Opposition Statement for European Patent No. 2309990 dated Oct. 15, 2014, 19 pages.
Song et al., "The effect of type of organic phase solvents on the particle size of poly(D,L-lactide-co-glycolide) nanoparticles," *Colloids and Surfaces A: Physicochem. Eng. Aspects.* (2006) 276:162-167.
International Search Report for Application No. PCT/US2013/059936, dated Feb. 4, 2014 and mailed Feb. 4, 2014, 8 pages.
Extended European Search Report for EP 11835279.8 mailed Feb. 28, 2014, 8 pages.
Dong et al., "(Methoxy poly(ethylene glycol)-poly(lactide) (MPEG-PLA) nanoparticles for controlled delivery of anticancer drugs," (2004) *Biomaterials.* 25:2843-2849.
Dorati et al., "Polyethylenglycol-co-poly-D,L-lactide copolymer based microspheres: preparation, characterization and delivery of a model protein," *J Microencapsul.* (2008) 25(5):330-338.
Extended European Search Report for EP 14150948.9 mailed Jul. 8, 2014, 8 pages.
Farokhzad et al., "Nanoparticle-aptamer bioconjugates for cancer targeting," *Expert Opin Drug Deliv.* (2006) 3(3):311-24.
Govender et al., "PLGA nanoparticles prepared by nanoprecipitation: drug loading and release studies of a water soluble drug," *J Control Release.* (1999) 57(2):171-85.
Gross, "Oral pH-modified release budesonide for treatment of inflammatory bowel disease, collagenous and lymphocytic colitis," *Expert Opin Pharmacother.* (2008) 9(7):1257-1265.
Jenning et al., "Characterisation of a novel solid lipid nanoparticle carrier system based on binary mixtures of liquid and solid lipids," *Int J Pharm.* (2000) 199(2):167-77.
Okassa et al., "Optimization of iron oxide nanoparticles encapsulation within poly(d,l-lactide-co-glycolide) sub-micron particles," *Eur J Pharm Biopharm.* (2007) 67(1):31-8.
Ren et al., "Preparation and characterization of magnetic PLA-PEG composite nanoparticles for drug targeting," *Reactive & Functional Polymers.* (2006) 66:944-951.
Stolnik et al., "(Polylactide-poly(ethylene glycol) micellar-like particles as potential drug carriers: production, colloidal properties and biological performance," (2001) *Journal Drug Targeting.* 9:361-378.
van Vlerken and Amiji, "Multi-functional polymeric nanoparticles for tumour-targeted drug delivery," *Expert Opin Drug Deliv.* (2006) 3(2):205-16.
Yoo et al., "Protein-fatty acid complex for enhanced loading and stability within biodegradable nanoparticles," *J Pharm Sci.* (2001) 90(2):194-201.
Dong et al., "In vitro and in vivo evaluation of methoxy polyethylene glycol-polylactide (MPEG-PLA) nanoparticles for small-molecule drug chemotherapy," (2007) *Biomaterials.* 28:4154-4160.
Eurasian Official Action for EA 201170038, dated Aug. 12, 2013.
Eurasian Official Action for EA 201170040, dated Jun. 29, 2012.
Eurasian Search Report for Application No. EA 201100765, dated Aug. 2, 2013.
Eurasian Search Report for Application No. EA 201290497, dated Jan. 15, 2013.
European Examination Report for EP 09794913.5, dated Jul. 16, 2012.
Extended European Search Report for EP 13162786.1 mailed Aug. 30, 2013, 7 pages.
Extended European Search Report for EP 13162789.5 mailed Aug. 30, 2013, 7 pages.
International Search Report for Application No. PCT/US2013/059949, dated Jan. 2, 2014 and mailed Jan. 2, 2014, 5 pages.
Kimura et al., "Local Delivery of Imatinib Mesylate (STI571)-Incorporated Nanoparticle Ex Vivo Suppresses Vein Graft Neointima Formation," *Cancer Res.* (2008) 118:S65-S70.
Li et al. "Post-Operative Imatinib in Patients with Intermediate or High Risk Gastrointestinal Stromal Tumor," *EJSO* (2011) 37:319-324.

\* cited by examiner

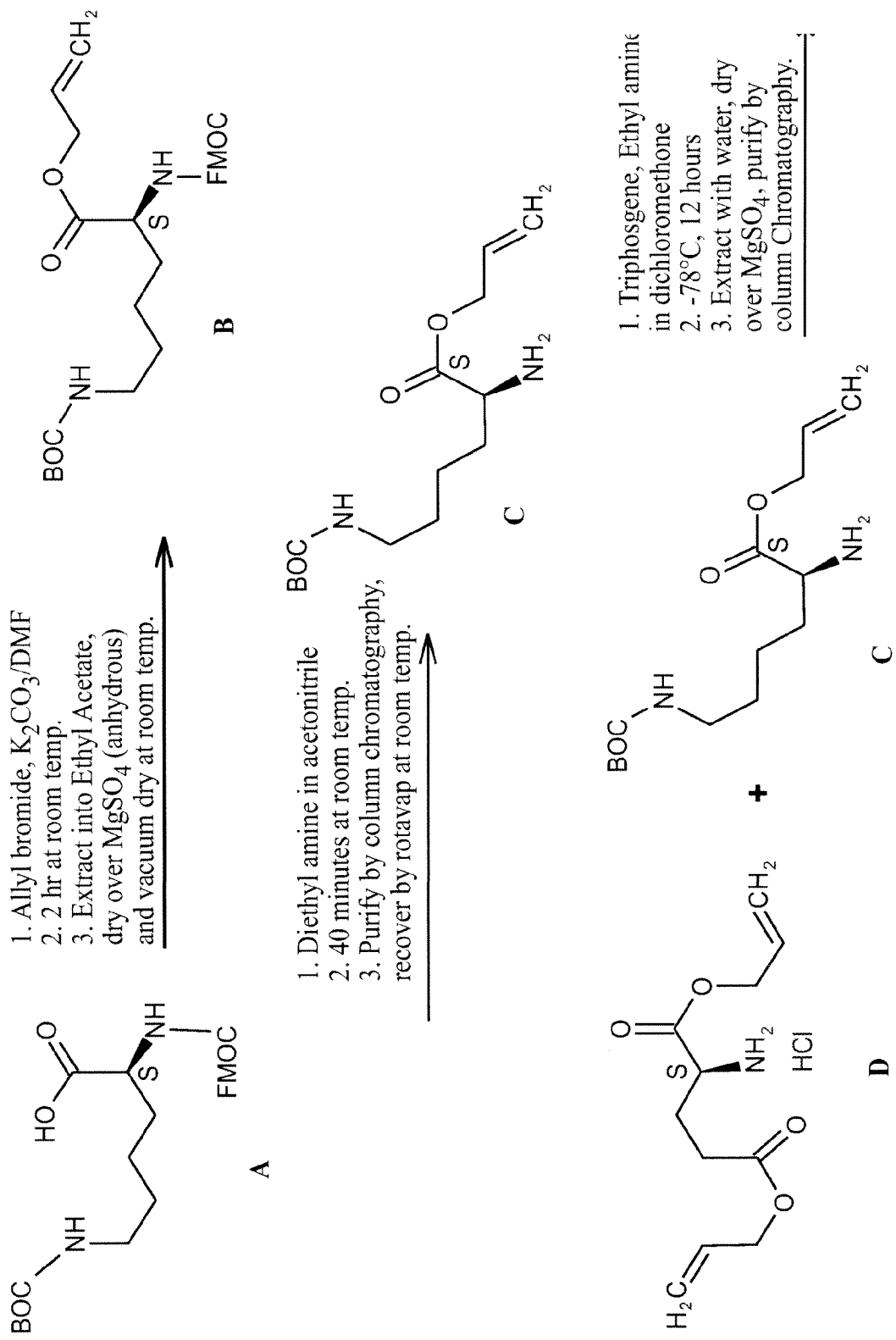

1. α-Hydroxy-ω-carboxypentyl poly(ethylene glycol), Ethyl dimethylaminopropylcarbodiimide (EDC), N-hydroxysuccimide (NHS), Diisopropyl ethyl amine (DIEA)Trifluoroacetic Acid (TFA) in Anhdydrous $CH_2Cl_2$
2. 4 hr at room temp.
3. Aqueous dialysis, centrifugal filtration, lyophilization 1. Lactide, Glycolide, Tin (II) 2-Ethyl hexanoate; 16 hr @ 120°C
2. Dissolve in dichloromethane
3. Precipitate into room temp. Diethylether/hexane (70/30) mixture 1. Tetrakis(triphenylphosphine)Palladium (0) deprotection catalyst and Morpholine in dichloromethane; 2 hr at room temperature
2. Precipitate into Diethylether/hexane (70/30) mixture at room temperature

PLA - PEG - GL2

Mn (PLA) = 16,000 Da (y = 222);

Mn (PEG) = 5000 Da (z = 114)

(A) Particle formation and hardening (upstream processing).

(B) Particle work up and purification (downstream processing).

DRUG LOADED POLYMERIC NANOPARTICLES AND METHODS OF MAKING AND USING SAME

RELATED APPLICATIONS

This application is a continuation of U.S. Ser. No. 12/485,399 filed Jun. 16, 2009 which claims priority to U.S. Ser. No. 61/061,760, filed Jun. 16, 2008; U.S. Ser. No. 61/105,916, filed Oct. 16, 2008, U.S. Ser. No. 61/106,777, filed Oct. 20, 2008; U.S. Ser. No. 61/169,514, filed Apr. 15, 2009; U.S. Ser. No. 61/175,209, filed May 4, 2009; U.S. Ser. No. 61/061,704, filed Jun. 16, 2008; U.S. Ser. No. 61/169,519, filed Apr. 15, 2009; U.S. Ser. No. 61/175,219 filed May 4, 2009; U.S. Ser. No. 61/061,697, filed Jun. 16, 2008; U.S. Ser. No. 61/088,159, filed Aug. 12, 2008; U.S. Ser. No. 61/169,541, filed Apr. 15, 2009; U.S. Ser. No. 61/175,226, filed May 4, 2009; U.S. Ser. No. 61/173,784, filed Apr. 29, 2009; U.S. Ser. No. 61/182,300, filed May 29, 2009; and U.S. Ser. No. 61/173,790, filed Apr. 29, 2009; each of which is hereby incorporated by reference in their entirety.

This invention was made with U.S. Government support under Cooperative Agreement Number 70NANB7H7021 awarded by the National Institute of Standard and Technology (NIST). The U.S. Government has certain rights in the Invention.

BACKGROUND

Systems that deliver certain drugs to a patient (e.g., targeted to a particular tissue or cell type or targeted to a specific diseased tissue but not normal tissue), or that control release of drugs has long been recognized as beneficial.

For example, therapeutics that include an active drug and that are e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy also must be able to deliver an effective amount of drug, which is a known limitation in other nanoparticle delivery systems. For example, it can be a challenge to prepare nanoparticle systems that have an appropriate amount of drug associated each nanoparticle, while keeping the size of the nanoparticles small enough to have advantageous delivery properties. However, while it is desirable to load a nanoparticle with a high quantity of therapeutic agent, nanoparticle preparations that use a drug load that is too high will result in nanoparticles that are too large for practical therapeutic use.

Accordingly, a need exists for nanoparticle therapeutics and methods of making such nanoparticles, that are capable of delivering therapeutic levels of drug to treat diseases such as cancer, while also reducing patient side effects.

SUMMARY

In one aspect, the invention provides therapeutic nanoparticle that includes an active agent or therapeutic agent, e.g. taxane, and one, two, or three biocompatible polymers. For example, disclosed herein is a therapeutic nanoparticle comprising about 0.2 to about 35 weight percent of a therapeutic agent; about 10 to about 99 weight percent poly(lactic) acid-block-poly(ethylene)glycol copolymer or poly(lactic)-co-poly (glycolic) acid-block-poly(ethylene)glycol copolymer; and about 0 to about 50 weight percent poly(lactic) acid or poly(lactic) acid-co-poly (glycolic) acid. Exemplary therapeutic agents include antineoplastic agents such as taxanes, e.g. docetaxel and may include about 10 to about 30 weight percent of a therapeutic agent, e.g., a taxane agent.

The hydrodynamic diameter of disclosed nanoparticles may be, for example, about 60 to about 120 nm, or about 70 to about 120 nm.

Exemplary therapeutic nanoparticles may include about 40 to about 90 weight percent poly(lactic) acid-poly(ethylene) glycol copolymer or about 40 to about 80 weight percent poly(lactic) acid-poly(ethylene)glycol copolymer. Such poly (lactic) acid-block-poly(ethylene)glycol copolymer may include poly(lactic acid) having a number average molecular weight of about 15 to 20 kDa (or for example about 15 to about 100 kDa, e.g. about 15 to about 80 kDa), and poly (ethylene)glycol having a number average molecular weight of about 2 to about 10 kDa, for example, about 4 to about 6 kDa. For example, a disclosed therapeutic nanoparticle may include about 70 to about 90 weight percent PLA-PEG and about 15 to about 25 weight percent docetaxel, or about 30 to about 50 weight percent PLA-PEG, about 30 to about 50 weight percent PLA or PLGA, and about 15 to about 25 weight percent doxetaxel. Such PLA ((poly)lactic acid) may have a number average molecular weight of about 5 to about 10 kDa. Such PLGA (poly lactic-co-glycolic acid) may have a number average molecular weight of about 8 to about 12 kDa.

Disclosed therapeutic nanoparticles may be stable (for example retains substantially most of the active agent) for at least 5 days at 25° C., e.g. may remain stable over 5 days in vitro, e.g. in a sucrose solution. In another embodiment, disclosed particles may substantially immediately release less than about 2% or less than about 5%, or even less than about 10% of the therapeutic agent when placed in a phosphate buffer solution at room temperature, or at 37° C. In an embodiment, disclosed nanoparticles may retain size and/or molecular weight for more than one week or one month or more.

In some embodiments, disclosed nanoparticles may further comprise about 0.2 to about 10 weight percent PLA-PEG functionalized with a targeting ligand and/or may include about 0.2 to about 10 weight percent poly (lactic) acid-co poly (glycolic) acid block-PEG-functionalized with a targeting ligand. Such a targeting ligand may be, in some embodiments, covalently bound to the PEG, for example, bound to the PEG via an alkylene linker, e.g. PLA-PEG-alkylene-GL2. For example, a disclosed nanoparticle may include about 0.2 to about 10 mole percent PLA-PEG-GL2 or poly (lactic) acid-co poly (glycolic) acid-PEG-GL2. It is understood that reference to PLA-PEG-GL2 or PLGA-PEG-GL2 refers to moieties that may include an alkylene linker (e.g. $C_1$-$C_{20}$, e.g., $(CH_2)_5$) linking the PEG to GL2. For example, a disclosed nanoparticle may be a polymeric compound selected from:

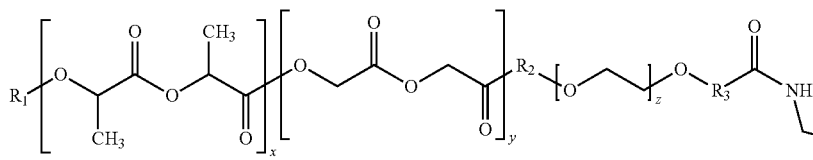

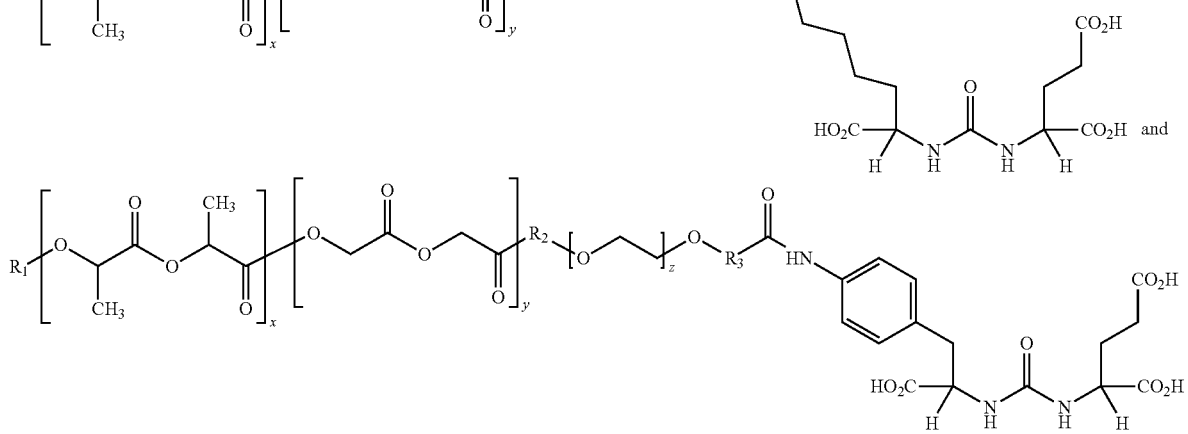

wherein $R_1$ is selected from the group consisting of H, and a $C_1$-$C_{20}$ alkyl group optionally substituted with halogen;

$R_2$ is a bond, an ester linkage, or amide linkage;

$R_3$ is an $C_1$-$C_{10}$ alkylene or a bond;

x is 50 to about 1500, for example about 170 to about 260;

y is 0 to about 50, for example y is 0; and z is about 30 to about 456, or about 30 to about 200, for example, z is about 80 to about 130.

In an embodiment, a therapeutic nanoparticle may include about 0.2 to about 35 weight percent of a therapeutic agent; about 30 to about 99 weight percent poly(lactic) acid-poly (ethylene)glycol copolymer or poly(lactic)-co-poly (glycolic) acid-poly(ethylene)glycol copolymer; about 0 to about 50 weight percent poly(lactic) acid or poly(lactic) acid-co-poly (glycolic) acid; and about 0.2 to about 10 weight percent, or about 0.2 to about 30 weight percent PLA-PEG-GL2 or poly (lactic) acid-co poly (glycolic) acid-PEG-GL2. For example, PLA-PEG-GL2 may include poly(lactic) acid with a number average molecular weight of about 10,000 Da to about 20,000 Da and poly(ethylene) glycol with a number average molecular weight of about 4,000 to about 8,000.

Compositions are provided such as composition comprising a plurality of disclosed nanoparticles and a pharmaceutically acceptable excipient. In some embodiments, such a composition may have less than about 10 ppm of palladium.

An exemplary composition may include a plurality of polymeric nanoparticles each comprising about 0.2 to about 35 weight percent of a taxane agent and about 10 to about 99 weight percent poly(lactic) acid-poly(ethylene)glycol copolymer or poly(lactic)-co-poly (glycolic) acid-poly(ethylene)glycol copolymer; and a pharmaceutically acceptable excipient, such as sucrose. Also provided herein is a nanoparticle formulation comprising: a plurality of disclosed nanoparticles, sucrose, and water; wherein for example, the weight ratio of nanoparticles/sucrose/water is about 5-10%/10-35%/60-90% (w/w/w), or about 4-10%/10-30%/60-90% (w/w/w).

Also provided herein are method of treating cancer, e.g. prostate cancer, comprising administering to a patient in need thereof an effective amount of therapeutic nanoparticles comprising about 0.2 to about 35 weight percent of an antineoplastic agent such as doxetaxel; about 30 to about 90 weight percent poly(lactic) acid-poly(ethylene)glycol copolymer or poly(lactic)-co-poly (glycolic) acid-poly(ethylene)glycol copolymer; optionally, about 5 to about 20 weight percent poly(lactic) acid or poly(lactic) acid-co-poly (glycolic) acid; and, optionally, about 0.2 to about 30 weight percent (e.g., about 0.2 to about 20 weight percent, or about 0.2 to about 10 weight percent) PLA-PEG-GL2 or poly (lactic) acid-co poly (glycolic) acid-PEG-GL2.

DETAILED DESCRIPTION

Figure 1:
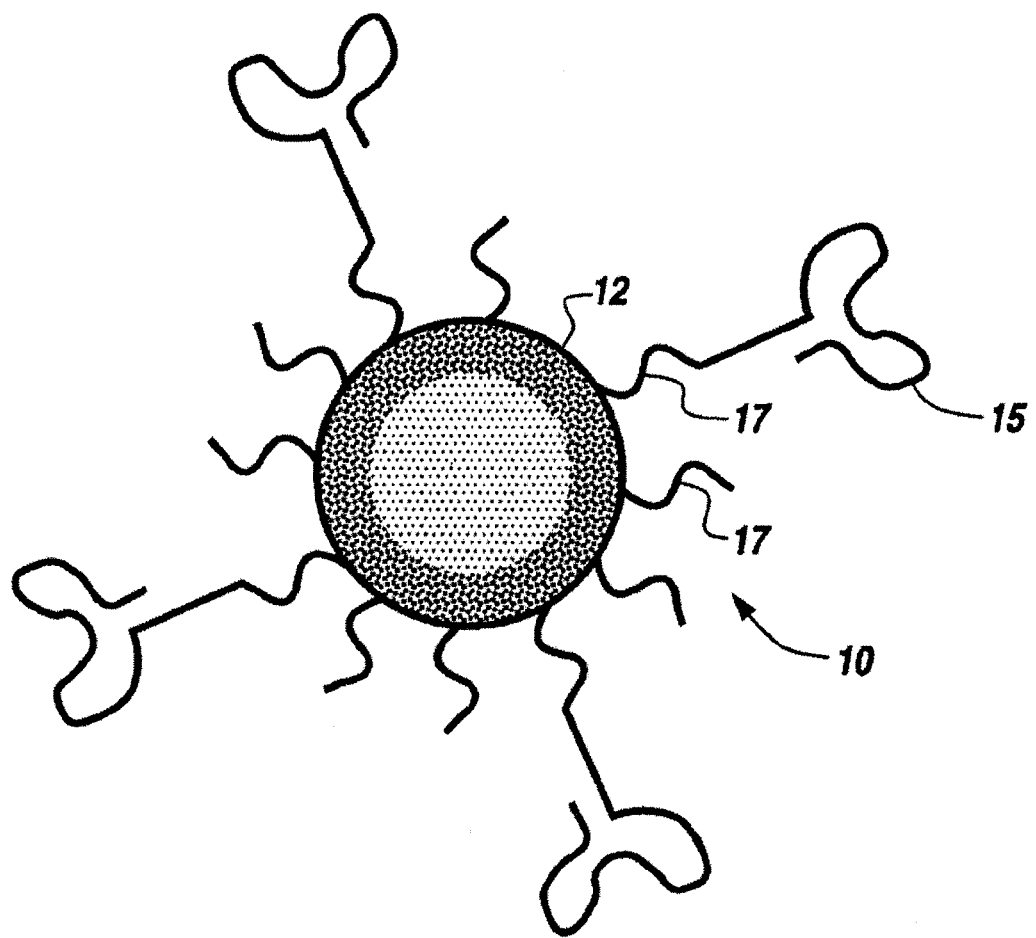
FIG. 1 depicts a pictorial representation of one embodiment of a disclosed nanoparticle.

The present invention generally relates to polymeric nanoparticles that include an active or therapeutic agent or drug, and methods of making and using such therapeutic nanoparticles. In general, a "nanoparticle" refers to any particle having a diameter of less than 1000 nm, e.g. about 10 nm to about 200 nm. Disclosed therapeutic nanoparticles may include nanoparticles having a diameter of about 60 to about 120 nm, or about 70 to about 130 nm, or about 60 to about 140 nm.

Disclosed nanoparticles may include about 0.2 to about 35 weight percent, about 3 to about 40 weight percent, about 5 to about 30 weight percent, 10 to about 30 weight percent, 15 to 25 weight percent, or even about 4 to about 25 weight percent of an active agent, such as antineoplastic agent, e.g. a taxane agent (for example docetaxel).

Nanoparticles disclosed herein include one, two, three or more biocompatible and/or biodegradable polymers. For example, a contemplated nanoparticle may include about 10 to about 99 weight percent of a one or more block co-polymers that include a biodegradable polymer and polyethylene glycol, and about 0 to about 50 weight percent of a biodegradable homopolymer.

In one embodiment, disclosed therapeutic nanoparticles may include a targeting ligand, e.g., a low-molecular weight PSMA ligand effective for the treatment of a disease or disorder, such as prostate cancer, in a subject in need thereof. In certain embodiments, the low-molecular weight ligand is conjugated to a polymer, and the nanoparticle comprises a certain ratio of ligand-conjugated polymer(e.g., PLA-PEG-Ligand) to non-functionalized polymer (e.g. PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder (e.g., prostate cancer). Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

For example, disclosed herein are nanoparticles that may include functionalized polymers conjugated to a ligand that constitute approximately 0.1-50, e.g., 0.1-30, e.g., 0.1-20, e.g., 0.1-10 mole percent of the entire polymer composition of the nanoparticle (i.e., functionalized+non-functionalized polymer). Also disclosed herein, in another embodiment, are nanoparticles that include a polymer conjugated (e.g., covalently with (i.e. through a linker (e.g. an alkylene linker) or a bond) with one or more low-molecular weight ligands, wherein the weight percent low-molecular weight ligand with respect to total polymer is between about 0.001 and 5, e.g., between about 0.001 and 2, e.g., between about 0.001 and 1.

Also provided herein are polymeric nanoparticles that include about 2 about 20 weight percent active agent. For example, a composition comprising such nanoparticles may be capable of delivering an effective amount to e.g. a target body area of a patient.

For example, disclosed nanoparticles may be able to efficiently bind to or otherwise associate with a biological entity, for example, a particular membrane component or cell surface receptor. Targeting of a therapeutic agent (e.g., to a particular tissue or cell type, to a specific diseased tissue but not to normal tissue, etc.) is desirable for the treatment of tissue specific diseases such as solid tumor cancers (e.g. prostate cancer). For example, in contrast to systemic delivery of a cytotoxic anti-cancer agent, the nanoparticles disclosed herein may substantially prevent the agent from killing healthy cells. Additionally, disclosed nanoparticles may allow for the administration of a lower dose of the agent (as compared to an effective amount of agent administered without disclosed nanoparticles or formulations) which may reduce the undesirable side effects commonly associated with traditional chemotherapy.

Polymers

In some embodiments, the nanoparticles of the invention comprise a matrix of polymers and a therapeutic agent. In some embodiments, a therapeutic agent and/or targeting moiety (i.e., a low-molecular weight PSMA ligand) can be associated with at least part of the polymeric matrix. For example, in some embodiments, a targeting moiety (e.g. ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g. targeting moiety); and the second macromolecule comprising a second polymer that is not bound to a targeting moiety. The nanoparticle can optionally include one or more additional, unfunctionalized, polymers.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly (glycerol sebacate), polyglycolide, polylactide, PLGA, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly (4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R-O—R' bonds). In some embodiments of the invention, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, by ring opening polymerization techniques (ROMP), or the like In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene)glycol.

Disclosed nanoparticles may optionally include about 1 to about 50 weight percent poly(lactic) acid or poly(lactic) acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

In certain embodiments, the polymers of the nanoparticles can be conjugated to a lipid. The polymer can be, for example, a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil can comprise one or more fatty acid groups or salts thereof. In some embodiments, a fatty acid group can comprise digestible, long chain (e.g., $C_8$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

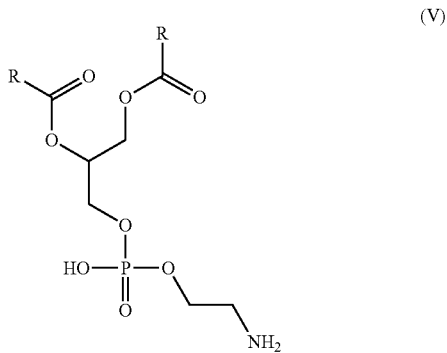

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

In one embodiment, optional small molecule targeting moieties are bonded, e.g., covalently bonded, to the lipid component of the nanoparticle. For example, provided herein is a nanoparticle comprising a therapeutic agent, a polymeric matrix comprising functionalized and non-functionalized polymers, and lipid, and a low-molecular weight PSMA targeting ligand, wherein the targeting ligand is bonded, e.g., covalently bonded, to the lipid component of the nanoparticle. In one embodiment, the lipid component that is bonded to the low-molecular weight targeting moiety is of the Formula V. In another embodiment, the invention provides a target-specific nanoparticle comprising a therapeutic agent, a polymeric matrix, DSPE, and a low-molecular weight PSMA targeting ligand, wherein the ligand is bonded, e.g., covalently bonded, to DSPE. For example, the nanoparticle of the invention may comprise a polymeric matrix comprising PLGA-DSPE-PEG-Ligand.

A contemplated nanoparticle may include a ratio of ligand-bound polymer to non-functionalized polymer effective for the treatment of prostate cancer, wherein the hydrophilic, ligand-bound polymer is conjugated to a lipid that will self assemble with the hydrophobic polymer, such that the hydrophobic and hydrophilic polymers that constitute the nanoparticle are not covalently bound. "Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. For example, such a method comprises providing a first polymer that is reacted with a lipid, to form a polymer/lipid conjugate. The polymer/lipid conjugate is then reacted with the low-molecular weight ligand to prepare a ligand-bound polymer/lipid conjugate; and mixing the ligand-bound polymer/lipid conjugate with a second, non-functionalized polymer, and the therapeutic agent; such that the nanoparticle is formed. In certain embodiments, the first polymer is PEG, such that a lipid-terminated PEG is formed. In one embodiment, the lipid is of the Formula V, e.g., 2 distearoyl-sn-glycero-3-phosphoethanolamine (DSPE), and salts thereof, e.g., the sodium salt. The lipid-terminated PEG can then, for example, be mixed with PLGA to form a nanoparticle.

Targeting Moieties

Provided herein are nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

In one embodiment, a disclosed nanoparticle includes a targeting moiety that is a low-molecular weight ligand, e.g., a low-molecular weight PSMA ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

For example, a targeting portion may cause the particles to become localized to a tumor (e.g. a solid tumor) a disease site, a tissue, an organ, a type of cell, etc. within the body of a subject, depending on the targeting moiety used. For example, a low-molecular weight PSMA ligand may become localized to a solid tumor, e.g. breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol.

For example, a targeting moiety may small target prostate cancer tumors, for example a target moiety may be PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, Clin. Cancer Res., 3:81).

In some embodiments, the low-molecular weight PSMA ligand is of the Formulae I, II, III or IV:

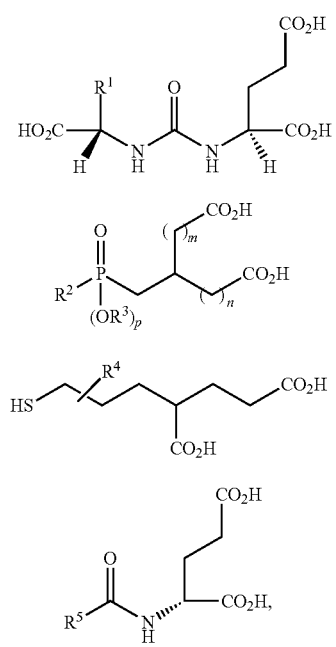

and enantiomers, stereoisomers, rotamers, tautomers, diastereomers, or racemates thereof;

wherein m and n are each, independently, 0, 1, 2 or 3; p is 0 or 1;

$R^1$, $R^2$, $R^4$ and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyrdinyl), and any combination thereof; and $R^3$ is H or C alkyl (e.g., $CH_3$).

For compounds of Formulae I, II, III and IV, $R^1$, $R^2$, $R^4$ or $R^3$ comprise points of attachment to the nanoparticle, e.g., a point of attachment to a polymer that forms part of a disclosed nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$ or $R^5$ are defined as an aniline or $C_{1-6}$-alkyl-$NH_2$ group, any hydrogen (e.g., an amino hydrogen) of these functional groups could be removed such that the low-molecular weight PSMA ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$ and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S or O. In another embodiment, $R^1$, $R^2$, $R^4$ and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)—Ph, O—$CH_2$—Ph, or O—$(CH_2)_2$—Ph, wherein each Ph may be independently substituted one or more times with OH, $NH_2$, $CO_2H$ or SH. For these formulae, the $NH_2$, OH or SH groups serve as the point of covalent attachment to the nanoparticle (e.g., —N(H)-PEG, —O-PEG, or —S-PEG).

In still another embodiment, the low-molecular weight PSMA ligand is selected from the group consisting of

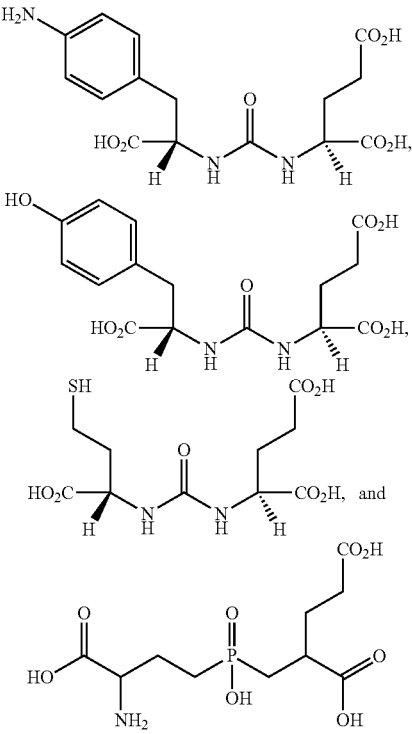

and enantiomers, stereoisomers, rotamers, tautomers, diastereomers, or racemates thereof, and wherein the NH$_2$, OH or SH groups serve as the point of covalent attachment to the nanoparticle (e.g., —N(H)-PEG, —O-PEG, or —S-PEG).

In another embodiment, the low-molecular weight PSMA ligand is selected from the group consisting of

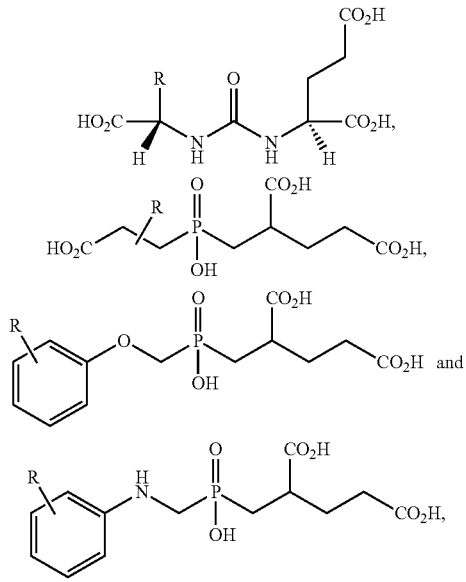

and enantiomers, stereoisomers, rotamers, tautomers, diastereomers, or racemates thereof, wherein R is independently selected from the group consisting of NH$_2$, SH, OH, CO$_2$H, C$_{1-6}$-alkyl that is substituted with NH$_2$, SH, OH or CO$_2$H, and phenyl that is substituted with NH$_2$, SH, OH or CO$_2$H, and wherein R serves as the point of covalent attachment to the nanoparticle (e.g., —N(H)-PEG, —S-PEG, —O-PEG, or CO$_2$-PEG).

In another embodiment, the low-molecular weight PSMA ligand is selected from the group consisting of

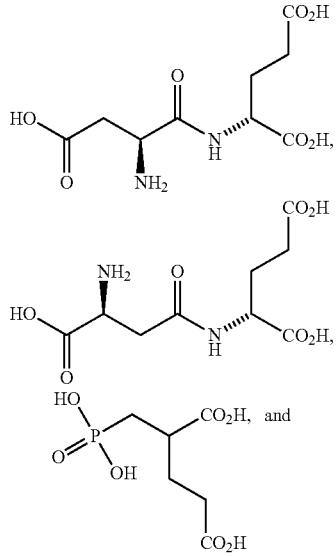

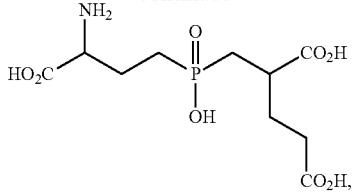

and enantiomers, stereoisomers, rotamers, tautomers, diastereomers, or racemates thereof, wherein the NH$_2$ or CO$_2$H groups serve as the point of covalent attachment to the nanoparticle (e.g., —N(H)-PEG, or CO$_2$-PEG). These compounds may be further substituted with NH$_2$, SH, OH, CO$_2$H, C$_{1-6}$-alkyl that is substituted with NH$_2$, SH, OH or CO$_2$H, or phenyl that is substituted with NH$_2$, SH, OH or CO$_2$H, wherein these functional groups can also serve as the point of covalent attachment to the nanoparticle.

In another embodiment, the low-molecular weight PSMA ligand is

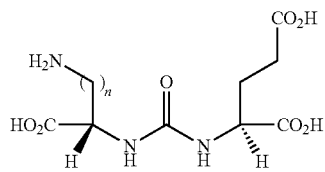

and enantiomers, stereoisomers, rotamers, tautomers, diastereomers, or racemates thereof, wherein n is 1, 2, 3, 4, 5 or 6. For this ligand, the NH$_2$ group serves as the point of covalent attachment to the nanoparticle (e.g., —N(H)-PEG).

In still another embodiment, the low-molecular weight PSMA ligand is

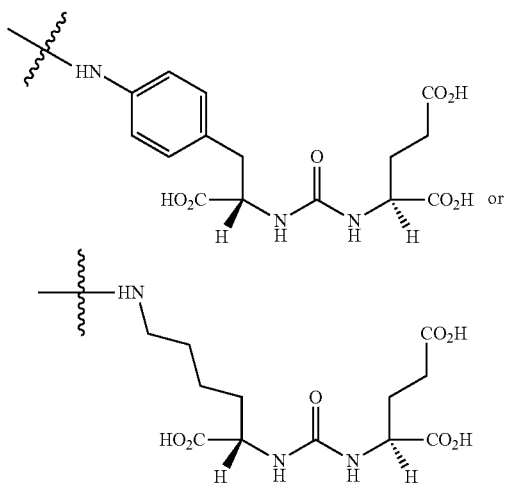

and enantiomers, stereoisomers, rotamers, tautomers, diastereomers, or racemates thereof. Particularly, the butyl-amine compound has the advantage of ease of synthesis, especially because of its lack of a benzene ring. Furthermore, without wishing to be bound by theory, the butyl-amine compound will likely break down into naturally occurring molecules (i.e., lysine and glutamic acid), thereby minimizing toxicity concerns.

In some embodiments, small molecule targeting moieties that may be used to target cells associated with solid tumors such as prostate or breast cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In another embodiment of the instant invention, the targeting moiety can be a ligand that targets Her2, EGFR, or toll receptors.

For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain targeting moieties can be identified, e.g., using procedures such as phage display.

Targeting moieties may be a targeting peptide or targeting peptidomimetic has a length of up to about 50 residues. For example, a targeting moieties may include the amino acid sequence AKERC, CREKA, ARYLQKLN or AXYLZZLN, wherein X and Z are variable amino acids, or conservative variants or peptidomimetics thereof. In particular embodiments, the targeting moiety is a peptide that includes the amino acid sequence AKERC, CREKA, ARYLQKLN or AXYLZZLN, wherein X and Z are variable amino acids, and has a length of less than 20, 50 or 100 residues. The CREKA (Cys Arg Glu Lys Ala) peptide or a peptidomimetic thereof peptide or the octapeptide AXYLZZLN are also comtemplated as targeting moities, as well as peptides, or conservative variants or peptidomimetics thereof, that binds or forms a complex with collagen IV, or the targets tissue basement membrane (e.g., the basement membrane of a blood vessel), can be used as a targeting moiety. Exemplary targeting moieties include peptides that target ICAM (intercellular adhesion molecule, e.g. ICAM-1).

Targeting moieties disclosed herein are typically conjugated to a disclosed polymer or copolymer (e.g. PLA-PEG), and such a polymer conjugate may form part of a disclosed nanoparticle. For example, a disclosed therapeutic nanoparticle may optionally include about 0.2 to about 10 weight percent of a PLA-PEG or PLGA-PEG, wherein the PEG is functionalized with a targeting ligand (e.g. PLA-PEG-Ligand). Contemplated therapeutic nanoparticles may include, for example, about 0.2 to about 10 mole percent PLA-PEG-GL2 or poly (lactic) acid-co poly (glycolic) acid-PEG-GL2. For example, PLA-PEG-GL2 may include a number average molecular weight of about 10 kDa to about 20 kDa and a number average molecular weight of about 4,000 to about 8,000.

Such a targeting ligand may be, in some embodiments, covalently bound to the PEG, for example, bound to the PEG via an alkylene linker, e.g. PLA-PEG-alkylene-GL2. For example, a disclosed nanoparticle may include about 0.2 to about 10 mole percent PLA-PEG-GL2 or poly (lactic) acid-co poly (glycolic) acid-PEG-GL2. It is understood that reference to PLA-PEG-GL2 or PLGA-PEG-GL2 refers to moieties that may include an alkylene linker (e.g. $C_1$-$C_{20}$, e.g., $(CH_2)_5$) linking a PLA-PEG or PLGA-PEG to GL2.

Exemplary polymeric conjugates include:

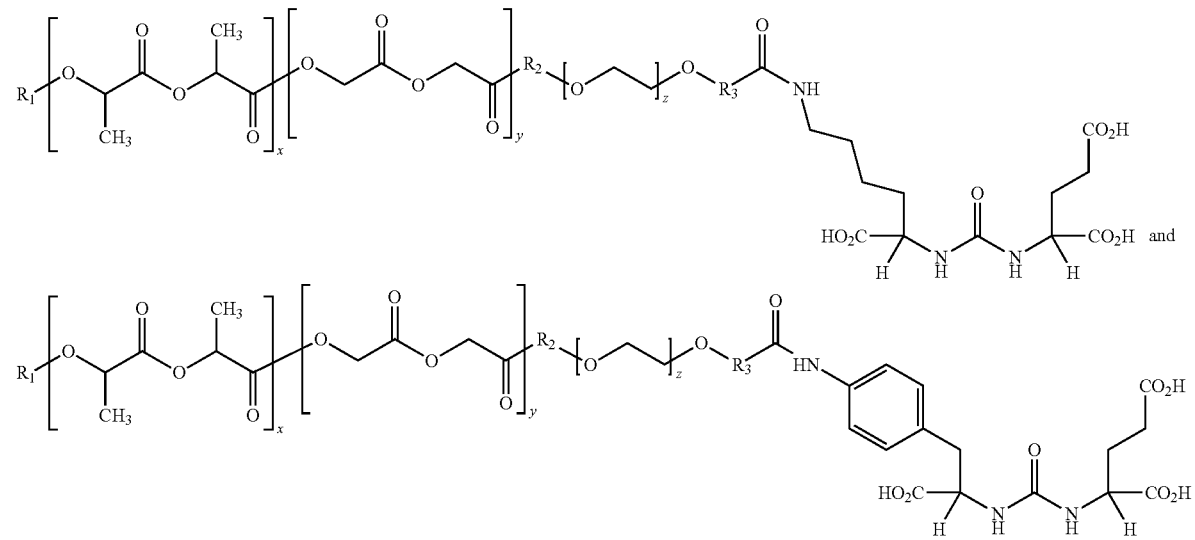

wherein $R_1$ is selected from the group consisting of H, and a $C_1$-$C_{20}$ alkyl group optionally substituted with one, two, three or more halogens,;

$R_2$ is a bond, an ester linkage, or amide linkage;

$R_3$ is an $C_1$-$C_{10}$ alkylene or a bond;

x is 50 to about 1500, or about 60 to about 1000;
y is 0 to about 50; and
z is about 30 to about 200, or about 50 to about 180.

In a different embodiment, x represents 0 to about 1 mole fraction; and y may represent about 0 to about 0.5 mole fraction. In an exemplary embodiment, x+y may be about 20 to about 1720, and/or z may be about 25 to about 455.

For example, a disclosed nanoparticle may include a polymeric targeting moiety represented by Formula VI:

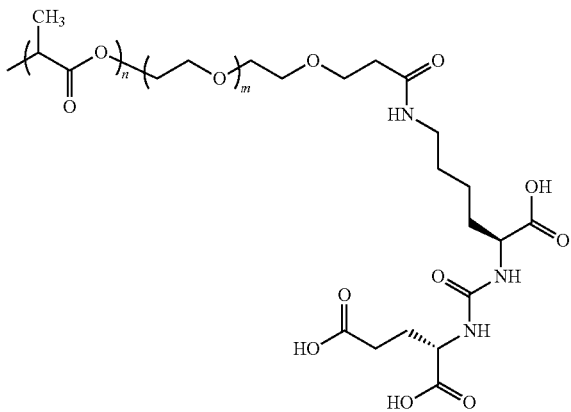

wherein n is about 200 to about 300, e.g., about 222, and m is about 80 to about 130, e.g. about 114. Disclosed nanoparticles, in certain embodiments, may include about 0.1 to about 4% by weight of e.g. a polymeric conjugate of formula VI, or about 0.1 to about 2% or about 0.1 to about 1%, or about 0.2% to about 0.8% by weight of e.g., a polymeric conjugate of formula VI.

In an exemplary embodiment, a disclosed nanoparticle comprises a nanoparticle having a PLA-PEG-alkylene-GL2 conjugate, where, for example, PLA has a number average molecular weight of about 16,000 Da, PEG has a molecular weight of about 5000 Da, and e.g., the alkylene linker is a $C_1$-$C_{20}$ alkylene, e.g. $(CH_2)_5$.

For example, a disclosed nanoparticle may include a conjugate represented by:

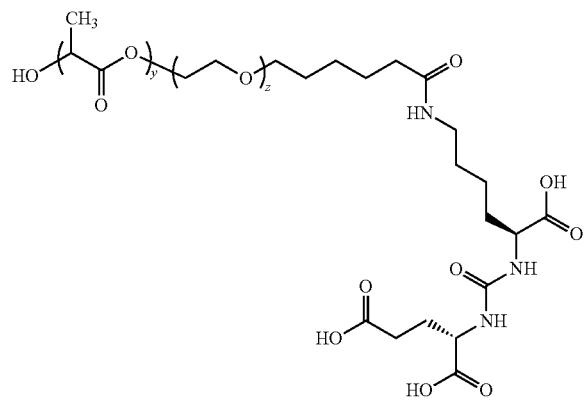

where y is about 222 and z is about 114.

A disclosed polymeric conjugate may be formed using any suitable conjugation technique. For instance, two compounds such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as a low-molecular weight PSMA ligand, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol.

As a specific example, a low-molecular weight PSMA ligand may be prepared as a targeting moiety in a particle as follows. Carboxylic acid modified poly(lactide-co-glycolide) (PLGA-COOH) may be conjugated to an amine-modified heterobifunctional poly(ethylene glycol) ($NH_2$-PEG-COOH) to form a copolymer of PLGA-PEG-COOH. By using an amine-modified low-molecular weight PSMA ligand ($NH_2$-Lig), a triblock polymer of PLGA-PEG-Lig may be formed by conjugating the carboxylic acid end of the PEG to the amine functional group on the ligand. The multiblock polymer can then be used, for instance, as discussed below, e.g., for therapeutic applications.

As used herein, the term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups.

The term "aryl" includes groups, including 5- and 6-membered single-ring aromatic groups that can include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multiciclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure can also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

Targeting moities can be, for example, further substituted with a functional group that can be reacted with a polymer of the invention (e.g., PEG) in order to produce a polymer conjugated to a targeting moiety. The functional groups include any moiety that can be used to create a covalent bond with a polymer (e.g., PEG), such as amino, hydroxy, and thio. In a particular embodiment, the small molecules can be substituted with $NH_2$, SH or OH, which are either bound directly to the small molecule, or bound to the small molecule via an additional group, e.g., alkyl or phenyl. In a non-limiting example, the small molecules disclosed in the patents, patent applications, and non-patent references cited herein may be bound to aniline, alkyl-$NH_2$ (e.g., $(CH_2)_{1-6}NH_2$), or alkyl-SH (e.g., $(CH_2)_{1-6}NH_2$), wherein the $NH_2$ and SH groups may be reacted with a polymer (e.g., PEG), to form a covalent bond with that polymer, i.e., to form a polymeric conjugate.

For example, disclosed herein is a nanoparticle having a therapeutic agent; and a first macromolecule comprising a PLGA-PEG copolymer or PLA-PEG copolymer that is conjugated to ligand having a molecular weight between about 100 g/mol and 500 g/mol wherein the PLGA-PEG copolymer or PLA-PEG copolymer that is conjugated to ligand is about 0.1 to about 30 mole percent of the total polymer content, or about 0.1 to about 20 mole percent, or about 0.1 to about 10 mole percent, or about 1 to about 5 mole percent of the total polymer content of a nanoparticle. Such a nanoparticle may further include a second macromolecule comprising a PLGA-PEG copolymer or PLA-PEG copolymer, wherein the copolymer is not bound to a targeting moiety; and a pharmaceutically acceptable excipient. For example, the first copolymer may have about 0.001 and 5 weight percent of the ligand with respect to total polymer content.

Exemplary nanoparticles may include a therapeutic agent; and a polymer composition, wherein the polymer composition comprises: a first macromolecule comprising first polymer bound to a ligand; and a second macromolecule comprising a second polymer not bound to a targeting moiety; wherein the polymer composition comprises about 0.001 to about 5.0 weight percent of said ligand. Such ligands may have a molecular weight of about 100 g/mol to about 6000 g/mol, or less than about 1000 g/mol, e.g. about 100 g/mole to about 500 g/mol. In another embodiment, provided herein is a pharmaceutical composition, comprising a plurality of target-specific polymeric nanoparticles each comprising a therapeutic agent; and a polymer composition, wherein the polymer composition comprises about 0.1 to about 30 mole percent, or about 0.1 to about 20 mole percent, or about 0.1 to about 10 mole percent of a first macromolecule comprising first polymer bound to a ligand; and a second macromolecule comprising a second polymer not bound to a targeting moiety; and a pharmaceutically acceptable excipient.

Nanoparticles

Disclosed nanoparticles may have a substantially spherical (i.e., the particles generally appear to be spherical), or non-spherical configuration. For instance, the particles, upon swelling or shrinkage, may adopt a non-spherical configuration. In some cases, the particles may include polymeric blends. For instance, a polymer blend may be formed that includes a first polymer comprising a targeting moiety (i.e., a low-molecular weight PSMA ligand) and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of about 80 nm-200 nm, about 60 nm to about 150 nm, or about 70 nm to about 200 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (i.e., a low-molecular weight ligand) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body will also be isolated from the drug. Yet another aspect of the invention is directed to polymer particles having more than one polymer or macromolecule present, and libraries involving such polymers or macromolecules. For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle can comprise a first diblock polymer comprising a poly(ethylene glycol) and a targeting moiety conjugated to the poly(ethylene glycol), and a second polymer comprising the poly(ethylene glycol) but not the targeting moiety, or comprising both the poly(ethylene glycol) and the targeting moiety, where the poly(ethylene glycol) of the second polymer has a different length (or number of repeat units) than the poly(ethylene glycol) of the first polymer. As another example, a particle may comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety.

For example, disclosed herein is a therapeutic polymeric nanoparticle capable of binding to a target, comprising a first non-functionalized polymer; an optional second non-functionalized polymer; a functionalized polymer comprising a targeting moiety; and a therapeutic agent; wherein said nanoparticle comprises about 15 to about 300 molecules of functionalized polymer, or about 20 to about 200 molecule, or about 3 to about 100 molecules of functionalized polymer.

In a particular embodiment, the polymer of the first or second macromolecules of the nanoparticle of the invention is PLA, PLGA, or PEG, or copolymers thereof. In a specific embodiment, the polymer of the first macromolecule is a PLGA-PEG copolymer, and the second macromolecule is a PLGA-PEG copolymer, or a PLA-PEG copolymer. For example, exemplary nanoparticle may have a PEG corona with a density of about 0.065 g/cm$^3$, or about 0.01 to about 0.10 g/cm$^3$.

Disclosed nanoparticles may be stable (e.g. retain substantially all active agent) for example in a solution that may contain a saccharide, for at least about 3 days, about 4 days or at least about 5 days at room temperature, or at 25° C.

In some embodiments, disclosed nanoparticles may also include a fatty alcohol, which may increase the rate of drug release. For example, disclosed nanoparticles may include a $C_8$-$C_{30}$ alcohol such as cetyl alcohol, octanol, stearyl alcohol, arachidyl alcohol, docosonal, or octasonal.

Nanoparticles may have controlled release properties, e.g., may be capable of delivering an amount of active agent to a patient, e.g., to specific site in a patient, over an extended period of time, e.g. over 1 day, 1 week, or more. In some embodiments, disclosed nanoparticles substantially immediately releases (e.g. over about 1 minute to about 30 minutes) less than about 2%, less than about 5%, or less than about 10% of an active agent (e.g. a taxane) agent, for example when places in a phosphate buffer solution at room temperature and/or at 37° C.

For example, disclosed nanoparticles that include a therapeutic agent, may, in some embodiments, may release the therapeutic agent when placed in an aqueous solution at e.g., 25 C with a rate substantially corresponding to a) from about 0.01 to about 20% of the total therapeutic agent is released after about 1 hour; b) from about 10 to about 60% of the therapeutic agent is released after about 8 hours; c) from about 30 to about 80% of the total therapeutic agent is released after about 12 hours; and d) not less than about 75% of the total is released after about 24 hours.

In some embodiments, after administration to a subject or patient of a disclosed nanoparticle or a composition that includes a disclosed nanoparticle, the peak plasma concentration ($C_{max}$) of the therapeutic agent in the patient s substantially higher as compared to a $C_{max}$ of the therapeutic agent if administered alone (e.g., not as part of a nanoparticle).

In another embodiment, a disclosed nanoparticle including a therapeutic agent, when administered to a subject, may have a $t_{max}$ of therapeutic agent substantially longer as compared to a $t_{max}$ of the therapeutic agent administered alone.

Libraries of such particles may also be formed. For example, by varying the ratios of the two (or more) polymers within the particle, these libraries can be useful for screening tests, high-throughput assays, or the like. Entities within the library may vary by properties such as those described above, and in some cases, more than one property of the particles may be varied within the library. Accordingly, one embodiment of the invention is directed to a library of nanoparticles having different ratios of polymers with differing properties. The library may include any suitable ratio(s) of the polymers.

FIG. 1 illustrates that libraries can be produced using polymers such as those described above. For example, in FIG. 1, polymeric particles comprising a first macromolecule comprising a biocompatible hydrophobic polymer, a biocompatible hydrophilic polymer, and a low-molecular weight PSMA ligand, and a second macromolecule that comprises a biocompatible hydrophobic polymer and a biocompatible hydrophilic polymer may be used to create a library of particles having different ratios of the first and second macromolecules.

Such a library may be useful in achieving particles having any number of desirable properties, for instance properties such as surface functionality, surface charge, size, zeta (C) potential, hydrophobicity, ability to control immunogenicity, or the like.

As specific examples, in some embodiments of the present invention, the library includes particles comprising polymeric conjugates of a biocompatible polymer and a low-molecular weight ligand, as discussed herein. Referring now to FIG. 1, one such particle is shown as a non-limiting example. In this figure, a polymeric conjugate of the disclosure is used to form a particle 10. The polymer forming particle 10 includes a low-molecular weight ligand 15, present on the surface of the particle, and a biocompatible portion 17. In some cases, as shown here, targeting moiety 15 may be conjugated to biocompatible portion 17. However, not all of biocompatible portion 17 is shown conjugated to targeting moiety 15. For instance, in some cases, particles such as particle 10 may be formed using a first polymer comprising biocompatible portion 17 and low-molecular weight ligand 15, and a second polymer comprising biocompatible portion 17 but not targeting moiety 15. By controlling the ratio of the first and second polymers, particles having different properties may be formed, and in some cases, libraries of such particles may be formed. In addition, contained within the center of particle 10 is drug 12. In some cases, drug 12 may be contained within the particle due to hydrophobic effects. For instance, the interior of the particle may be relatively hydrophobic with respect to the surface of the particle, and the drug may be a hydrophobic drug that associates with the relatively hydrophobic center of the particle. In one embodiment, the therapeutic agent is associated with the surface of, encapsulated within, surrounded by, or dispersed throughout the nanoparticle. In another embodiment, the therapeutic agent is encapsulated within the hydrophobic core of the nanoparticle.

As a specific example, particle 10 may contain polymers including a relatively hydrophobic biocompatible polymer and a relatively hydrophilic targeting moiety 15, such that, during particle formation, a greater concentration of the hydrophilic targeting moiety is exposed on the surface and a greater concentration of the hydrophobic biocompatible polymer is present within the interior of the particle.

In some embodiments, the biocompatible polymer is a hydrophobic polymer. Non-limiting examples of biocompatible polymers include polylactide, polyglycolide, and/or poly(lactide-co-glycolide).

In a different embodiment, this disclosure provides for a nanoparticle comprising 1) a polymeric matrix; 2) optionally, an amphiphilic compound or layer that surrounds or is dispersed within the polymeric matrix forming a continuous or discontinuous shell for the particle; 3) a non-functionalized polymer that may form part of the polymeric matrix, and 4) a low molecular weight PSMA ligand covalently attached to a polymer, which may form part of the polymeric matrix. For example, an amphiphilic layer may reduce water penetration into the nanoparticle, thereby enhancing drug encapsulation efficiency and slowing drug release.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid.

In certain embodiments a disclosed nanoparticle has an amphiphilic monolayer, meaning the layer is not a phospholipid bilayer, but exists as a single continuous or discontinuous layer around, or within, the nanoparticle. The amphiphilic layer is "associated with" the nanoparticle of the invention, meaning it is positioned in some proximity to the polymeric matrix, such as surrounding the outside of the polymeric shell, or dispersed within the polymers that make up the nanoparticle.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight PSMA ligand, while another polymer (e.g., copolymer, e.g., block copolymer) may be chosen for its biocompatibility and/or its ability to control immunogenicity of the resultant particle.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell or biological media, ethanol, etc.)

are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta ($\zeta$) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties (e.g., low-molecular weight PSMA ligands) present on the surface of the particle. This allows particles having one or more specific properties to be prepared, for example, a specific size and a specific surface density of moieties, without an undue degree of effort. Accordingly, certain embodiments of the invention are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. For example, a first copolymer (PLGA-PEG, poly(lactide-co-glycolide) and poly(ethylene glycol)) is mixed with a therapeutic agent to form particles. The particles are then associated with a low-molecular weight ligand to form nanoparticles that can be used for the treatment of cancer. The particles can be associated with varying amounts of low-molecular weight ligands in order to control the ligand surface density of the nanoparticle, thereby altering the therapeutic characteristics of the nanoparticle. Furthermore, for example, by controlling parameters such as molecular weight, the molecular weight of PEG, and the nanoparticle surface charge, very precisely controlled particles may be obtained.

Figure 3:
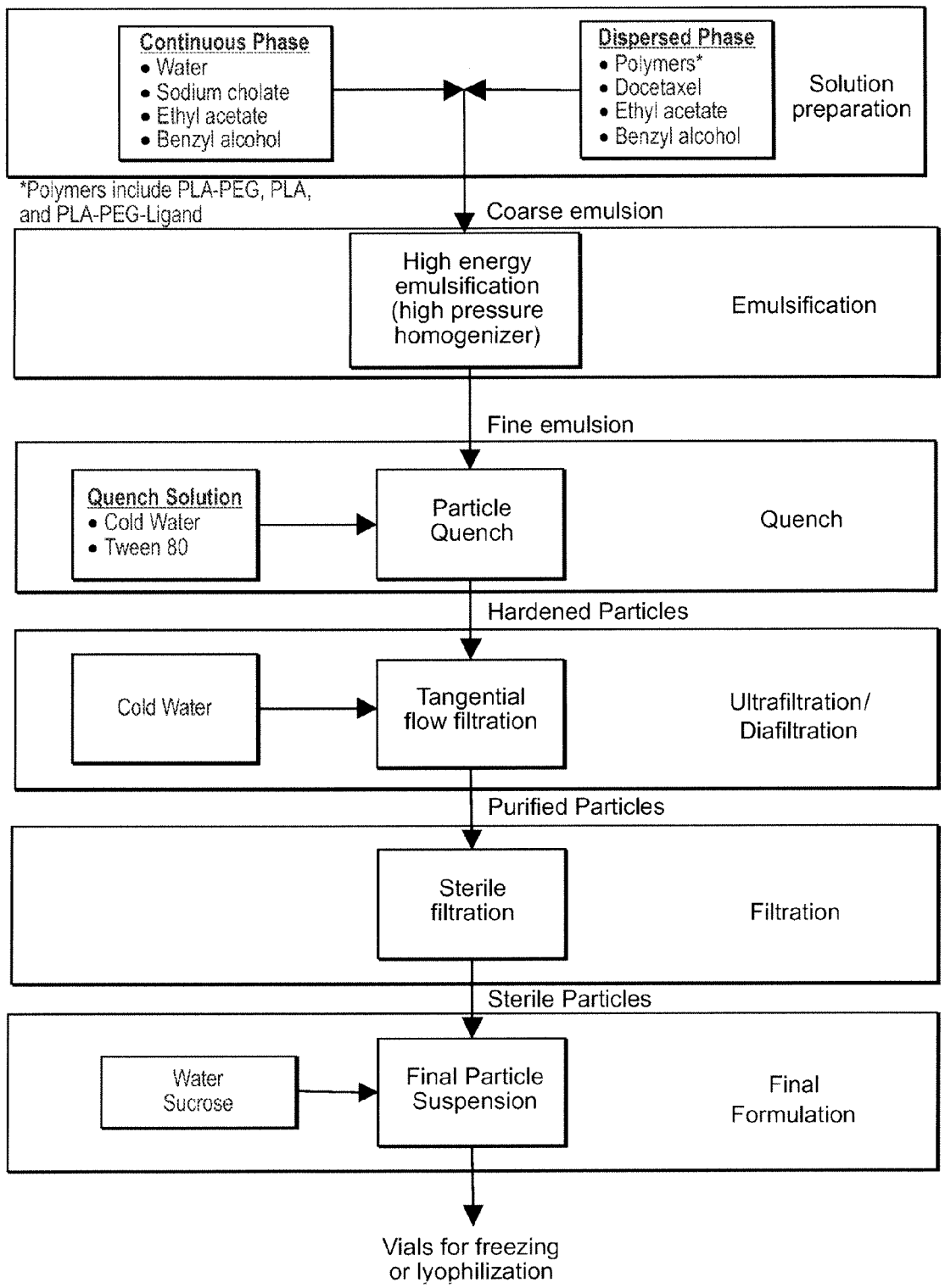
FIG. 3 is flow chart for an emulsion process for forming disclosed nanoparticle.
Figure 4A:
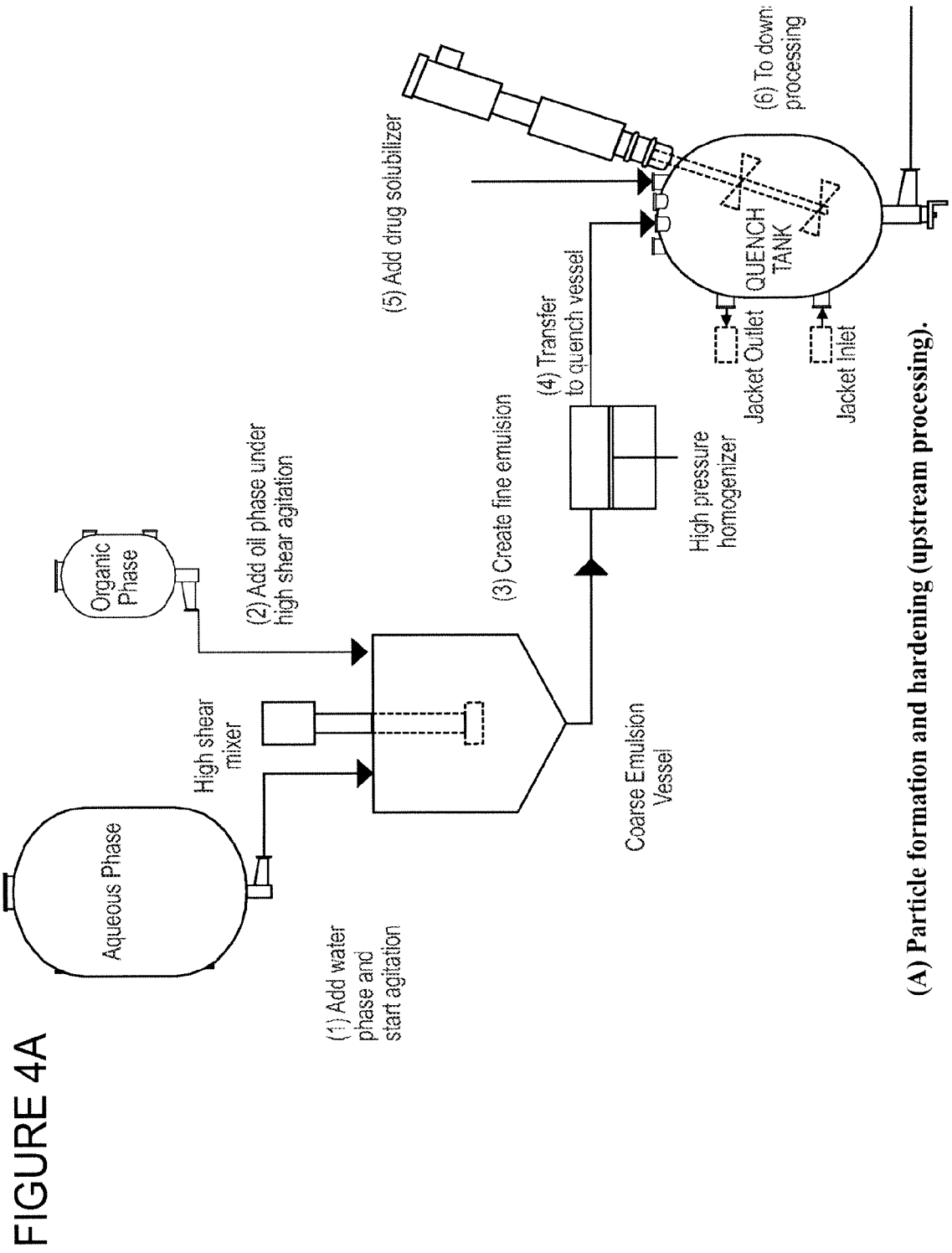
FIG. 4 is a flow diagram for a disclosed emulsion process.
Figure 4B:
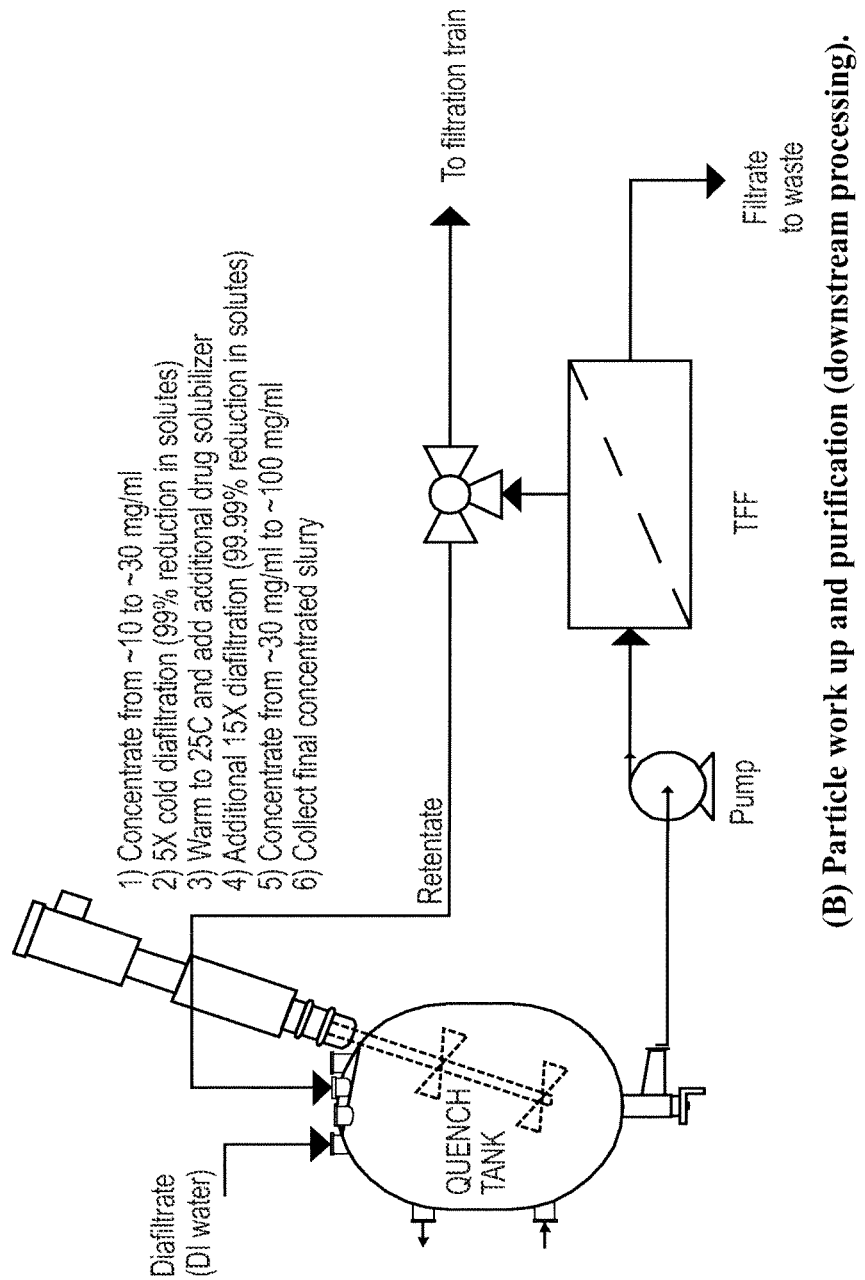

In another embodiment, a nanoemulsion process is provided, such as the process represented in FIGS. 3 and 4. For example, a therapeutic agent, a first polymer (for example, a diblock co-polymer such as PLA-PEG or PLGA-PEG, either of which may be optionally bound to a ligand, e.g., GL2) and an optional second polymer (e.g. (PL(G)A-PEG or PLA), with an organic solution to form a first organic phase. Such first phase may include about 5 to about 50% weight solids, e.g about 5 to about 40% solids, or about 10 to about 30% solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 1 and 50 weight %, e.g., about 5-40 weight %, solids. The aqueous solution can be water, optionally in combination with one or more of sodium cholate, ethyl acetate, polyvinyl acetate and benzyl alcohol.

For example, the oil or organic phase may use solvent that is only partially miscible with the nonsolvent (water). Therefore, when mixed at a low enough ratio and/or when using water pre-saturated with the organic solvents, the oil phase remains liquid. The oil phase may bee emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g. probe sonicator or a high pressure homogenizer, e.g. by using 1, 2, 3 or more passes through a homogenizer. For example, when a high pressure homogenizer is used, the pressure used may be about 1000 to about 8000 psi, about 2000 to about 4000 psi4000 to about 8000 psi, or about 4000 to about 5000 psi, e.g., about 2000, 2500, 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g. about 0 to about 10° C., or about 0 to about 5° C.).

In some embodiments, not all of the therapeutic agent (e.g. docetaxel) is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, or sodium cholate. For example, Tween-80 may added to the quenched nanoparticle suspension to solubilize the free drug and prevent the formation of drug crystals. In some embodiments, a ratio of drug solubilizer to therapeutic agent (e.g. docetaxel) is about 100:1 to about 10:1.

The solubilized phase may be filtered to recover the nanoparticles. For example, ultrafiltration membranes may be used to concentrate the nanoparticle suspension and substantially eliminate organic solvent, free drug, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g. about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. For example, filtering may include processing about 1 to about 6 diavolumes at about 0 to about 5° C., and processing at least one diavolume (e.g. about 1 to about 3 or about 1-2 diavolumes) at about 20 to about 30° C.

After purifying and concentrating the nanoparticle suspension, the particles may be passed through one, two or more sterilizing and/or depth filters, for example, using ~0.2 μm depth pre-filter.

In another embodiment of preparing nanoparticles, an organic phase is formed composed of a mixture of a therapeutic agent, e.g., docetaxel, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. The quench:emulsion ratio is approximately 8.5:1. Then a solution of Tween (e.g., Tween 80) is added to the quench to achieve approximately 2% Tween overall. This serves to dissolve free, unencapsulated drug. The nanoparticles are then isolated through either centrifugation or ultrafiltration/diafiltration.

It will be appreciated that the amounts of polymer and therapeutic or active agent that are used in the preparation of the formulation may differ from a final formulation. For example, some active agent may not become completely incorporated in a nanoparticle and such free therapeutic agent may be e.g. filtered away. For example, in an embodiment, about 20 weight percent of active agent (e.g. docetaxel) and about 80 weight percent polymer (e.g. the polymer may include about 2.5 mol percent PLA-PEG-GL2 and about 97.5 mol percent PLA-PEG). may be used in the preparation of a formulation that results in an e.g. final nanoparticle comprising about 10 weight percent active agent (e.g. docetaxel) and about 90 weight percent polymer (where the polymer may include about 1.25 mol percent PLA-PEG-GL2 and about 98.75 mol percent PLA-PEG). Such processes may provide final nanoparticles suitable for administration to a patient that includes about 2 to about 20 percent by weight therapeutic agent, e.g. about 5, about 8, about 10, about 15 percent therapeutic agent by weight.

Therapeutic Agents

According to the present invention, any agents including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the disclosed nanoparticles. Exemplary agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

For instance, a targeting moiety, if used, may target or cause the particle to become localized at specific portions within a subject, and the payload may be delivered to those portions. In a particular embodiment, the drug or other payload may be released in a controlled release manner from the particle and allowed to interact locally with the particular targeting site (e.g., a tumor). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The active agent or drug may be a therapeutic agent such as an antineoplastic such as mTor inhibitors (e.g., sirolimus, temsirolimus, or everolimus), vinca alkaloids such as vincristine, a diterpene derivative or a taxane such as paclitaxel (or its derivatives such as DHA-paclitaxel or PG-paxlitaxel) or docetaxel.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. Exemplary therapeutic agents include chemotherapeutic agents such as doxorubicin (adriamycin), gemcitabine (gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), aldesleukin, asparaginase, busulfan, carboplatin, cladribine, camptothecin, CPT-11, 10-hydroxy-7-ethylcamptothecin (SN38), dacarbazine, S—I capecitabine, ftorafur, 5' deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

Non-limiting examples of potentially suitable drugs include anti-cancer agents, including, for example, docetaxel, mitoxantrone, and mitoxantrone hydrochloride. In another embodiment, the payload may be an anti-cancer drug such as 20-epi-1, 25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTEA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C uihibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

Pharmaceutical Formulations

Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of the PSMA-targeted particle is chosen by the individual physician in view of the patient to be treated, in general, dosage and administration are adjusted to provide an effective amount of the PSMA-targeted particle to the patient being treated. As used herein, the "effective amount" of an PSMA-targeted particle refers to the amount necessary to elicit the desired biological response. As will be appreciated by those of ordinary skill in this art, the effective amount of PSMA-targeted particle may vary depending on such factors as the desired biological endpoint, the drug to be delivered, the target tissue, the route of administration, etc. For example, the effective amount of PSMA-targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy The nanoparticles of the invention may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of naoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may include less than about 10 ppm of palladium, or less than about 8 ppm, or less than about 6 ppm of palladium. For example, provided here is a composition that includes nanoparticles having a polymeric conjugate PLA-PEG-GL2 wherein the composition has less than about 10 ppm of palladium.

In an exemplary embodiment, a pharmaceutical composition is disclosed that includes a plurality of nanoparticles each comprising a therapeutic agent; about 0.1 to about 30 mole percent of the total polymer content, or about 0.1 to about 20 mole percent, or about 0.1 to about 10 mole percent, or about 1 to about 5 mole percent of the total polymer content of a nanoparticle, of a first macromolecule comprising a PLGA-PEG copolymer or PLA-PEG copolymer that is conjugated to ligand having a molecular weight between about 100 g/mol and 500 g/mol; and a second macromolecule comprising a PLGA-PEG copolymer or PLA-PEG copolymer, wherein the copolymer is not bound to a targeting moiety; and a pharmaceutically acceptable excipient. For example, the first copolymer may have about 0.001 and 5 weight percent of the ligand with respect to total polymer content.

In some embodiments, a composition suitable for freezing is comtemplated, including nanoparticles disclosed herein and a solution suitable for freezing, e.g. a sucrose solution is added to the nanoparticle suspension. The sucrose may e.g., as a cryoprotectant to prevent the particles from aggregating upon freezing. For example, provided herein is a nanoparticle formulation comprising a plurality of disclosed nanoparticles, sucrose and water; wherein the nanoparticles/sucrose/water is about 3-30%/10-30%/50-90% (w/w/w) or about 5-10%/10-15%/80-90% (w/w/w).

Methods of Treatment

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive targeted particles may be used to treat solid tumors, e.g., cancer and/or cancer cells. In certain embodiments, inventive targeted particles may be used to treat any cancer wherein PSMA is expressed on the surface of cancer cells or in the tumor neovasculature in a subject in need thereof, including the neovasculature of prostate or non-prostate solid tumors. Examples of the PSMA-related indication include, but are not limited to, prostate cancer, breast cancer, non-small cell lung cancer, colorectal carcinoma, and glioblastoma.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. prostate or breast cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. prostate cancer) is provided. In some embodiments, particles to a subject in such amounts and for such time as is necessary to achieve the desired result (i.e. treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the nanoparticles of the present invention can be used to inhibit the growth of cancer cells, e.g., prostate cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e. not as a disclosed nanoparticle).

EXAMPLES

The invention now being generally described, it will be more readily understood by reference to the following examples which are included merely for purposes of illustration of certain aspects and embodiments of the present invention, and are not intended to limit the invention in any way.

Example 1

Synthesis of a Low-Molecular Weight PSMA Ligand (GL2)

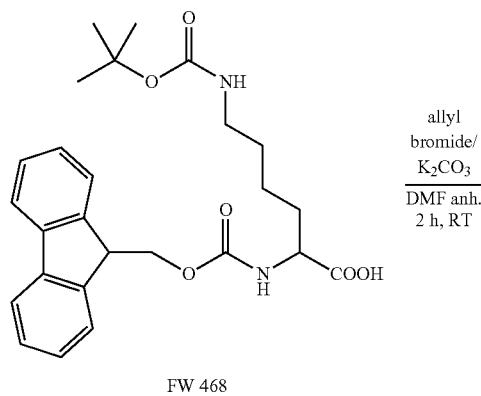

FW 468

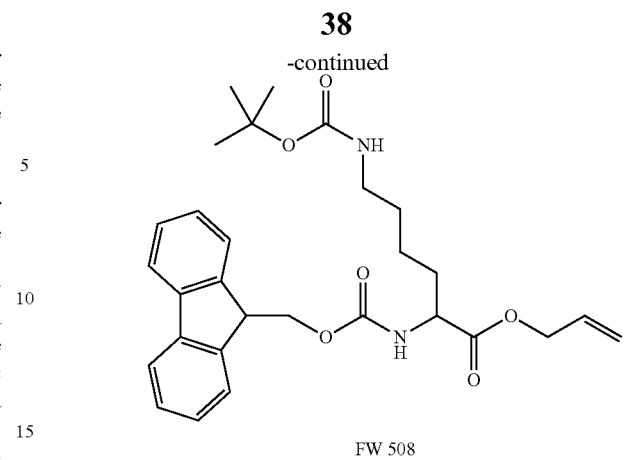

FW 508

5 g (10.67 mmol) of the starting compound was dissolved in 150 mL of anhydrous DMF. To this solution was added allyl bromide (6.3 mL, 72 mmol) and $K_2CO_3$ (1.47 g, 10.67 mmol). The reaction was stirred for 2 h, the solvent was removed, the crude material was dissolved in AcOEt and washed with $H_2O$ until pH neutral. The organic phase was dried with $MgSO_4$ (anhydrous) and evaporated to give 5.15 g (95%) of material. (TLC in $CH_2Cl_2$:MeOH 20:1 Rf=0.9, started compound Rf=0.1, revealed with ninhydrin and uv light).

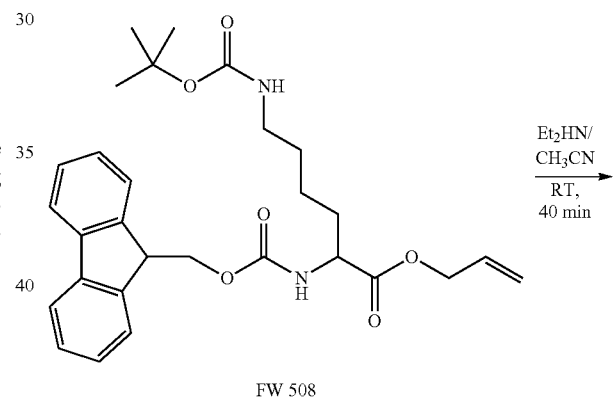

FW 508

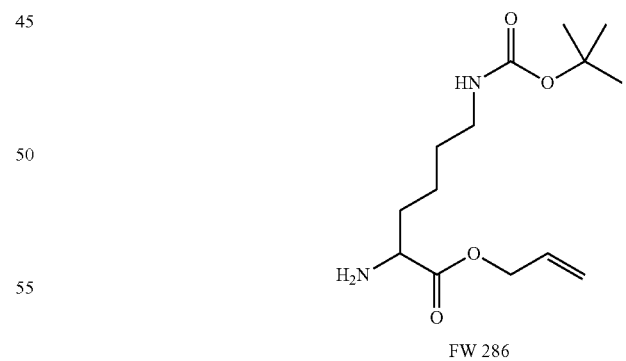

FW 286

To a solution of the compound (5.15 g, 10.13 mmol) in $CH_3CN$ (50 mL) was added $Et_2NH$ (20 mL, 0.19 mol). The reaction was stirred at room temperature for 40 min. The solvent was removed and the compound was purified by column chromatography (Hexane:AcOEt 3:2) to give 2.6 g (90%). (TLC in $CH_2Cl_2$:MeOH 10:1 Rf=0.4, revealed with ninhydrin (the compound has a violet color). $^1$H-NMR ($CDCl_3$, 300 MHz) δ 5.95-5.85 (m, 1H, —$CH_2CHCH_2$), 5.36-5.24 (m, 2H, —CH$_2$CHCH$_2$), 4.62-4.60 (m, 3H, —CH$_2$CHCH$_2$, NHBoc), 3.46 (t, 1H, CH(Lys)), 3.11-3.07 (m, 2H, CH$_2$NHBoc), 1.79 (bs, 2H, NH$_2$), 1.79-1.43 (m, 6H, 3CH$_2$(Lys)), 1.43 (s, 9H, Boc).

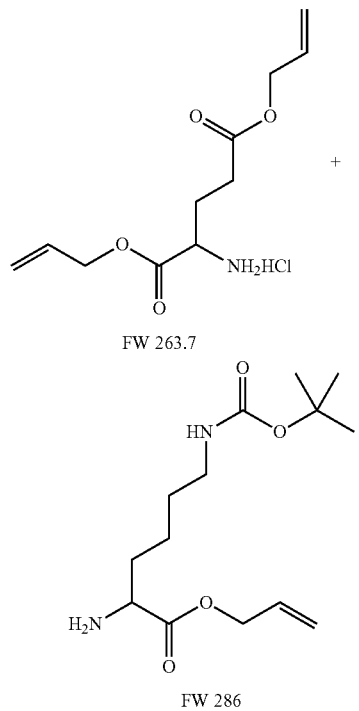

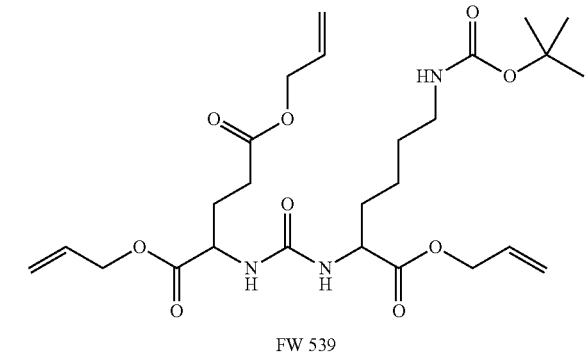

To a stirred solution of diallyl glutamate (3.96 g, 15 mmol) and triphosgene (1.47 g, 4.95 mmol) in CH$_2$Cl$_2$(143 mL) at −78° C. was added Et$_3$N (6.4 mL, 46 mmol) in CH$_2$Cl$_2$(28 mL). The reaction mixture was allowed to warm to room temperature and stirred for 1.5 h. The Lysine derivative (2.6 g, 9.09 mmol) in a solution of CH$_2$Cl$_2$ (36 mL) was then added at −78° C. and the reaction was stirred at room temperature for 12 h. The solution was diluted with CH$_2$Cl$_2$, washed twice with H$_2$O, dried over MgSO$_4$ (anh.) and purified by column chromatography (Hexane:AcOEt 3:1→2:1→AcOEt) to give 4 g (82%) (TLC in CH$_2$Cl$_2$:MeOH 20:1 Rf=0.3, revealed with ninhydrin). $^1$H-NMR (CDCl$_3$, 300 MHz) δ 5.97-5.84 (m, 3H, 3-CH$_2$CHCH$_2$), 5.50 (bt, 2H, 2NHurea), 5.36-5.20 (m, 6H, 3-CH$_2$CHCH$_2$), 4.81 (bs, 1H, NHBoc), 4.68-4.40 (m, 8H, 3-CH$_2$CHCH$_2$, CH(Lys), CH(glu)), 3.09-3.05 (m, 2H, CH$_2$NHBoc), 2.52-2.39 (m, 2H, CH$_2$(glu.)), 2.25-2.14 and 2.02-1.92 (2m, 2H, CH$_2$(glu.)), 1.87-1.64 (m, 4H, 2CH$_2$(Lys)), 1.51-1.35 (m, 2H, CH$_2$(Lys)), 1.44 (s, 9H, Boc).

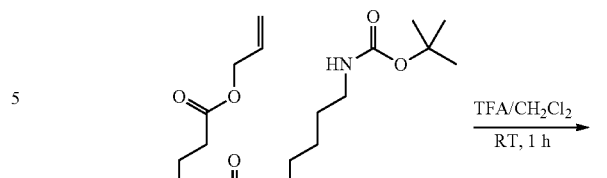

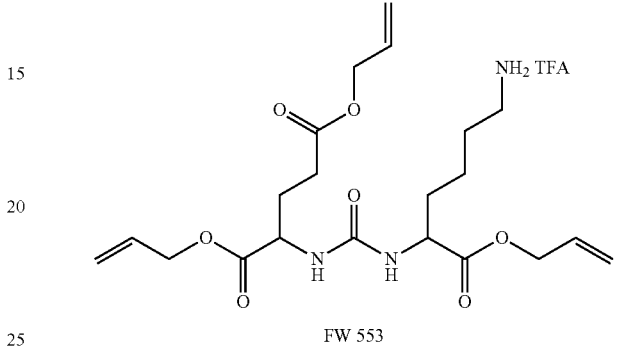

To a solution of the compound (4 g, 7.42 mmol) in dry CH$_2$Cl$_2$ (40 mL) was added at 0° C. TFA (9 mL). The reaction was stirred at room temperature for 1 h. The solvent was removed under vacuum until complete dryness, to give 4.1 g (quantitative). (TLC in CH$_2$Cl$_2$:MeOH 20:1 Rf=0.1, revealed with ninhydrin). $^1$H-NMR (CDCl$_3$, 300 MHz) δ 6.27-6.16 (2d, 2H, 2NHurea), 5.96-5.82 (m, 3H, 3-CH$_2$CHCH$_2$), 5.35-5.20 (m, 6H, 3-CH$_2$CHCH$_2$), 4.61-4.55 (m, 6H, 3-CH$_2$CHCH$_2$), 4.46-4.41 (m, 2H, CH(Lys), CH(glu)), 2.99 (m, 2H, CH$_2$NHBoc), 2.46 (m, 2H, CH$_2$(glu.)), 2.23-2.11 and 2.01-1.88 (2 m, 2H, CH$_2$(glu.)), 1.88-1.67 (m, 4H, 2CH$_2$(Lys)), 1.45 (m, 2H, CH$_2$(Lys)).

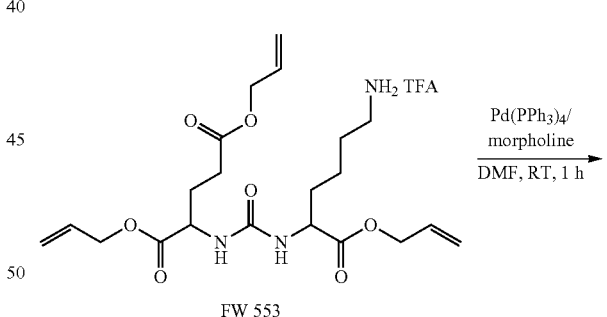

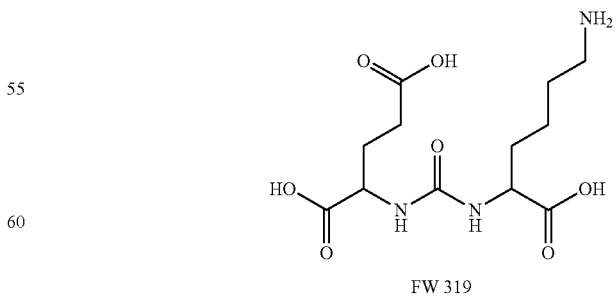

To a solution of the compound (2 g, 3.6 mmol) in DMF (anh.) (62 mL) under argon was added Pd(PPh$_3$)$_4$ (0.7 g, 0.6 mmol) and morpholine (5.4 mL, 60.7 mmol) at 0° C. The reaction was stirred at room temperature for 1 h. The solvent was removed. The crude product was washed twice with CH$_2$Cl$_2$, and then solved in H$_2$O. To this solution was added a diluted solution of NaOH (0.01 N) until the pH was very basic. The solvent was removed under reduced pressure. The solid was washed again with CH$_2$Cl$_2$, AcOEt, and a mixture of MeOH—CH$_2$Cl$_2$ (1:1), solved in H$_2$O and neutralized with Amberlite IR-120 H$^+$ resin. The solvent was evaporated, and the compound was precipitated with MeOH, to give 1 g (87%) of GL2. $^1$H-NMR (D$_2$O, 300 MHz) δ 4.07 (m, 2H, CH(Lys), CH(glu)), 2.98 (m, 2H, CH$_2$NH$_2$), 2.36 (m, 2H, CH$_2$(glu.)), 2.08-2.00 (m, 1H, CH$_2$(glu)), 1.93-1.60 (m, 5H, CH$_2$(glu.), 2CH$_2$(Lys)), 1.41 (m, 2H, CH$_2$(Lys)). Mass ESI: 320.47 [M+H$^+$], 342.42 [M+Na$^+$].

Example 2

Synthesis of a Low-Molecular Weight PSMA Ligand (GL1)

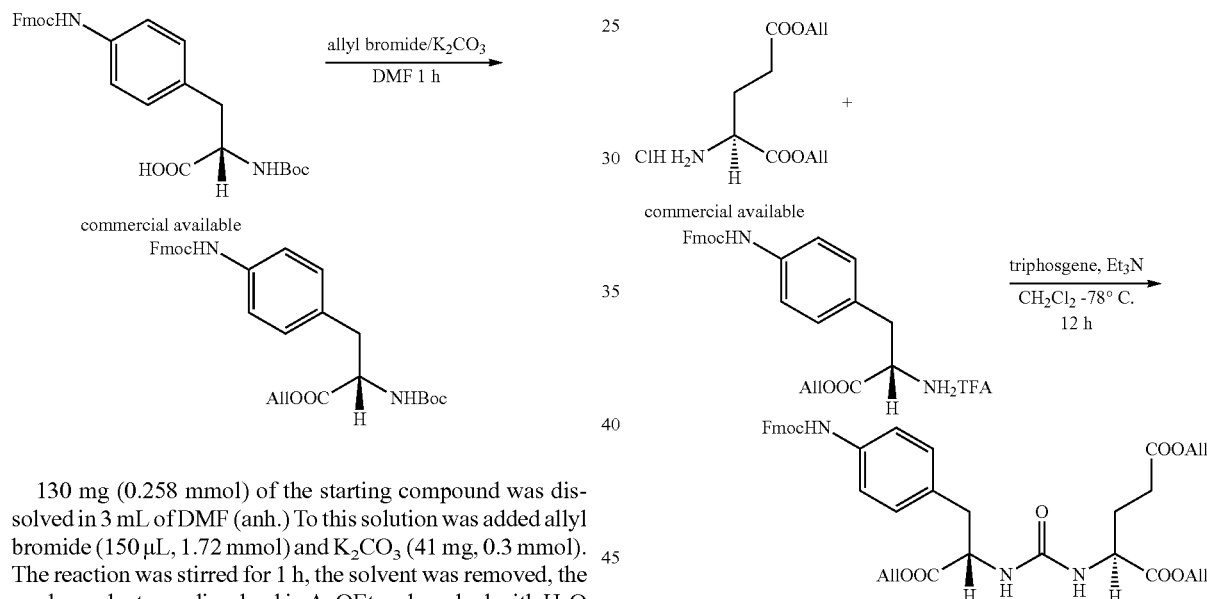

130 mg (0.258 mmol) of the starting compound was dissolved in 3 mL of DMF (anh.) To this solution was added allyl bromide (150 μL, 1.72 mmol) and K$_2$CO$_3$ (41 mg, 0.3 mmol). The reaction was stirred for 1 h, the solvent was removed, the crude product was dissolved in AcOEt and washed with H$_2$O until pH neutral. The organic phase was dried with MgSO$_4$ (anh.) and evaporated to give 130 mg (93%). (TLC in CH$_2$Cl$_2$:MeOH 20:1 Rf=0.9, started compound Rf=0.1, revealed with ninhydrin and uv light). $^1$H-NMR (CDCl$_3$, 300 MHz) δ 7.81-7.05 (12H, aromatics), 6.81 (bs, 1H, NHFmoc), 5.93-5.81 (m, 1H, —CH$_2$CHCH$_2$), 5.35-5.24 (m, 2H, —CH$_2$CHCH$_2$), 5.00 (bd, 1H, NHboc), 4.61-4.53 (m, 5H, —CH$_2$CHCH$_2$, CH$_2$(Fmoc), CH(pheala.)), 4.28 (t, 1H, CH(Fmoc)), 3.12-2.98 (m, 2H, CH$_2$(pheala.), 1.44 (s, 9H, Boc).

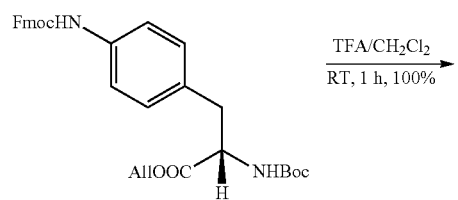

To a solution of the compound (120 mg, 0.221 mmol) in dry CH$_2$Cl$_2$ (2 mL) was added at 0° C. TFA (1 mL). The reaction was stirred at room temperature for 1 h. The solvent was removed under vacuum, water was added and removed again, CH$_2$Cl$_2$ was added and removed again until complete dryness to give 120 mg (quantitative). (TLC in CH$_2$Cl$_2$:MeOH 20:1 Rf=0.1, revealed with ninhydrin and uv light). $^1$H-NMR (CDCl$_3$, 300 MHz) δ 7.80-7.00 (13H, aromatics, NHFmoc), 5.90-5.75 (m, 1H, —CH$_2$CHCH$_2$), 5.35-5.19 (m, 3H, —CH$_2$CHCH$_2$, NHboc), 4.70-4.40 (2m, 5H, —CH$_2$CHCH$_2$, CH$_2$(Fmoc), CH(pheala.)), 4.20 (t, 1H, CH(Fmoc)), 3.40-3.05 (m, 2H, CH$_2$(pheala.)).

To a stirred solution of diallyl glutamate (110 mg, 0.42 mmol) and triphosgene (43 mg, 0.14 mmol) in CH$_2$Cl$_2$ (4 mL) at −78° C. was added Et$_3$N (180 μL, 1.3 mmol) in CH$_2$Cl$_2$ (0.8 mL). The reaction mixture was allowed to warm to room temperature and stirred for 1.5 h. The phenylalanine derivative (140 mg, 0.251 mmol) in a solution of CH$_2$Cl$_2$ (1 mL) and Et$_3$N (70 μL, 0.5 mmol) was then added at −78° C. and the reaction was stirred at room temperature for 12 h. The solution was diluted with CH$_2$Cl$_2$, washed twice with H$_2$O, dried over MgSO$_4$ (anh.) and purified by column chromatography (Hexane:AcOEt 3:1) to give 100 mg (57%) (TLC in CH$_2$Cl$_2$:MeOH 20:1 Rf=0.3, revealed with ninhydrin and uv light). $^1$H-NMR (CDCl$_3$, 300 MHz) δ 7.80-6.95 (13H, aromatics, NHFmoc), 5.98-5.82 (m, 3H, 3-CH$_2$CHCH$_2$), 5.54 (bd, 1H, NHurea), 5.43-5.19 (m, 7H, 3-CH$_2$CHCH$_2$, NHurea), 4.85-4.78 (m, 1H, CH(pheala.)), 4.67-4.50 (m, 9H, 3-CH$_2$CHCH$_2$, CH$_2$(Fmoc), CH(glu.)), 4.28 (t, 1H, CH(Fmoc)), 3.05 (d, 2H, CH$_2$(pheala.)), 2.53-2.33 (m, 2H, CH$_2$(glu.)), 2.25-2.11 and 1.98-1.80 (2m, 2H, CH$_2$(glu.)).

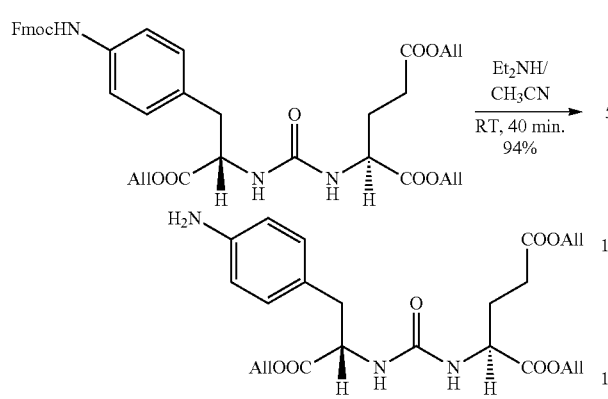

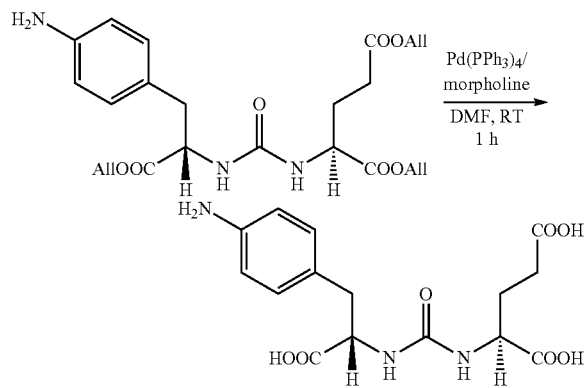

To a solution of the starting material (60 mg, 0.086 mmol) in CH$_3$CN (1 mL) was added Et$_2$NH (1 mL, 10 mmol). The reaction was stirred at room temperature for 40 min. The solvent was removed and the compound was purified by column chromatography (Hexane:AcOEt 2:1) to give 35 mg (85%). (TLC in CH$_2$Cl$_2$:MeOH 10:1 Rf=0.5, started compound Rf=0.75, revealed with ninhydrin (the compound has a violet color) and uv light). $^1$H-NMR (CDCl$_3$, 300 MHz) δ 6.85 and 6.55 (2d, 4H, aromatics), 5.98-5.82 (m, 3H, 3-CH$_2$CHCH$_2$), 5.56 (bd, 1H, NHurea), 5.44-5.18 (m, 7H, 3-CH$_2$CHCH$_2$, NHurea), 4.79-4.72 (m, 1H, CH(pheala.)), 4.65-4.49 (m, 7H, 3-CH$_2$CHCH$_2$, CH(glu.)), 3.64 (bs, 2H, NH$_2$), 3.02-2.89 (m, 2H, CH$_2$(pheala.)), 2.49-2.31 (m, 2H, CH$_2$(glu.)), 2.20-2.09 and 1.91-1.78 (2m, 2H, CH$_2$(glu.)).

To a solution of the compound (50 mg, 0.105 mmol) in DMF (anh.; 1.5 mL) under argon was added Pd(PPh$_3$)$_4$ (21 mg, 0.018 mmol) and morpholine (154 μL, 1.77 mmol) at 0° C. The reaction was stirred at room temperature for 1 h. The solvent was removed. The crude material was washed with CH$_2$Cl$_2$ twice, and dissolved in H$_2$O. To this solution was added a diluted solution of NaOH (0.01 N) until the pH was very basic. The solvent was removed under reduced pressure. The solid was washed again with CH$_2$Cl$_2$, AcOEt, and mixture of MeOH—CH$_2$Cl$_2$ (1:1), solved in H$_2$O and neutralized with Amberlite IR-120 H$^+$ resin. The solvent was evaporated and the compound was precipitated with MeOH, to give 25 mg (67%) of GL1. $^1$H-NMR (D$_2$O, 300 MHz) δ 7.08 and 6.79 (2d, 4H, aromatics), 4.21 (m, 1H, CH(pheala.)), 3.90 (m, 1H, CH(glu.)), 2.99 and 2.82 (2dd, 2H, CH$_2$(pheala.)), 2.22-2.11 (m, 2H, CH$_2$(glu.)), 2.05-1.70 (2m, 2H, CH$_2$(glu.)). $^{13}$C-NMR (D$_2$O, 75 MHz) δ 176.8, 174.5, 173.9 (3 COO), 153.3 (NHCONH), 138.8 (H$_2$N—C(Ph)), 124.5, 122.9, 110.9 (aromatics), 51.3 (CH(pheala.)), 49.8 (CH(glu.)), 31.8 (CH$_2$(pheala.)), 28.4 and 23.6 (2CH$_2$-glu.)). Mass ESI: 354.19 [M+H$^+$], 376.23 [M+Na$^+$].

Example 3

Preparation of PLA-PEG

The synthesis is accomplished by ring opening polymerization of d,l-lactide with α-hydroxy-ω-methoxypoly(ethylene glycol) as the macro-initiator, and performed at an elevated temperature using Tin (II) 2-Ethyl hexanoate as a catalyst, as shown below(PEG Mn≈5,000 Da; PLA Mn≈16,000 Da; PEG-PLA M$_n$≈21,000 Da)

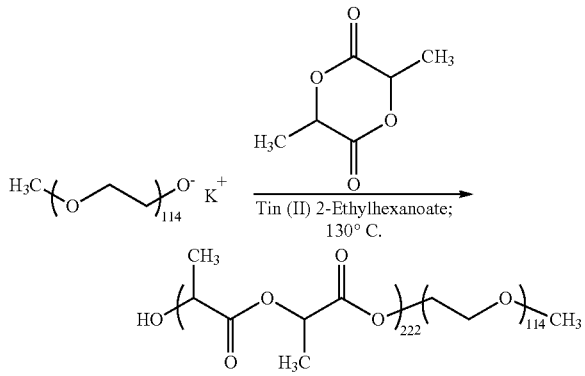

The polymer is purified by dissolving the polymer in dichloromethane, and precipitating it in a mixture of hexane and diethyl ether. The polymer recovered from this step shall be dried in an oven.

Example 4

PLA-PEG-Ligand Preparation

Figure 2:
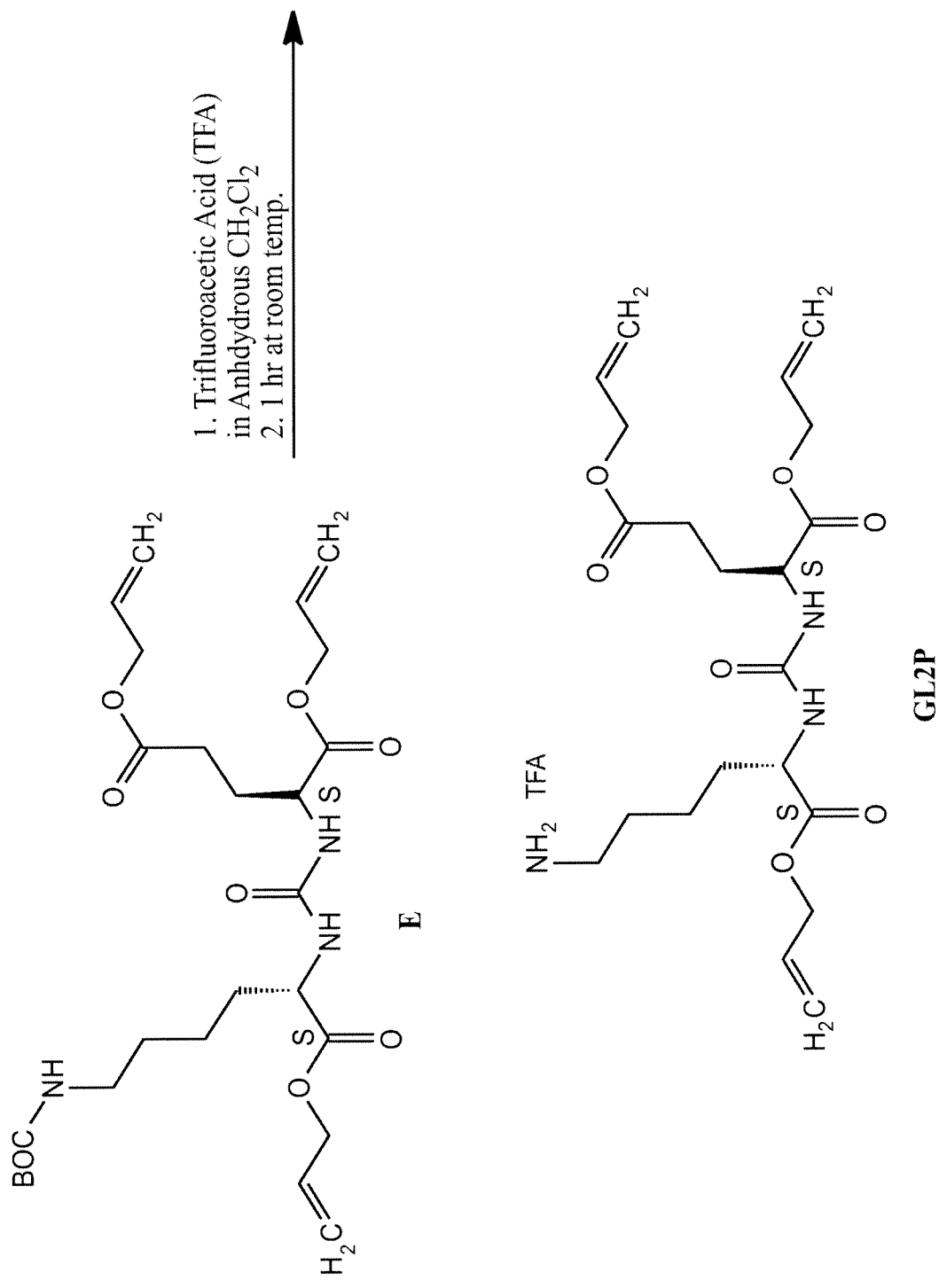
FIG. 2 depicts an exemplary synthetic scheme to a disclosed nanoparticle.
Figure 2:
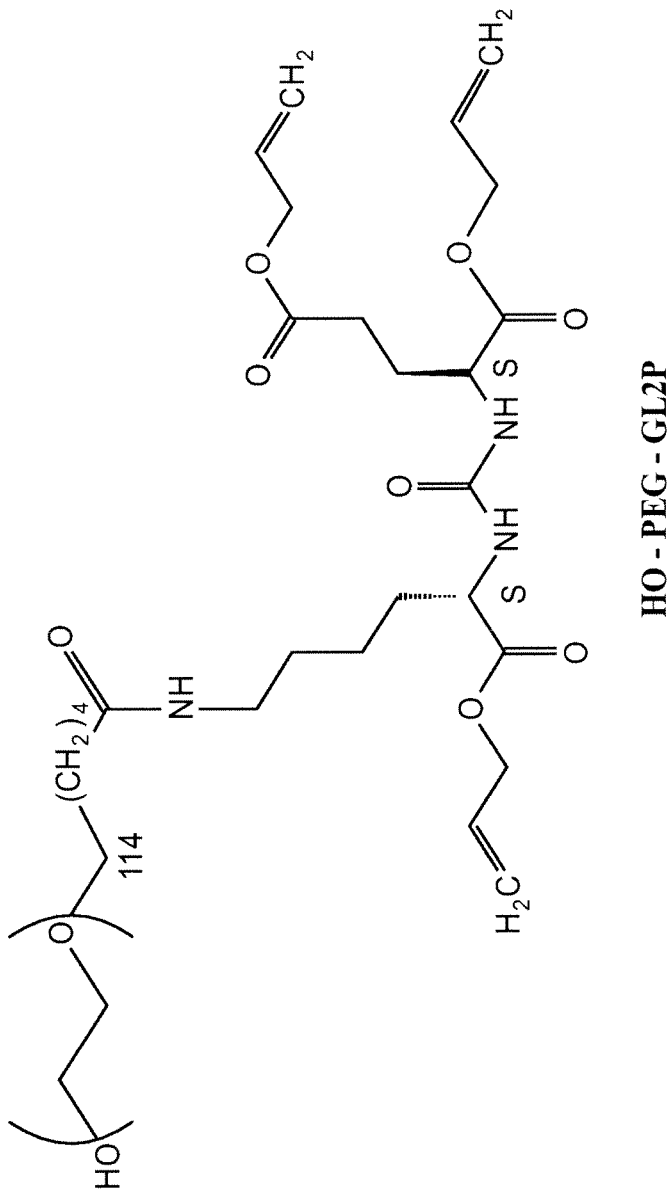
Figure 2:
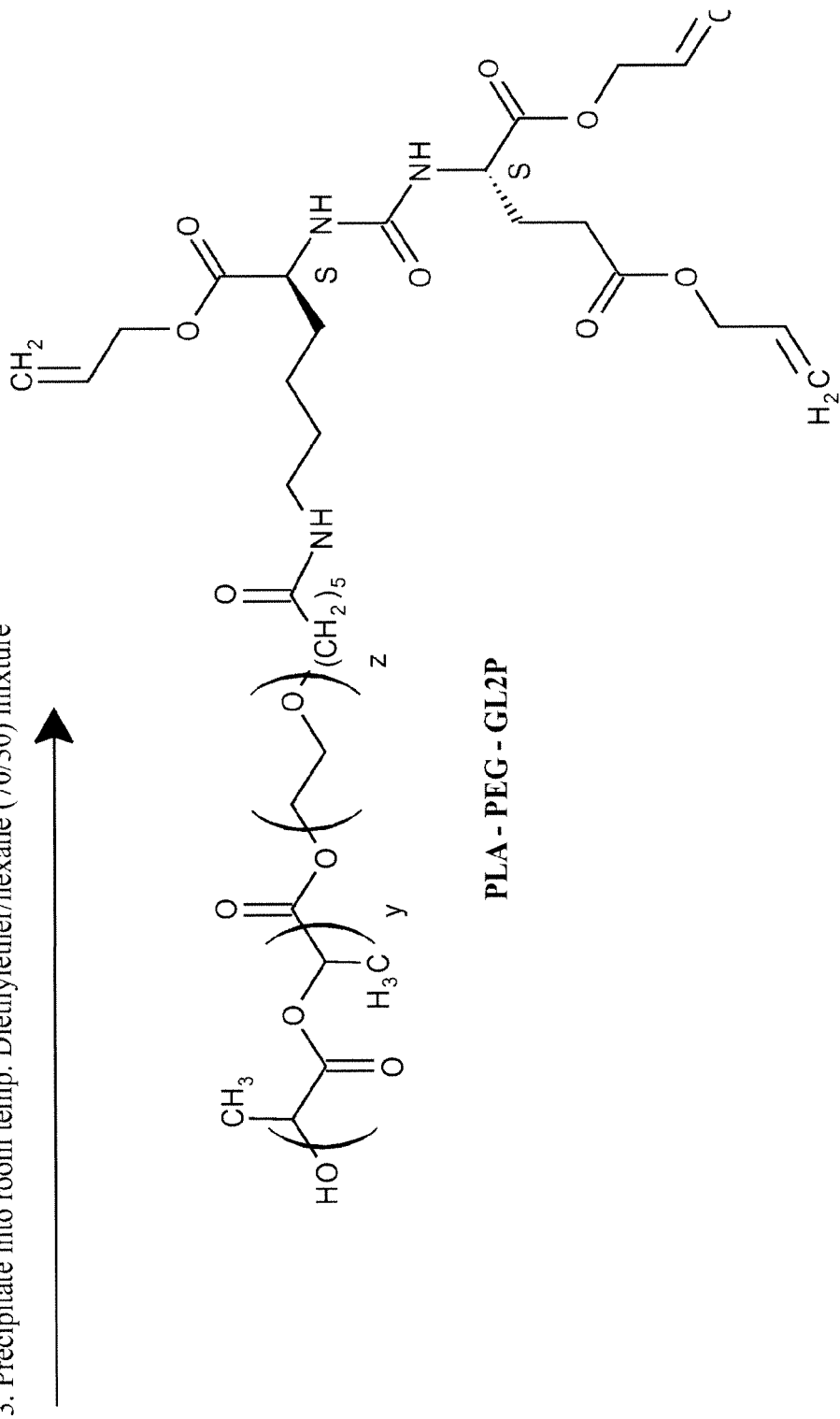
Figure 2:
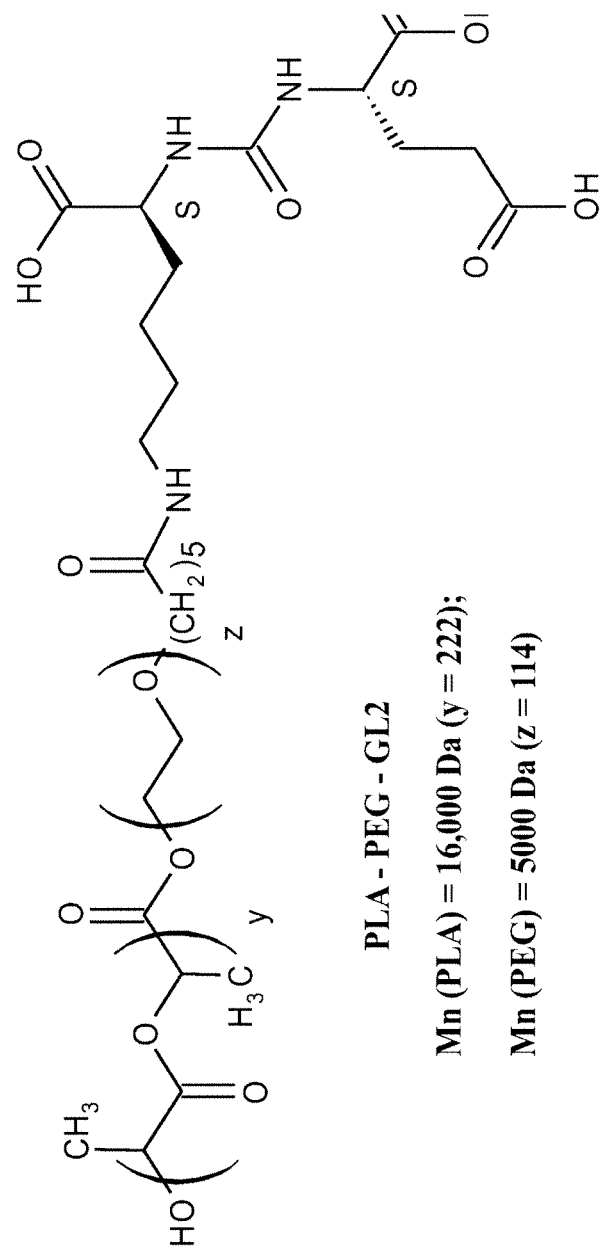

The synthesis, shown in FIG. 2, starts with the conversion of FMOC, BOC lysine to FMOC, BOC, Allyl lysine by reacting the FMOC, BOC lysine with allyl bromide and potassium carbonate in dimethyl formamide, followed by treatment with diethyl amine in acetonitrile. The BOC, Allyl lysine is then reacted with triphosgene and diallyl glutamate, followed by treatment with trifluoracetic acid in methylene chloride to form the compound "GL2P".

The side chain amine of lysine in the GL2P is then pegylated by the addition of Hydroxyl-PEG-Carboxlyic acid with EDC and NHS. The conjugation of GL2P to PEG is via an amide linkage. The structure of this resulting compound is labeled "HO-PEG-GL2P". Following the pegylation, ring opening polymerization (ROP) of d,l-lactide with the hydroxyl group in the HO-PEG-GL2P as initiator is used to attach a polylactide block polymer to HO-PEG-GL2P via an ester bond yielding "PLA-PEG-GL2P". Tin (II) 2-Ethyl hexanoate is used as a catalyst for the ring opening polymerization.

Lastly, the allyl groups on the PLA-PEG-GL2P are removed using morpholine and tetrakis(triphenylphosphine) palladium (as catalyst) in dichloromethane, to yield the final product PLA-PEG-Ligand. The final compound is purified by precipitation in 30/70% (v/v) diethyl ether/hexane.

Example 5

Nanoparticle Preparation-Nanoprecipitation

Nanoparticles can be prepared using GL1 or GL2 ligand. The urea-based PSMA inhibitor GL2, which has a free amino group located in a region not critical for PSMA binding, is synthesized from commercially available starting materials Boc-Phe(4NHFmoc)-OH and diallyl glutamic acid in accordance with the procedure shown in Scheme 1. Nanoparticles are formed using nanoprecipitation: The polymer ligand conjugate is dissolved in a water miscible organic solvent together with a drug other agent for tracking particle uptake. Additional non-functionalized polymer can be included to modulate the ligand surface density. The polymer solution is dispersed in an aqueous phase and the resulting particles are collected by filtration. The particles can be dried or immediately tested for cell uptake in vitro or anti-prostate tumor activity in vivo.

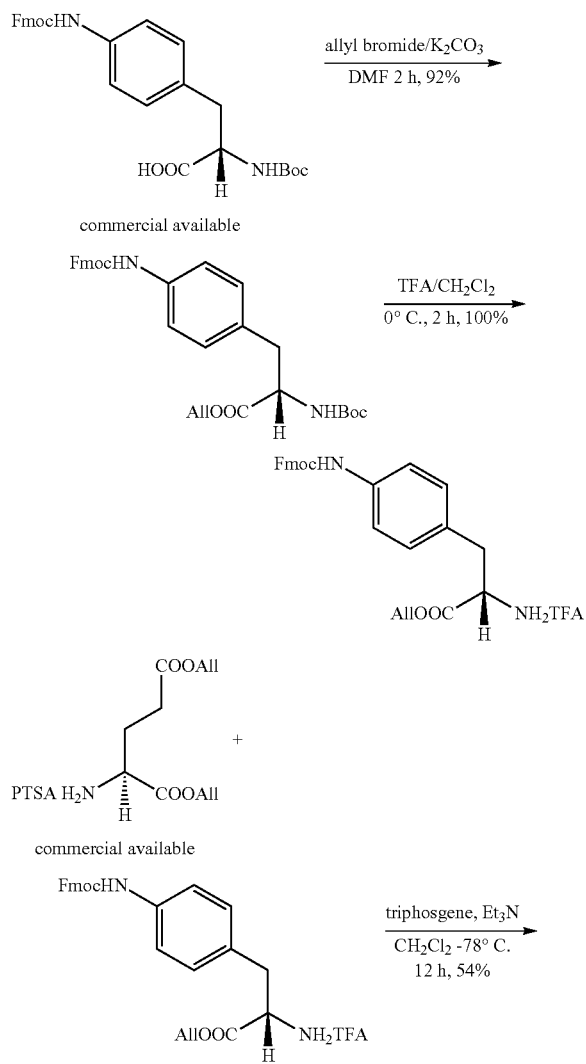

Scheme 1

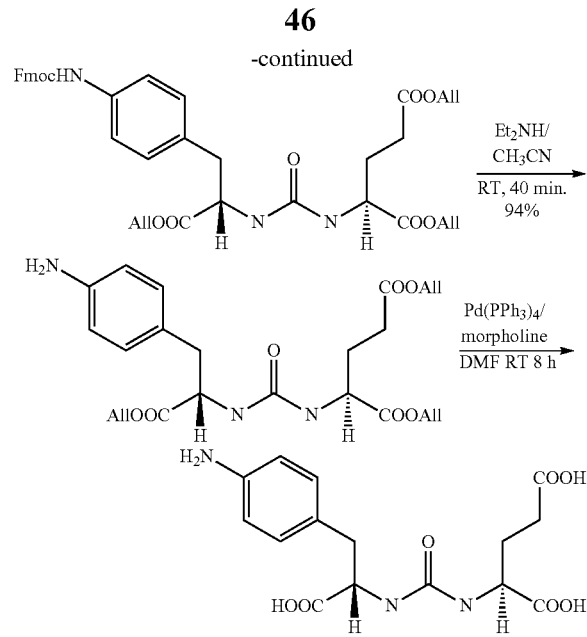

Example 6

Nanoparticle Preparation—Emulsion Process

An organic phase is formed composed of 5% solids (wt %) including 2% poly(lactide-co-glycolide)-poly(ethylene glycol) diblock copolymer (PLGA-PEG; 45 kDa-5 kDa), 2% poly(D,L-lactide) (PLA; 8.5 kDa), and 1% docetaxel (DTXL) wherein docetaxel has the structure

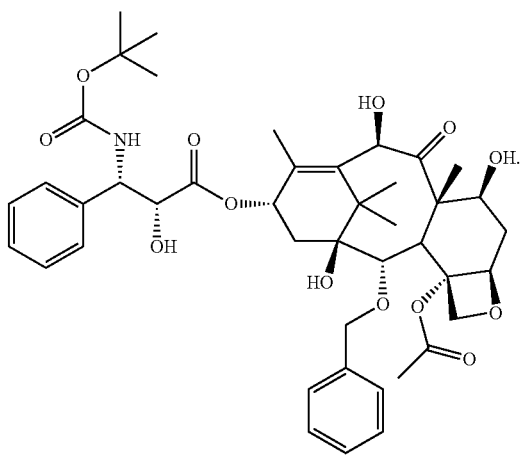 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OCc4ccccc4)C12)C3(C)C]

The organic solvents are ethyl acetate (EA) and benzyl alcohol (BA) where BA comprises 20% (wt %) of the organic phase. BA is used in part to solublize the docetaxel. The organic phase is mixed with an aqueous phase at approximately a 1:5 ratio (oil phase:aqueous phase) where the aqueous phase is composed of 0.5% sodium cholate, 2% BA, and 4% EA (wt %) in water. The primary emulsion is formed by the combination of the two phases under simple mixing or through the use of a rotor stator homogenizer. The primary emulsion is then formed into a fine emulsion through the use of a probe sonicator or a high pressure homogenizer.

The fine emulsion is then quenched by addition to a chilled quench (0-5° C.) of deionized water under mixing. The quench:emulsion ratio is approximately 8.5:1. Then a solution of 25% (wt %) of Tween 80 is added to the quench to achieve approximately 2% Tween 80 overall. The nanoparticles are then isolated through either centrifugation or ultrafiltration/diafiltration. The nanoparticle suspension may then be frozen with a cyroprotectant, such as 10 wt % sucrose.

The addition of PLA in addition to the PLGA-PEG copolymer was found to significantly increase the drug load. It is possible the use of BA itself also serves to increase the encapsulation efficiency as well, increasing the encapsulation efficiency even if the BA was not required to solubilize the DTXL. The temperature of the quench was found to play a critical role in drug loading. The use of a cold quench (generally maintained at 0-5° C.) significantly increased the drug loading compared to the drug loading when a room temperature quench was used.

DTXL has very low water solubility, and it was found that unencapsulated DTXL often formed crystals which were difficult to isolate from the formed nanoparticles. Drug solubilizer (Tween 80) was added after the fine emulsion has been quenched. Tween 80 is able to effectively solubilize DTXL crystals and allow for the isolation of nanoparticles from unencapsulated DTXL by preventing the formation of DTXL crystals, and/or by effectively solubilizing any DTXL crystals that formed when the fine emulsion is quenched A standard set of nanoemulsion conditions were as follows:
Control:

| Attribute | Value |
| --- | --- |
| Block copolymer (type/amount) | 45/5 PLGA (50/50 L:G)-PEG (5 kDa), 80% |
| Homopolymer (type/amount) | None |
| Drug (amount DTXL) | 10% |
| Organic solvent (type/amount) | Ethyl acetate (EA) |
| Organic cosolvent (type/amount) | None |
| Water phase | 1% PVA with 6.5% EA |
| Quench temperature | ~5° C. |
| RESULTS | |
| Particle size | 191 nm |
| Drug load | 0.8% |
| In vitro release (24 hour at 37 C.) | Not determined (ND) |
| Other | NA |

The addition of homopolymer as an additive yielded increased drug load while particle size is decreased, as shown below:

| Attribute | Control value | Example value |
| --- | --- | --- |
| Block copolymer (type/amount) | 45/5 PLGA (50/50 L:G)-PEG (5 kDa), 90% | 45/5 PLGA (50/50 L:G)-PEG (5 kDa), 45% |
| Homopolymer (type/amount) | None | 8.5 kDa PLA, 45% |
| Drug (amount DTXL) | 10% | 10% |
| Organic solvent (type/amount) | EA | EA, 80% |
| Organic cosolvent (type/amount) | None | Benzyl alcohol (BA), 20% |
| Water phase | 1% PVA with 6.5% EA | 1% PVA with 6.5% EA |
| Quench temperature | ~5° C. | ~5° C. |
| RESULTS | | |
| Particle size | 191 nm | 134 nm |
| Drug load | 0.8% | 2.4% |
| In vitro release (24 hour at 37 C.) | Not determined (ND) | Not determined (ND) |
| Other | NA | NA |

Quench Temperature

Here the control used for comparison is different from the control above, as those were already performed at cold quench temperature.

| Attribute | Control value | Example value |
| --- | --- | --- |
| Block copolymer (type/amount) | 45/5 PLGA (50/50 L:G)-PEG (5 kDa), 47.5% | 45/5 PLGA (50/50 L:G)-PEG (5 kDa), 47.5% |
| Homopolymer (type/amount) | ~30 kDa PLGA (50/50 L:G), 47.5% | ~30 kDa PLGA (50/50 L:G), 47.5% |
| Drug (amount DTXL) | 5% | 5% |
| Organic solvent (type/amount) | Dichloromethane (DCM) | Dichloromethane (DCM) |
| Organic cosolvent (type/amount) | None | None |
| Water phase | 0.5% sodium cholate | 0.5% sodium cholate |
| Quench temperature | ~25° C. | ~5° C. |
| RESULTS | | |
| Particle size | 210 nm | 214 nm |
| Drug load | 1.2% | 3.6% |
| In vitro release (24 hour at 37 C.) | Not determined (ND) | Not determined (ND) |
| Other | NA | NA |

Exemplary Parameters

| Attribute | Value |
| --- | --- |
| Block copolymer (type/amount) | 45/5 PLA-PEG, 40% (5 mol % containing PLA-PEG-GL2) |
| Homopolymer (type/amount) | 8.5 kDa PLA, 40% |
| Drug (amount DTXL) | 20% |
| Organic solvent (type/amount) | EA, 80% |
| Organic cosolvent (type/amount) | BA, 20% |
| Water phase | 0.5% sodium cholate, 4% EA, 2% BA |
| Quench temperature | ~5° C. |
| RESULTS | |
| Particle size | 98.5 nm |
| Drug load | 3.0% |
| In vitro release (24 hour at 37 C.) | ~60% |

Example 7

Emulsion Process

The process described below uses an increase in the solids content of the oil phase. A general flow chart of the process is depicted in FIG. 3, and a process flow diagram is depicted in FIG. 4. By reducing the solvent content of the emulsified oil phase, less drug is lost to the quench fluid when the nanoparticles are hardened. A solids and solvent system are chosen to avoid being overly viscous, which may limit the ability to emulsify into ~100 nm droplets. The use of a relatively low molecular weight copolymer (PLA-PEG of ~16 kDa-5 kDa) and low molecular weight homopolymer (PLA of ~7 kDa) allows the formulation to remain of low enough viscosity at high solids content. A solvent system is chosen having a suitable solvating power to keep the drug in solution at high concentrations. Use of a co-solvent system (typically 79:21 ethyl acetate:benzyl alcohol) allows for a continuous solution up to 50% solids with an 80:20 polymer:docetaxel blend.

An organic phase is formed composed of a mixture of docetaxel (DTXL) and polymer (homopolymer, co-polymer, and co-polymer with ligand). The organic phase is mixed with an aqueous phase at approximately a 1:5 ratio (oil phase:

aqueous phase) where the aqueous phase is composed of a surfactant and some dissolved solvent. In order to achieve high drug loading, about 30% solids in the organic phase is used.

An organic phase is formed composed of a mixture of docetaxel (DTXL) and polymer (homopolymer, co-polymer, and co-polymer with ligand). Compositions and organic solvents are listed on the table. The organic phase is mixed with an aqueous phase at approximately a 1:5 ratio (oil phase: aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water at a given temperature (listed on table) under mixing. The quench:emulsion ratio is approximately 8.5:1. Then a solution of 25% (wt %) of Tween 80 is added to the quench to achieve approximately 2% Tween 80 overall. This serves to dissolve free, unencapsulated drug, and makes the nanoparticle isolation process feasible. The nanoparticles are then isolated through either centrifugation or ultrafiltration/diafiltration.

Control

A standard set of nanoemulsion conditions are provided as follows. Non-ligand containing particles (non-targeted nanoparticles) are formed.

| Attribute | Value |
| --- | --- |
| Lot # | 15-157D |
| Homopolymer (type/amount) | 6.5 kDa PLA |
| Copolymer (type/amount) | 16/5 PLA-PEG, 40% |
| Drug (amount DTXL) | 20% |
| Organic solvent (type/amount) | Ethyl acetate (EA), 79% |
| Organic cosolvent (type/amount) | Benzyl alcohol (BA), 21% |
| Water phase | 0.5% sodium cholate, 2% BA, 4% EA in water |
| [solids] in oil phase | 5 wt % |
| RESULTS | |
| Particle size | 114.7 nm |
| Drug load | 3.97% |

10% Solids

| Attribute | Control value | Example value |
| --- | --- | --- |
| Lot # | 15-157D | 15-157C |
| Homopolymer (type/amount) | 6.5 kDa PLA | 6.5 kDa PLA |
| Copolymer (type/amount) | 16/5 PLA-PEG, 40% | 16/5 PLA-PEG, 40% |
| Drug (amount DTXL) | 20% | 20% |
| Organic solvent (type/amount) | Ethyl acetate (EA), 79% | Ethyl acetate (EA), 79% |
| Organic cosolvent (type/amount) | Benzyl alcohol (BA), 21% | Benzyl alcohol (BA), 21% |
| Water phase | 0.5% sodium cholate, 2% BA, 4% EA in water | 0.5% sodium cholate, 2% BA, 4% EA in water |
| [solids] in oil phase | 5 wt % | 10 wt % |
| RESULTS | | |
| Particle size | 114.7 nm | 115.1 nm |
| Drug load | 3.97% | 13.36% |

20% Solids

| Attribute | Control value | Example value |
| --- | --- | --- |
| Lot # | 15-157D | 15-157A |
| Homopolymer (type/amount) | 6.5 kDa PLA | 6.5 kDa PLA |
| Copolymer (type/amount) | 16/5 PLA-PEG, 40% | 16/5 PLA-PEG, 40% |
| Drug (amount DTXL) | 20% | 20% |
| Organic solvent (type/amount) | Ethyl acetate (EA), 79% | Ethyl acetate (EA), 79% |
| Organic cosolvent (type/amount) | Benzyl alcohol (BA), 21% | Benzyl alcohol (BA), 21% |
| Water phase | 0.5% sodium cholate, 2% BA, 4% EA in water | 0.5% sodium cholate, 2% BA, 4% EA in water |
| [solids] in oil phase | 5 wt % | 20 wt % |
| RESULTS | | |
| Particle size | 114.7 nm | 130.3 nm |
| Drug load | 3.97% | 16.15% |

40% Solids

| Attribute | Control value | Example value |
| --- | --- | --- |
| Lot # | 15-157D | 15-171A |
| Homopolymer (type/amount) | 6.5 kDa PLA | 6.5 kDa PLA |
| Copolymer (type/amount) | 16/5 PLA-PEG, 40% | 16/5 PLA-PEG, 40% |
| Drug (amount DTXL) | 20% | 20% |
| Organic solvent (type/amount) | Ethyl acetate (EA), 79% | Ethyl acetate (EA), 79% |
| Organic cosolvent (type/amount) | Benzyl alcohol (BA), 21% | Benzyl alcohol (BA), 21% |
| Water phase | 0.5% sodium cholate, 2% BA, 4% EA in water | 0.5% sodium cholate, 2% BA, 4% EA in water |
| [solids] in oil phase | 5 wt % | 40 wt % |
| RESULTS | | |
| Particle size | 114.7 nm | 130 nm |
| Drug load | 3.97% | 14.07% |

30% Solids with Higher Surfactant Concentration for Particle Size Reduction; Targeted Nanoparticle Batch.

| Attribute | Control value | Example value |
| --- | --- | --- |
| Lot # | 15-157D | 35-03A |
| Homopolymer (type/amount) | 6.5 kDa PLA | 8.2 kDa PLA |
| Copolymer (type/amount) | 16/5 PLA-PEG, 40% | 16/5 PLA-PEG, 40%, with 1 wt % as GL2-PEG-PLA |
| Drug (amount DTXL) | 20% | 20% |
| Organic solvent (type/amount) | Ethyl acetate (EA), 79% | Ethyl acetate (EA), 79% |
| Organic cosolvent (type/amount) | Benzyl alcohol (BA), 21% | Benzyl alcohol (BA), 21% |
| Water phase | 0.5% sodium cholate, 2% BA, 4% EA in water | 1% sodium cholate, 2% BA, 4% EA in water |
| [solids] in oil phase | 5 wt % | 30 wt % |
| RESULTS | | |
| Particle size | 114.7 nm | 114.1 nm |
| Drug load | 3.97% | 11.85% |

Example 8

Nanoparticle Preparation—Emulsion Process 2

An organic phase is formed composed of a mixture of docetaxel (DTXL) and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. In order to achieve high drug loading, about 30% solids in the organic phase is used.

The primary, coarse emulsion is formed by the combination of the two phases under simple mixing or through the use of a rotor stator homogenizer. The rotor/stator yielded a homogeneous milky solution, while the stir bar produced a visibly larger coarse emulsion. It was observed that the stir bar method resulted in significant oil phase droplets adhering to the side of the feed vessel, suggesting that while the coarse emulsion size is not a process parameter critical to quality, it should be made suitably fine in order to prevent yield loss or phase separation. Therefore the rotor stator is used as the standard method of coarse emulsion formation, although a high speed mixer may be suitable at a larger scale.

Figure 5:
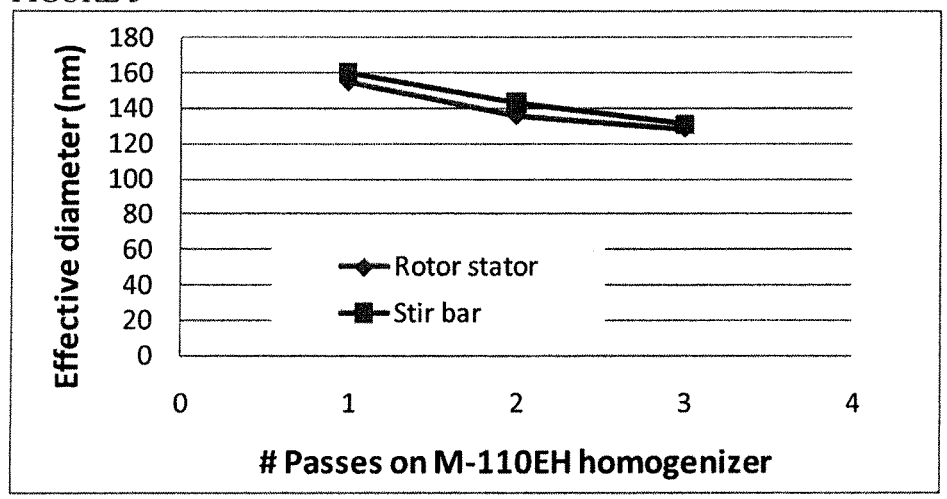
FIG. 5 depicts the effect of coarse emulsion preparation on quenched particle size. Placebo organic at 30% solids was used, emulsified at 5:1 W:O using standard aqueous phase (1% sodium cholate, 2% benzyl alcohol, 4% ethyl acetate).

The primary emulsion is then formed into a fine emulsion through the use of a high pressure homogenizer. The size of the coarse emulsion does not significantly affect the particle size after successive passes (103) through the homogenizer. M-110-EH (FIG. 5).

Figure 6:
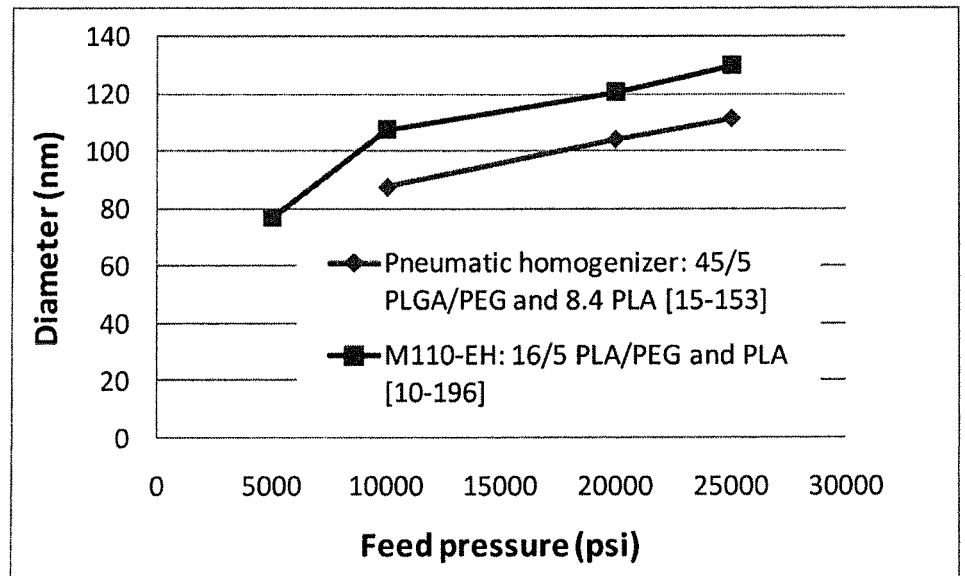
FIG. 6 depicts the effect of feed pressure on resultant particle size.

Homogenizer feed pressure was found to have a significant impact on resultant particle size. On both the pneumatic and electric M-110EH homogenizers, it was found that reducing the feed pressure also reduced the particle size (FIG. 6). Therefore the standard operating pressure used for the M-110EH is 4000-5000 psi per interaction chamber, which is the minimum processing pressure on the unit. The M-110EH also has the option of one or two interaction chambers. It comes standard with a restrictive Y-chamber, in series with a less restrictive 200 μm Z-chamber. It was found that the particle size was actually reduced when the Y-chamber was removed and replaced with a blank chamber. Furthermore, removing the Y-chamber significantly increases the flow rate of emulsion during processing.

Figure 7:
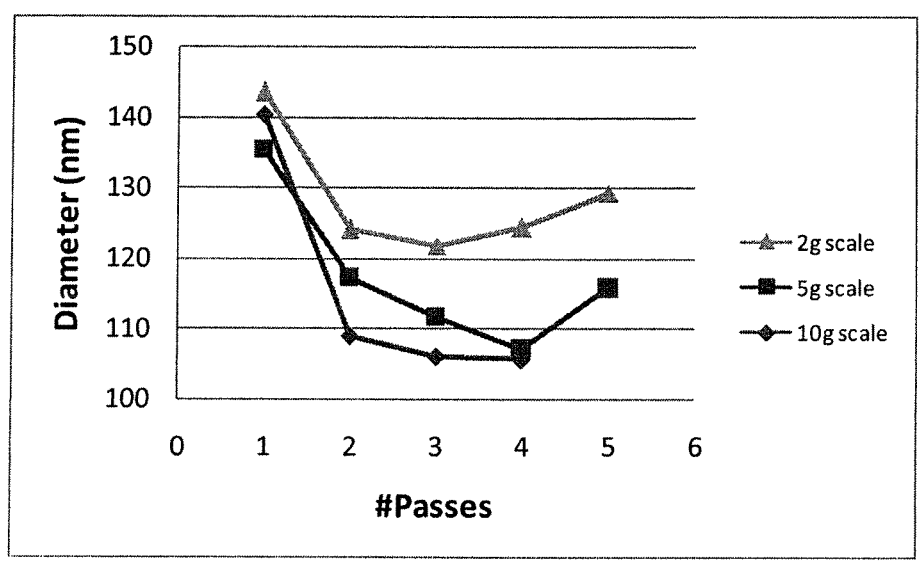
FIG. 7 depicts the particle size dependence on scale.

After 2-3 passes the particle size was not significantly reduced, and successive passes can even cause a particle size increase. The results are summarized in FIG. 7, where placebo organic phase consisted of 25.5% polymer stock of 50:50 16.5/5 PLA/PEG:8.2 PLA. Organic phase was emulsified 5:1 O:W with standard aqueous phase, and multiple discreet passes were performed, quenching a small portion of emulsion after each pass. The indicated scale represents the total solids of the formulation.

Figure 8:
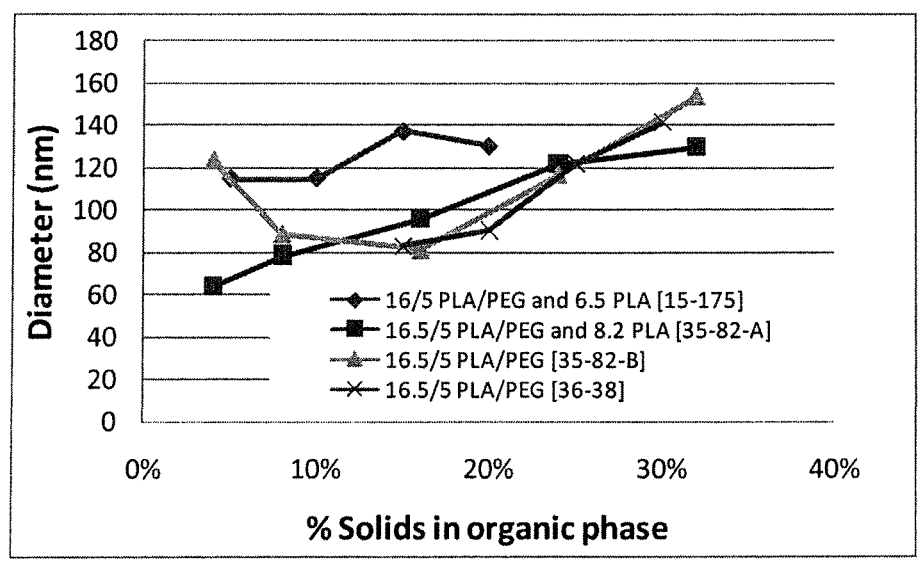
FIG. 8 depicts the effect of solids concentration on particle size.
Figure 9:
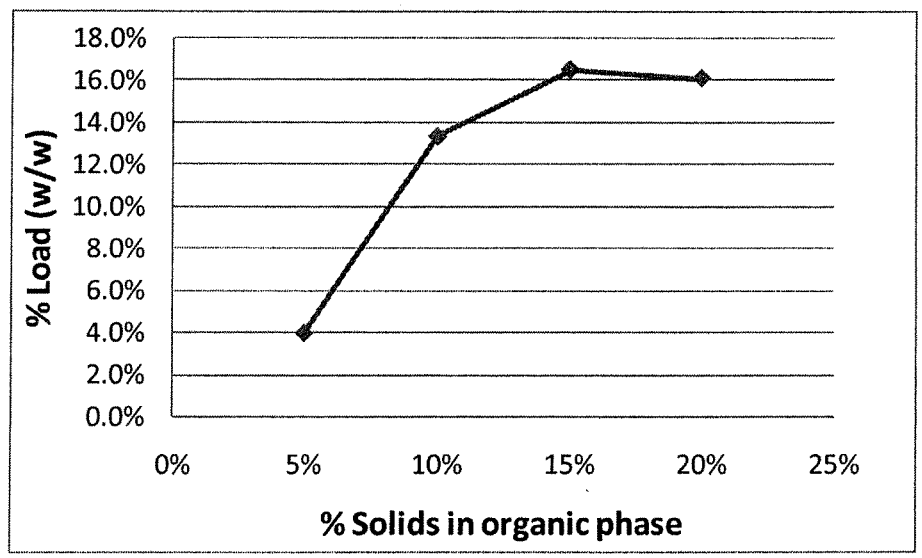
FIG. 9 depicts the effect of solids concentration of drug loading.

The effect of scale on particle size showed surprising scale dependence. The trend shows that in the 2-10 g batch size range, larger batches produce smaller particles. It has been demonstrated that this scale dependence is eliminated when considering greater than 10 g scale batches. The amount of solids used in the oil phase was about 30%. FIGS. 8 and 9 depicts the effect of solids concentration on particle size and drug loading; with the exception of the 15-175 series, all batches are placebo. For placebo batches the value for % solids represents the % solids were drug present at the standard 20% w/w.

Table A summarizes the emulsification process parameters.

TABLE A

| Parameter | Value | Observation |
|---|---|---|
| Coarse emulsion formation | Rotor stator homogenizer | Coarse emulsion size does not affect final particle size, but large coarse emulsion can cause increased oil phase retention in feed vessel |
| Homogenizer feed pressure | 4000-5000 psi per chamber | Lower pressure reduces particle size |
| Interaction chamber(s) | 2 × 200 μm Z-chamber | 200 μm Z-chamber yields the smallest particle size, and allows for highest homogenizer throughput |
| Number of homogenizer passes | 2-3 passes | Studies have shown that the particle size is not significantly reduced after 2 discreet passes, and size can even increase with successive passes |
| Water phase [sodium cholate] | 0.1% | [Sodium cholate] can effectively alter particle size; value is optimized for given process and formulation |
| W:O ratio | 5:1 | Lowest ratio without significant particle size increase is ~5:1 |
| [Solids] in oil phase | 30% | Increased process efficiency, increased drug encapsulation, workable viscosity |

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. Chilling the quench significantly improved drug encapsulation. The quench:emulsion ratio is approximately 5:1.

A solution of 35% (wt %) of Tween 80 is added to the quench to achieve approximately 2% Tween 80 overall After the emulsion is quenched a solution of Tween-80 is added which acts as a drug solubilizer, allowing for effective removal of unencapsulated drug during filtration. Table B indicates each of the quench process parameters.

TABLE B

Summary quench process parameters.

| Parameter | Value | Observation |
|---|---|---|
| Initial quench temperature | <5° C. | Low temperature yields higher drug encapsulation |
| [Tween-80] solution | 35% | Highest concentration that can be prepared and readily disperses in quench |
| Tween-80:drug ratio | 25:1 | Minimum amount of Tween-80 required to effectively remove unencapsulated drug |
| Q:E ratio | 5:1 | Minimum Q:E ratio while retaining high drug encapsulation |
| Quench hold/processing temp | ≤5° C. (with current 5:1 Q:E ratio, 25:1 Tween-80:drug ratio) | Temperature which prevents significant drug leaching during quench hold time and initial concentration step |

The temperature must remain cold enough with a dilute enough suspension (low enough concentration of solvents) to remain below the $T_g$ of the particles. If the Q:E ratio is not high enough, then the higher concentration of solvent plasticizes the particles and allows for drug leakage. Conversely, colder temperatures allow for high drug encapsulation at low Q:E ratios (to ~3:1), making it possible to run the process more efficiently.

The nanoparticles are then isolated through a tangential flow filtration process to concentrate the nanoparticle suspension and buffer exchange the solvents, free drug, and drug solubilizer from the quench solution into water. A regenerated cellulose membrane is used with a molecular weight cutoffs (MWCO) of 300.

A constant volume diafiltration (DF) is performed to remove the quench solvents, free drug and Tween-80. To perform a constant-volume DF, buffer is added to the retentate vessel at the same rate the filtrate is removed. The process parameters for the TFF operations are summarized in Table C. Crossflow rate refers to the rate of the solution flow through the feed channels and across the membrane. This flow provides the force to sweep away molecules that can foul the membrane and restrict filtrate flow. The transmembrane pressure is the force that drives the permeable molecules through the membrane.

TABLE C

TFF Parameters

| Parameter | Optimized Value | Effect |
|---|---|---|
| Membrane Material | Regenerated cellulose - Coarse Screen Membrane | No difference in performance between RC and PES, but solvent compatibility is superior for RC. |
| Molecular Weight Cut off | 300 kDa | No difference in NP characteristics (i.e. residual tween)Increase in flux rates is seen with 500 kDa membrane but 500 kDa is not available in RC |
| Crossflow Rate | 11 L/min/m² | Higher crossflow rate led to higher flux |
| Transmembrane Pressure | 20 psid | Open channel membranes have maximum flux rates between 10 and 30 psid. Coarse channel membranes have maximum flux rates with min TMP (~20 psid). |
| Concentration of Nanoparticle Suspension for Diafiltration | 30 mg/ml | Diafiltration is most efficient at [NP] ~50 mg/ml with open channel TFF membranes based on flux rates and throughput. With coarse channel membranes the flux rate is optimized at ~30 mg/ml in the starting buffer. |
| Number of Diavolumes | ≥15 (based on flux increase) | About 15 diavolumes are needed to effectively remove tween-80. End point of diafiltration is determined by in-process control (flux increase plateau). |
| Membrane Area | ~1 m²/kg | Membranes sized based on anticipated flux rates and volumes required. |

The filtered nanoparticle slurry is then thermal cycled to an elevated temperature during workup. A small portion (typically 5-10%) of the encapsulated drug is released from the nanoparticles very quickly after its first exposure to 25° C. Because of this phenomenon, batches that are held cold during the entire workup are susceptible to free drug or drug crystals forming during delivery or any portion of unfrozen storage. By exposing the nanoparticle slurry to elevated temperature during workup, this 'loosely encapsulated' drug can be removed and improve the product stability at the expense of a small drop in drug loading. Table D summarizes two examples of 25° C. processing. Other experiments have shown that the product is stable enough after ~2-4 diavolumes to expose it to 25° C. without losing the majority of the encapsulated drug. 5 diavolumes is used as the amount for cold processing prior to the 25° C. treatment.

TABLE D

| | | Lots A | Lots B |
|---|---|---|---|
| Drug load | Cold workup | 11.3% | 9.7% |
| | 25° C. workup[1] | 8.7-9.1% | 9.0-9.9% |
| Stability[2] | Cold workup | <1 day | <1 day |
| | 25° C. workup[1] | 5-7 days | 2-7 days |
| In vitro burst[3] | Cold workup | ~10% | Not performed |
| | 25° C. workup[1] | ~2% | |

[1]25° C. workup sublots were exposed to 25° C. after at least 5 diavolumes for various periods of time. Ranges are reported because there were multiple sublots with 25° C. exposure.
[2]Stability data represents the time that final product could be held at 25° C. at 10-50 mg/ml nanoparticle concentrations prior to crystals forming in the slurry (visible by microscopy)
[3]In vitro burst represents the drug released at the first time point (essentially immediately)

After the filtration process the nanoparticle suspension is passed through a sterilizing grade filter (0.2 μm absolute). Pre-filters are used to protect the sterilizing grade filter in order to use a reasonable filtration area/time for the process. Values are as summarized in Table E.

TABLE E

| Parameter | O Value | Effect |
|---|---|---|
| Nanoparticle Suspension | 50 mg/ml | Yield losses are higher at higher [NP], but the ability to |

TABLE E-continued

| Parameter | O Value | Effect |
|---|---|---|
| Concentration | | filter at 50 mg/ml obviates the need to aseptically concentrate after filtration |
| Filtration flow rate | ~1.3 L/min/m² | Filterability decreases as flow rate increases |

The filtration train is Ertel Alsop Micromedia XL depth filter M953P membrane (0.2 μm Nominal); Pall SUPRAcap with Seitz EKSP depth filter media (0.1-0.3 μm Nominal); Pall Life Sciences Supor EKV 0.65/0.2 micron sterilizing grade PES filter.

0.2 m² of filtration surface area per kg of nanoparticles for depth filters and 1.3 m2 of filtration surface area per kg of nanoparticles for the sterilizing grade filters can be used.

Example 9

Target-specific nanoparticles can be prepared that include a biocompatible polymer congutated to e.g. PEG, the chemotherapeutics described herein, and optionally conjugated to GL1 or GL2. Exemplary nanoparticles are shown in Table 1 below:

TABLE 1

Nanoparticles having a listed therapeutic agent and a polymer conjugate comprising: Biocompatible Polymer-Polymer -(Targeting Moiety)

| Therapeutic Agent | Biocompatible Polymer | Polymer | Targeting Moiety (Optional) |
|---|---|---|---|
| vincristine | PLGA | PEG | GL1 |
| vincristine | PLA | PEG | GL1 |
| vincristine | PGA | PEG | GL1 |
| vincristine | PLGA | PEG | GL2 |
| vincristine | PLA | PEG | GL2 |
| vincristine | PGA | PEG | GL2 |
| vincristine | PLGA | PEG-DSPE | GL1 |
| vincristine | PLA | PEG-DSPE | GL1 |
| vincristine | PGA | PEG-DSPE | GL1 |
| vincristine | PLGA | PEG-DSPE | GL2 |
| vincristine | PLA | PEG-DSPE | GL2 |
| vincristine | PGA | PEG-DSPE | GL2 |
| docetaxel | PLGA | PEG | GL1 |
| docetaxel | PLA | PEG | GL1 |
| docetaxel | PGA | PEG | GL1 |
| docetaxel | PLGA | PEG | GL2 |
| docetaxel | PLA | PEG | GL2 |
| docetaxel | PGA | PEG | GL2 |
| docetaxel | PLGA | PEG-DSPE | GL1 |
| docetaxel | PLA | PEG-DSPE | GL1 |
| docetaxel | PGA | PEG-DSPE | GL1 |
| docetaxel | PLGA | PEG-DSPE | GL2 |
| docetaxel | PLA | PEG-DSPE | GL2 |
| docetaxel | PGA | PEG-DSPE | GL2 |
| sirolimus | PLGA | PEG | GL1 |
| sirolimus | PLA | PEG | GL1 |
| sirolimus | PGA | PEG | GL1 |
| sirolimus | PLGA | PEG | GL2 |
| sirolimus | PLA | PEG | GL2 |
| sirolimus | PGA | PEG | GL2 |
| sirolimus | PLGA | PEG-DSPE | GL1 |
| sirolimus | PLA | PEG-DSPE | GL1 |
| sirolimus | PGA | PEG-DSPE | GL1 |
| sirolimus | PLGA | PEG-DSPE | GL2 |
| sirolimus | PLA | PEG-DSPE | GL2 |
| sirolimus | PGA | PEG-DSPE | GL2 |
| gemcitabine | PLGA | PEG | GL1 |
| gemcitabine | PLA | PEG | GL1 |
| gemcitabine | PGA | PEG | GL1 |
| gemcitabine | PLGA | PEG | GL2 |
| gemcitabine | PLA | PEG | GL2 |
| gemcitabine | PGA | PEG | GL2 |
| gemcitabine | PLGA | PEG-DSPE | GL1 |
| gemcitabine | PLA | PEG-DSPE | GL1 |
| gemcitabine | PGA | PEG-DSPE | GL1 |
| gemcitabine | PLGA | PEG-DSPE | GL2 |
| gemcitabine | PLA | PEG-DSPE | GL2 |
| gemcitabine | PGA | PEG-DSPE | GL2 |
| 5-fluorouracil | PLGA | PEG | GL1 |
| 5-fluorouracil | PLA | PEG | GL1 |
| 5-fluorouracil | PGA | PEG | GL1 |
| 5-fluorouracil | PLGA | PEG | GL2 |
| 5-fluorouracil | PLA | PEG | GL2 |
| 5-fluorouracil | PGA | PEG | GL2 |
| 5-fluorouracil | PLGA | PEG-DSPE | GL1 |
| 5-fluorouracil | PLA | PEG-DSPE | GL1 |
| 5-fluorouracil | PGA | PEG-DSPE | GL1 |
| 5-fluorouracil | PLGA | PEG-DSPE | GL2 |
| 5-fluorouracil | PLA | PEG-DSPE | GL2 |
| 5-fluorouracil | PGA | PEG-DSPE | GL2 |
| paclitaxel | PLGA | PEG | GL1 |
| paclitaxel | PLA | PEG | GL1 |
| paclitaxel | PGA | PEG | GL1 |
| paclitaxel | PLGA | PEG | GL2 |
| paclitaxel | PLA | PEG | GL2 |
| paclitaxel | PGA | PEG | GL2 |
| paclitaxel | PLGA | PEG-DSPE | GL1 |
| paclitaxel | PLA | PEG-DSPE | GL1 |
| paclitaxel | PGA | PEG-DSPE | GL1 |
| paclitaxel | PLGA | PEG-DSPE | GL2 |
| paclitaxel | PLA | PEG-DSPE | GL2 |
| paclitaxel | PGA | PEG-DSPE | GL2 |
| daunorubicin | PLGA | PEG | GL1 |
| daunorubicin | PLA | PEG | GL1 |
| daunorubicin | PGA | PEG | GL1 |
| daunorubicin | PLGA | PEG | GL2 |
| daunorubicin | PLA | PEG | GL2 |
| daunorubicin | PGA | PEG | GL2 |
| daunorubicin | PLGA | PEG-DSPE | GL1 |
| daunorubicin | PLA | PEG-DSPE | GL1 |
| daunorubicin | PGA | PEG-DSPE | GL1 |
| daunorubicin | PLGA | PEG-DSPE | GL2 |
| daunorubicin | PLA | PEG-DSPE | GL2 |
| daunorubicin | PGA | PEG-DSPE | GL2 |

Example 10

Nanoparticles shown in Table 2 are prepared using the procedure in Example 8. Nanoparticles comprising macromolecules of PLGA-PEG and macromolecules of PLGA-PEG-small-molecule ligand (SML) were prepared as shown in studies 1 and 2, below. In studies 3 and 4, nanoparticles comprising macromolecules of PLA-PEG, macromolecules of PLGA-PEG-SML, and macromolecules of PLA were prepared (DB=diblock copolymer).

The ratio of small-molecule targeting moiety-functionalized macromolecules with nonfunctionalized macromolecules can be adjusted, and using study 1, nanoparticles with polymer compositions that are approximately 0.94 mole %, 4.63 mole % and 9.01 mole % functionalized macromolecules can be prepared (see "mol % DB-GL2 of total Poly"). Additionally, using these methods, nanoparticles comprising approximately 0.015, 0.073 and 0.143 weight % small-molecule ligand with respect to total polymer can be prepared (see "Wt. % GL2 wrt poly.").

Nanoparticles with functionalized polymers that constitute approximately 0.1-30, e.g., 0.1-20, e.g., 0.1-10 mole percent of the entire polymer composition of the nanoparticle can also be prepared, as well as nanoparticles having a weight percent low-molecular weight ligand with respect to total polymer is between 0.001 and 5, e.g., 0.001 and 2, e.g., 0.001 and 1.

TABLE 2

| | Wt. % of Solids | Wt. % of Polymer | wt. % DB-GL2 of PLA-PEG | mol % DB-GL2 of total Poly. |
|---|---|---|---|---|
| Study 1 | 0.362 | 0.381052632 | NA | 0.947217483 |
| | 1.81 | 1.905263158 | NA | 4.630814102 |
| | 3.62 | 3.810526316 | NA | 9.011251618 |
| Study 2 | 0.181 | 0.190526316 | NA | 0.474958408 |
| | 0.362 | 0.381052632 | NA | 0.947217483 |
| | 0.543 | 0.571578947 | NA | 1.416800171 |
| | 1.81 | 1.905263158 | NA | 4.630814102 |

TABLE 2-continued

| | | | | |
|---|---|---|---|---|
| Study 3 | 0.362 | 0.4525 | NA | 0.178974269 |
| | 1.81 | 2.2625 | NA | 0.891043972 |
| Study 4 | 0.080241 | 0.100300903 | 0.200601805 | 0.079390136 |
| Calc. for | 0.161616 | 0.202020202 | 0.404040404 | 0.159825753 |
| 45K-5K | 0.842105 | 1.052631579 | 2.105263158 | 0.829427309 |
| PLA-PEG | 1.702128 | 2.127659574 | 4.255319149 | 1.668024361 |
| Study 4 | 0.190522 | 0.238151941 | 0.476303882 | 0.16998719 |
| Calc. for | 0.381134 | 0.476417342 | 0.952834683 | 0.340027827 |
| 16K-5K | 1.909308 | 2.386634845 | 4.77326969 | 1.702280075 |
| PLA-PEG | 3.827751 | 4.784688995 | 9.56937799 | 3.409927685 |
| NO PLA | 0.323232 | 0.404040404 | 0.404040404 | 0.159825753 |

| | Mol. % GL2 | Wt. % GL2 wrt poly. | GL2 content ppm |
|---|---|---|---|
| Study 1 | 0.947217483 | 0.015108 | 151.0812 |
| | 4.630814102 | 0.073861 | 738.6148 |
| | 9.011251618 | 0.143729 | 1437.295 |
| Study 2 | 0.474958408 | 0.007576 | 75.75587 |
| | 0.947217483 | 0.015108 | 151.0812 |
| | 1.416800171 | 0.022598 | 225.9796 |
| | 4.630814102 | 0.073861 | 738.6148 |
| Study 3 | 0.178974269 | 0.002855 | 28.5464 |
| | 0.891043972 | 0.014212 | 142.1215 |
| Study 4 | 0.079390136 | 0.001266 | 12.66273 |
| Calc. for | 0.159825753 | 0.002549 | 25.49221 |
| 45K-5K | 0.829427309 | 0.013229 | 132.2937 |
| PLA-PEG | 1.668024361 | 0.026605 | 266.0499 |
| Study 4 | 0.16998719 | 0.002711 | 27.11296 |
| Calc. for | 0.340027827 | 0.005423 | 54.23444 |
| 16K-5K | 1.702280075 | 0.027151 | 271.5137 |
| PLA-PEG | 3.409927685 | 0.054388 | 543.8835 |
| NO PLA | 0.159825753 | 0.002549 | 25.49221 |

Example 11

Various nanoparticle formulations are formed using the procedure of Example 8 as depicted and compared in Table F:

TABLE F

| Formulation | Polymer Type | % Solids | Load and particle size |
|---|---|---|---|
| Polymer-PEG:PLA Ratio (80:0; 60:20; 40:40 (baseline), 20:60) | 16-5 PLA-PEG: PLA Ratio | 5% | |
| | 45-5 PLGA-PEG: PLA Ratio | 5% | |
| PLA Molecular Weight = 1.9, 4, 6.5 (baseline), 8.5 kDa | 16-5 PLA-PEG: PLA (40:40) | 5% | 1.9 and 4 kDa had lower load = 2.5% |
| 15-5 Vs 16-5 PLA-PEG:PLA (40:40) | 15-5 PLA-PEG: PLA (40:40) | 5% | Both 15-5 PLA-PEG and 16-5 PLA-PEG are the same in load and particle size |
| Total % Solid 5% Vs. 15% | 16-5 PLA-PEG: PLA (40:40) | 5% or 15% | When use 15% solids; 3X greater encapsulation efficiency |
| 16-5 PLGA-PEG Vs. PLA-PEG (baseline) with PLA (40:40) | 16-5 PLGA-PEG: PLA (40:40) | 15% | Both 16-5 PLGA-PEG and 16-5 PLA-PEG are equivalent as to % load and particle size |
| Alternative polymer: PLGA-PEG | 28-5 PLGA-PEG: PLA (40:40) | 15% | 28-5 PLGA-PEG = larger particle size as compared to others |
| | 45-5 PLGA-PEG: PLA (40:40) | 15% | 45-5 PLGA-PEG = larger particle size |
| Ratio of Benzyl Alcohol to Ethyl Acetate: 11:89, 21:79 (baseline), 32:68 BA:EA | 16-5 PLA-PEG: PLA (40:40) | 15% | Ratio = 21:79 (10.8% load); 32:68 and 11:89 resulted in 9.4 and 8.8% load, respectively. |
| Compare Solvent to Benzyl Alcohol: Heptanol or Hexanol | 16-5 PLA-PEG: PLA (40:40) | 15% | Solvent = benzyl alcohol (10.8% load); heptanol and hexanol both resulted in ~2% load |
| Target Load 10, 20 (baseline), 30% | 16-5 PLA-PEG: PLA (40:40) | 15% | Load increased with target load: % Load = 5.8%, 9%, 13.3%, respectively |

Figure 10:
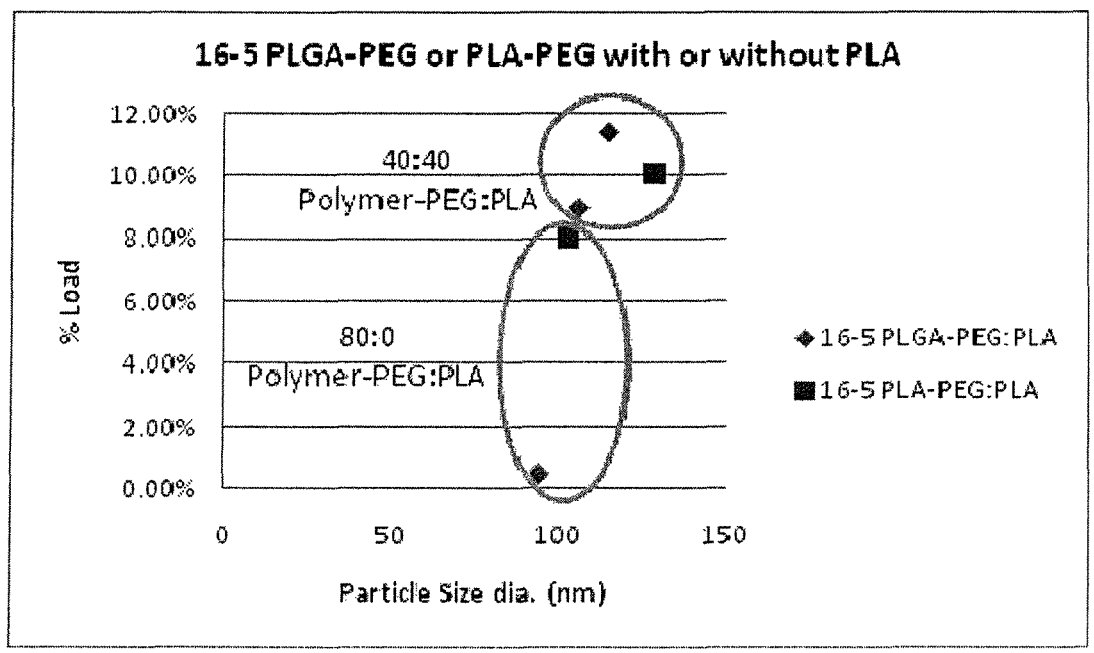
FIG. 10 depicts the effect of homopolymer PLA with PLGA-PEG or PLA-PEG on DTXL (docetaxel) loading.
Figure 11:
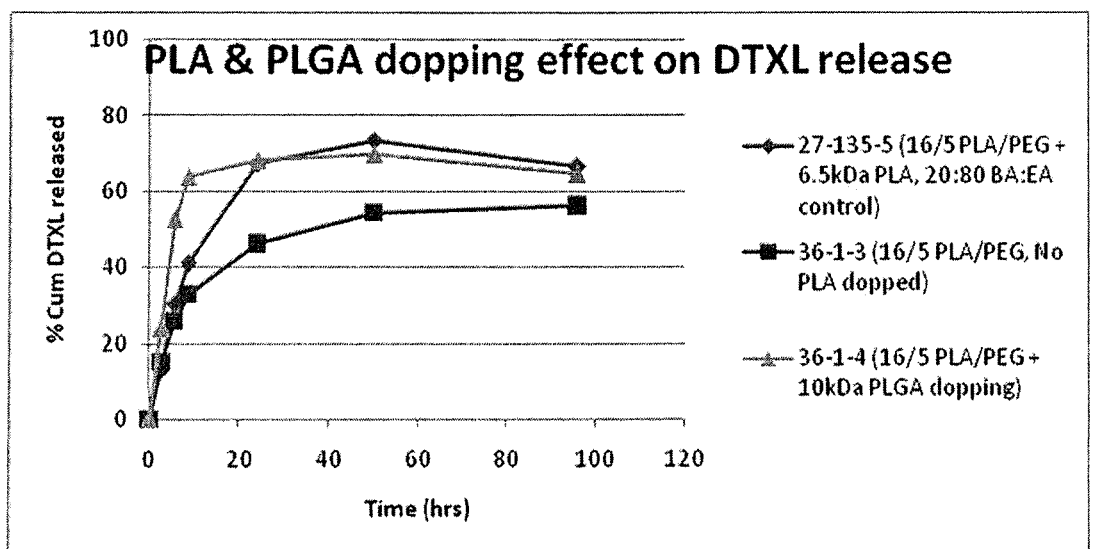
FIG. 11 depicts the effect of homopolymer PLA as part of a nanoparticle on the rate of drug release of a nanoparticle.
Figure 12:
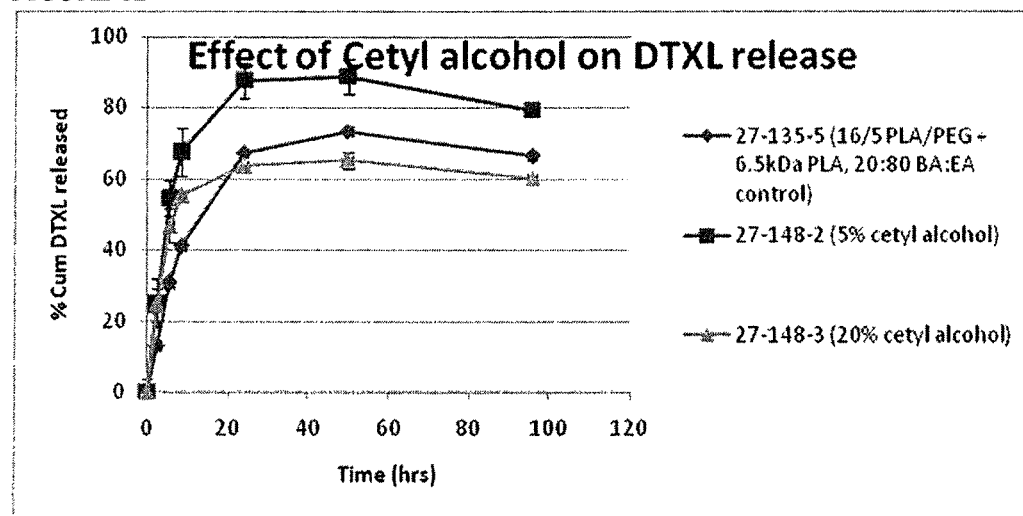
FIG. 12 depicts the effect of cetyl alcohol on the initial rate of drug release of a nanoparticle.

An optimal particle size can be achieved without using homopolymer PLA and without significantly sacrificing drug load, as shown in FIG. 10. Batches with PLA homopolymer release drug significantly faster than batches made using co-polymer alone FIG. 11). The various polymer types and molecular weights added no additional value in optimizing drug load and particle size. To the contrary, at 15% total solids with "alternative polymer" types particle size were typically larger than a target size of 100-120 nm. Cetyl alcohol at 5 wt % incorporation generally increased the rate of in vitro release (FIG. 12).

Example 12

Cryoprotectant

Freezing a suspension of nanoemulsion nanoparticles in deionized water alone results in particle aggregation. This is believed to be due to crystallization and entanglement of PEG chains on the nanoparticle surfaces (Jaeghere et al; Pharmaceutical Research 16(6), p 859-852). Sugar-based excipients (sucrose, trehalose, or mannitol) can act to cryoprotect these nanoparticles under freeze/thaw conditions, with a concentrations as low as 1 wt % for dilute (~10 mg/ml) nanoparticle suspensions. One formulation includes 10 wt % sucrose, which contains excess sucrose to what is required and is the same osmolality as physiological saline.

Table G shows that 16/5 PLA-PEG co-polymer is less susceptible to freeze-thaw aggregation.

TABLE G

| Description | Original Median PSD/PD | Post-F/T Median PS (nm) | Post-F/T Poly-dis-persity | Post-F/T Baseline Index |
|---|---|---|---|---|
| 1:1 45/5 and PLA (baseline) | 143.4, 0.124 | 358.9 | 0.358 | 0.0/23.16% |
| 16/5 PLA-PEG and PLA (1:1) | 186.7, 0.080 | 189.5 | 0.126 | 9.7/91.57% |
| 2:1:1 16/5: PLA:cetyl | 174.1, 0.084 | 232.7 | 0.146 | 0.0/61.19% |
| 2:1:1 45/5: PLA:cetyl | 111.0, 0.182 | 0 | 0 | 0.0/1.55% |
| 16/5 PLA-PEG alone | 218.8, 0.098 | 226.9 | 0.03 | 7.3/60.56% |
| 16/5 PLA-PEG and PLA (3:1) | 222.2, 0.126 | 230.7 | 0.065 | 4.1/35.36% |
| 45/5 PLGA-PEG and PLA (3:1) | 162.7, 0.099 | 178.6 | 0.091 | 7.7/95.41% |
| 2:1:1 45/5 PLA-PEG:PLA:cetyl | 115.9, 0.154 | 734.6 | 0.392 | 0.0/13.27% |

Example 13

Palladium Removal

Based on a dose level (ug/day) in a human clinical trials, a maximum acceptable palladium level in a PLA-PEG-GL2 composition is ca. 10 ppm. Polymer (PLA-PEG-GL2) solutions (20 or 35 mg/mL) in dichloromethane (DCM) were loaded on to 5 g resin columns (pre-solvated with 10 mL DCM) and subsequent eluted using 30 mL DCM under gravity. Polymer was recovered by solvent removal using rotary evaporation followed by vacuum drying at room temperature. Polymer recovery was determined gravimetrically and residual palladium content was determined by Inductively Coupled Plasma (ICP) Spectroscopy at Galbraith Laboratories Inc.

| | PLA-PEG-GL2 solution and yield | | | | Palladium content (ppm) | | |
|---|---|---|---|---|---|---|---|
| Resin used | Sol-vent | mg/mL | mg/5 g resin | wt. % recovery | Test 1 | Test 2 | Aver-age |
| Guani-dine | DCM | 20 | 220 | 23 | 337 | 347 | 342 |
| Thiol | DCM | 20 | 220 | 62 | 39 | 30 | 34.5 |
| TMT | DCM | 20 | 220 | 92 | 11 | 7 | 9 |
| Urea | DCM | 20 | 220 | 60 | 4470 | NA | 4470 |
| Thio-urea | DCM | 20 | 220 | 45 | 40 | 36 | 38 |
| Control | DCM | 20 | NA | NA | 4060 | 3980 | 4020 |
| TMT | DCM | 35 | 335 | 91 | 9 | 7 | 8 |
| Urea | DCM | 35 | 335 | 60 | 5360 | 4920 | 5140 |
| Control | DCM | NA | NA | NA | 4240 | 4300 | 4270 |
| TMT | DCM | 35 | 1050 | 92 | 3.8 | 2.7 | 3.25 |
| Control | DCM | NA | NA | NA | 3780 | 3880 | 3830 |

Table H

As seen in Table H, thiol, TMT, urea and thiourea functionalities brought palladium levels below 50 ppm at the polymer load per unit resin weight evaluated. However, only the TMT (trimecaptotriazine) resin yielded good (>90%) polymer recovery. In addition, TMT resin also yielded palladium contents under the 10 ppm acceptance threshold. There appear to be some variability in the results depending on experimental conditions used. In particular, palladium removal is more effective when the 5 g TMT resin column was loaded with 1050 mg polymer. This may be due to longer residence time of the polymeric species and palladium catalyst under these experimental conditions.

Example 14

Formulation

A formulation that includes nanoparticles of PLA-PEG-ligand, PLA, PLA-PEG, and docetaxel, in a sucrose/water composition is formed:

| Component | Nominal Concentration (mg/mL) |
|---|---|
| Docetaxel | 5 |
| PLA-PEG-ligand | 1.1 |
| PLA-PEG | 21.4 |
| PLA | 22.5 |
| Sucrose | 100 |
| Water | Q.S. |

Example 15

In vitro Release

An in vitro release method is used to determine the initial burst phase release from these nanoparticles at both ambient and 37° C. conditions. In order to maintain sink conditions and prevent nanoparticles from entering the release samples, a dialysis system was designed. After obtaining an ultracentrifuge capable of pelleting 100 nm particles, the dialysis membranes were eliminated and centrifugation was used to separate released drug from encapsulated drug.

The dialysis system is as follows: 3 mL slurry of docetaxel nanoparticles (approx 250 µg/mL drug/PLGA/PLA nanoparticles, corresponding to 2.5 mg/mL solid concentration) in DI-water is placed into the inner tube of a 300 kDa MWCO dialyzer by pipetting. The nanoparticle is suspension in this media. The dialyzer is placed into a glass bottles containing 130 ml release media (2.5% hydroxyl beta cyclodextrin in PBS), which is continually stirred at 150 rpm using a shaker to prevent the formation of an unstirred water layer at the membrane/outer solution interface. At pre-determined time points, aliquot of samples (1 mL) were withdrawn from the outer solution (dialysate) and analyzed for Docetaxel concentration by HPLC.

The centrifugal system is run using similar conditions at lower suspension volumes without dialysis bags. Samples are centrifuged at 60,000 g for 30 minutes and the supernatant is assayed for drug content to measured released drug.

Example 16

In vitro Release of Docetaxel Nanoparticles

Figure 13:
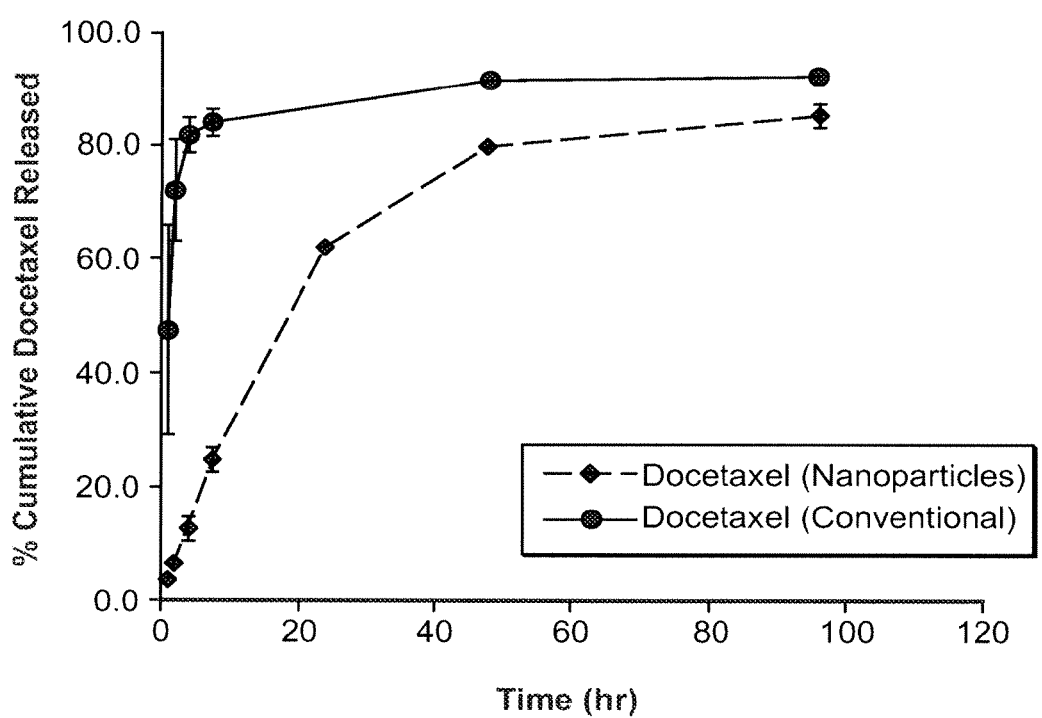
FIG. 13 depicts in vitro release of docetaxel from disclosed nanoparticles compared to conventional docetaxel

A suspension of docetaxel nanoparticles prepared as in Example 8 (10% by weight docetaxel and 90% by weight polymer (1.25 wt % PLA-PEG-GL2 and 98.75 wt % PLA-PEG, Mn PLA=16 Da; Mn PEG=5 Da) were placed in a dialysis cassette and incubated in a reservoir of PBS at 37 C with stirring. Sample of the dialysate were collected and analyzed for docetaxel using reversed phase HPLC. For comparison, conventional docetaxel was subjected to the same procedure. FIG. 13 depicts in vitro release profile of nanoparticles compared to the conventional docetaxel. Release of the encapsulated docetaxel from the polymer matrix was essentially linear over the first 24 hours with the remainder gradually released from the particles over a period of about 96 hours.

Example 17

Sirolimus Nanoparticles

Nanoparticle batches were prepared using the general procedure of Example 8, with 80% (w/w) Polymer-PEG or Polymer-PEG with homopolymer PLA at 40% (w/w) each, with a batch of % total solids of 5%, 15% and 30%. Solvents used were: 21% benzyl alcohol and 79% ethyl acetate (w/w). For each 2 gram batch size, 400 mg of drug was used and 1.6 g of 16-5 Polymer-PEG or 0.8 g of 16-5 Polymer-PEG+0.8 g of 10 kDa PLA (homopolymer) was used. The diblock polymer 16-5 PLA-PEG or PLGA-PEG (50:50 L:G) was used, and if used, the homopolymer: PLA with a Mn=6.5 kDa, Mw=10 kDa, and Mw/Mn=1.55.

The organic phase (drug and polymer) is prepared in 2 g batches: To 20 mL scintillation vial add drug and polymer(s). The mass of solvents needed at % solids concentration is shown below:
  i. 5% solids: 7.98 g benzyl alcohol+30.02 g ethyl acetate
  ii. 15% solids: 2.38 g benzyl alcohol+8.95 g ethyl acetate
  iii. 30% solids: 0.98 g benzyl alcohol+3.69 g ethyl acetate An aqueous solution is prepared with 0.5% sodium cholate, 2% benzyl alcohol, and 4% ethyl acetate in water. To a 2 L bottle add 7.5 g sodium cholate, 1402.5 g of DI water, 30 g of benzyl alcohol and 60 g of ethyl acetate, and mix on stir plate until dissolved.

For the formation of emulsion, a ratio of aqueous phase to oil phase of 5:1 is used. The organic phase is poured into the aqueous solution and homogenized using IKA for 10 seconds at room temperature to form course emulsion. The solution is fed through the homogenizer (110S) at 9 Kpsi (45 psi on gauge) for 2 discreet passes to form nanoemulsion.

The emulsion is poured into quench (D.I. water) at <5 C while stirring on stir plate. Ratio of quench to emulsion is 8:1.35% (w/w) Tween 80 is added in water to quench at ratio of 25:1 Tween 80 to drug. The nanoparticles are concentrated through TFF and the quench is concentrated on TFF with 500 kDa Pall cassette (2 membrane) to ~100 mL. Diafiltering is used using ~20 diavolumes (2 liter) of cold DI water, and the volume is brought down to minimal volume then collect final slurry, ~100 mL. The solids concentration of unfiltered final slurry is determined by the using tared 20 mL scintillation vial and adding 4 mL final slurry and dry under vacuum on lyo/oven and the weight of nanoparticles in the 4 mL of slurry dried down is determined. Concentrated sucrose (0.666 g/g) is added to final slurry sample to attain 10% sucrose.

Solids concentration of 0.45 um filtered final slurry was determined by filtering about 5 mL of final slurry sample before addition of sucrose through 0.45 µm syringe filter; to tared 20 mL scintillation vial add 4 mL of filtered sample and dry under vacuum on lyo/oven.

The remaining sample of unfiltered final slurry was frozen with sucrose. Rapamycin (sirolimus) formulations:

| Name | Polymer | Size (nm) | Drug Loading | Release of Drug (t = hr) | | | |
|---|---|---|---|---|---|---|---|
| | | | | T = 0 | T = 2 | T = 4 | T = 24 |
| 5% Solid | 16/5 PLA/PEG | 123.1 | 3.61% | ND | ND | ND | ND |
| | 16/5 PLA/PEG + PLA | 119.7 | 4.49% | ND | ND | ND | ND |
| 15% Solid | 16/5 PLA/PEG | 82.1 | 4.40% | ND | ND | ND | ND |
| | 16/5 PLA/PEG + PLA | 120.6 | 11.51% | ND | ND | ND | ND |
| 23% Solid | 16/5 PLA/PEG | 88.1 | 7.40% | ND | ND | ND | ND |
| | 16/5 PLA/PEG + PLA | 118.3 | 7.8% | ND | ND | ND | ND |
| 30% Solid | 16/5 PLA/PEG | 88.5 | 10.26% | 8.5 | 17.3 | 22.4 | 64.2 |
| | 16/5 PLA/PEG + PLA | 118.3 | 10.18% | 9.3 | 30.4 | 44.7 | 98.2 |

Figure 14:
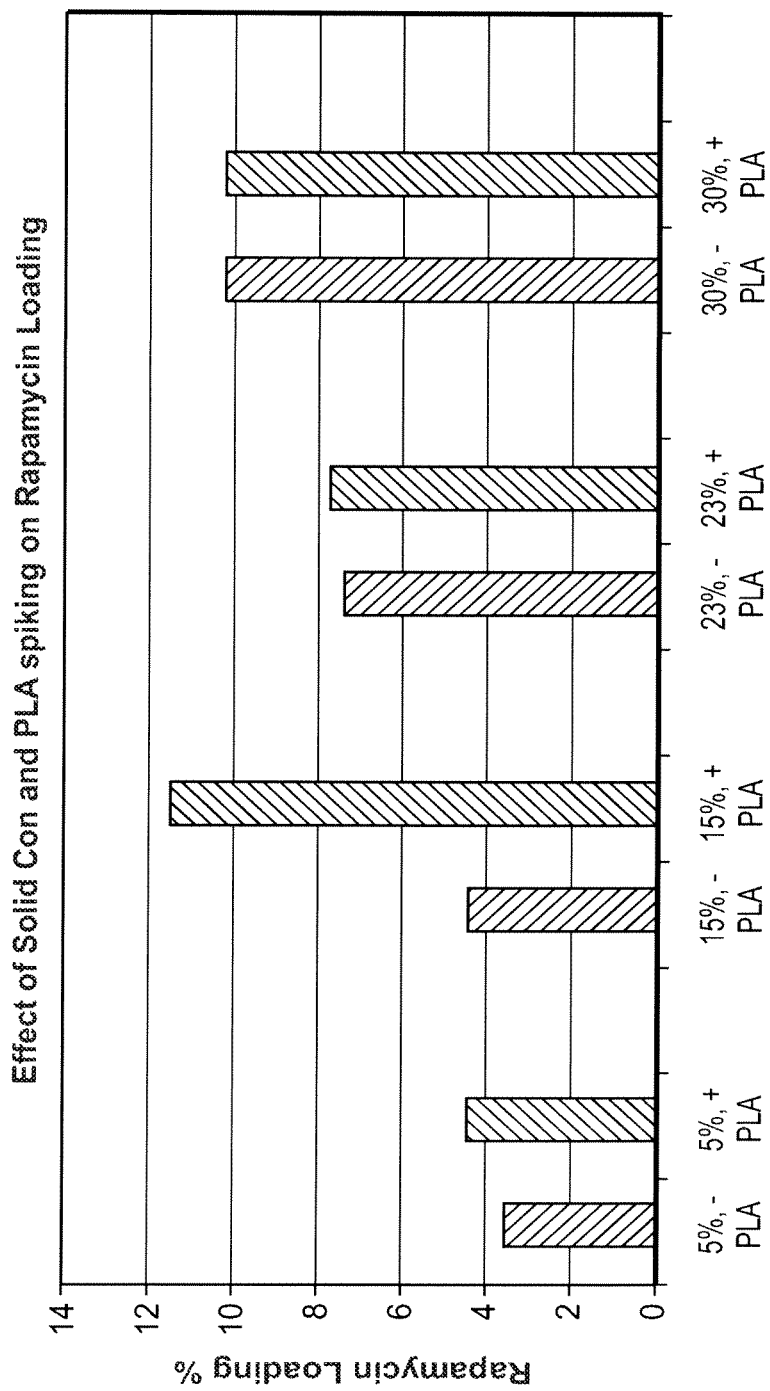
FIG. 14 depicts the effect of solids concentration and poly (lactic) homopolymer on loading percentage of sirolimus (rapamycin).

The effect of solid contents and the inclusions of poly (lactic) acid homopolymer is shown in FIG. 14.

Figure 15:
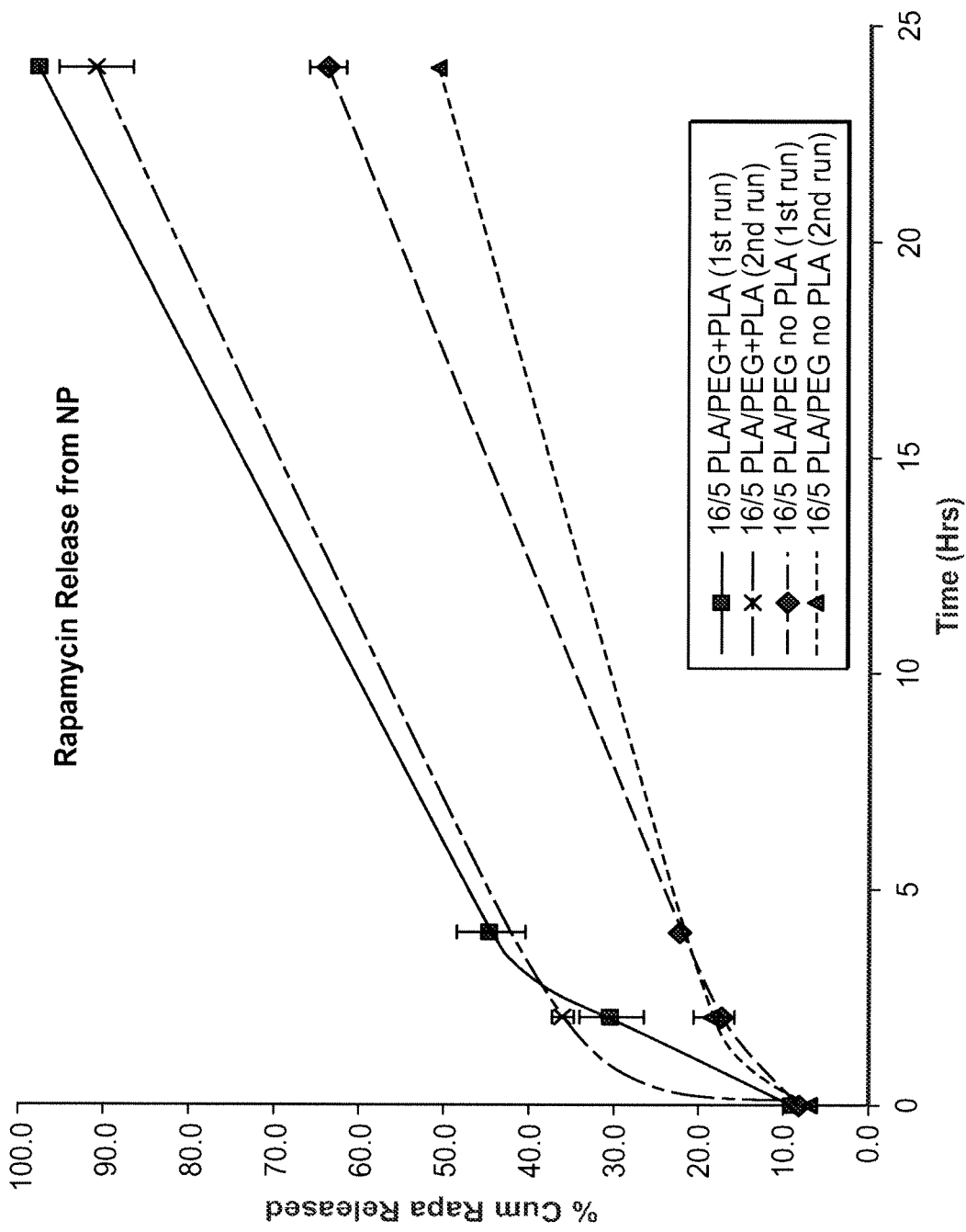
FIG. 15 depicts in vitro release of sirolimus over time for disclosed nanoparticles

In-vitro release experiments are studied by dispersing nanoparticles in PBS containing 10% (w/w) of Tween 20 (T20) at 37° C. T20 was used to increase the solubility of rapamycin in PBS to levels well detectable by HPLC as well as maintaining the sink condition. 3 mL of drug-loaded nanoparticles were redispersed in 130 mL of release medium in a jar at a known concentration (approximately 250 µg/ml). These volumes were chosen to ensure that the maximum concentration of the drug in the release medium would always be less than 10% of the maximum solubility, i.e., sink conditions. The media and nanoparticle suspension is stirred at 150 rpm. At pre-determined time points, 4 ml of aliquots were centrifuged at 50,000 rpm (236,000 g) for 1 hr to separate the nanoparticles from the elution media. The elution media is injected in to a HPLC to determine drug released from the nanoparticles. The release of rapamycin showed slow and sustained release, as shown in FIG. 15.

Example 18

Temsirolimus

Nanoparticles were prepared as in Example 17 and 8, except temsirolimus was used with 30% solid content in the organic phase before emulsion:

| Name | Polymer | Size (nm) | Drug Loading | Release of Drug (t = hr) | | | |
|------|---------|-----------|--------------|--------|--------|--------|--------|
| | | | | T = 0 | T = 2 | T = 4 | T = 24 |
| 30% Solid | 16/5 PLA/PEG | 97.5 | 9.9% | 11.5 | 15.6 | 17.9 | 40.9 |
| | 16/5 PLA/PEG + PLA | 112.8 | 14.2% | 9.8 | 22.3 | 29.9 | 88.0 |
| | 16/5 PLGA/PEG + PLA | 150.3 | 4.6 | ND | ND | ND | ND |
| | 16/5 PLGA/PEG + PLA | ND | 6.9 | 10.6 | 35.7 | 45.8 | 87.0 |

Figure 16:
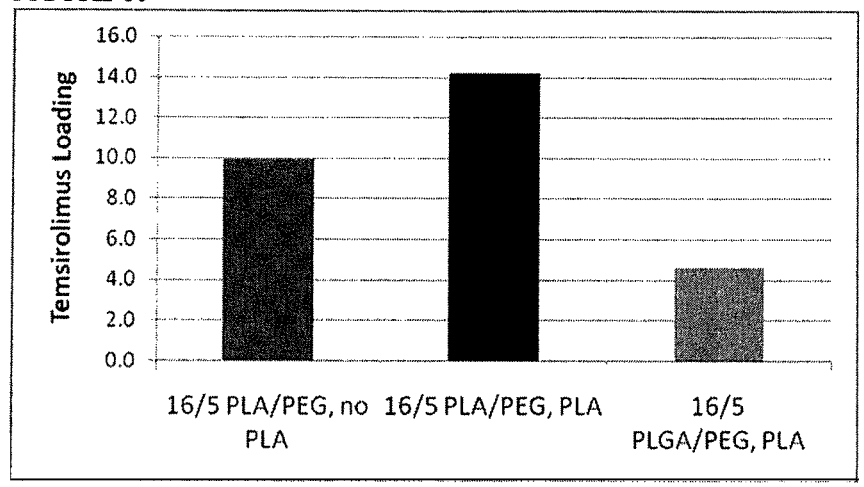
FIG. 16 depicts the effects of poly(lactic) homopolymer on loading percentage of temsirolimus.
Figure 17:
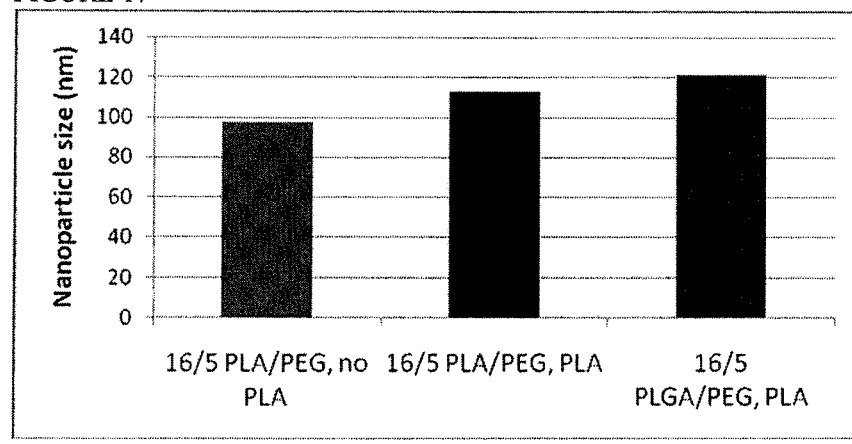
FIG. 17 depicts the effect of solids concentration on particle size of temsirolimus containing particles.
Figure 18:
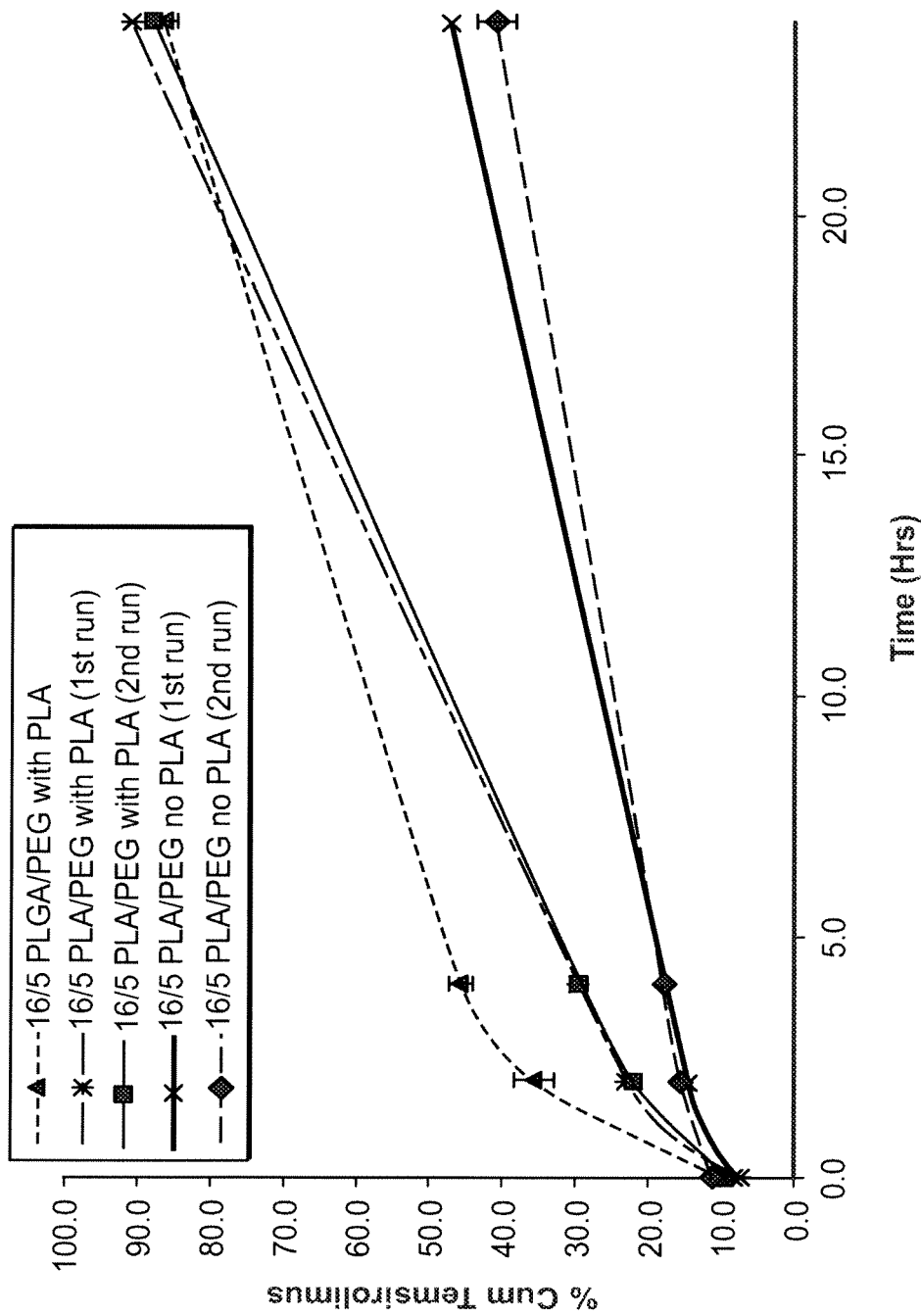
FIG. 18 depicts in vitro release of temsirolimus over time for disclosed nanoparticles

FIG. 16 depicts the weight % of temsirolimus and FIG. 17 depicts the nanoparticle for the different polymeric nanoparticles having temsirolimus. The results of an in-vitro release experiment as in Example 17 shows the slow and sustained release of temsirolimus showed slow and sustained release, as shown in FIG. 18.

Example 19

Vinorelbine Nanoparticles

Nanoparticle batches were prepared using the general procedure of Example 8, with 80% (w/w) Polymer-PEG or Polymer-PEG with homopolymer PLA at 40% (w/w) each, with a batch of % total solids of 5%, 15% and 30%. Solvents used were: 21% benzyl alcohol and 79% ethyl acetate (w/w). For each 2 gram batch size, 400 mg of vinorelbine was used and 1.6 g of 16-5 Polymer-PEG or 0.8 g of 16-5 Polymer-PEG+ 0.8 g of 10 kDa PLA (homopolymer) was used. The diblock polymer 16-5 PLA-PEG or PLGA-PEG (50:50 L:G) was used, and if used, the homopolymer: PLA with a Mn=6.5 kDa, Mw=10 kDa, and Mw/Mn=1.55.

The organic phase (drug and polymer) is prepared in 2 g batches: To 20 mL scintillation vial add drug and polymer(s). The mass of solvents needed at % solids concentration is shown below:

i. 5% solids: 7.98 g benzyl alcohol+30.02 g ethyl acetate ii. 15% solids: 2.38 g benzyl alcohol+8.95 g ethyl acetate iii. 30% solids: 0.98 g benzyl alcohol+3.69 g ethyl acetate An aqueous solution is prepared with 0.5% sodium cholate, 2% benzyl alcohol, and 4% ethyl acetate in water. Add to the bottle 7.5 g sodium cholate, 1402.5 g of DI water, 30 g of benzyl alcohol and 60 g of ethyl acetate, and mix on stir plate until dissolved.

For the formation of emulsion, a ratio of aqueous phase to oil phase is 5:1. The organic phase is poured into the aqueous solution and homogenized using IKA for 10 seconds at room temperature to form course emulsion. The solution is fed through the homogenizer (110S) at 9 Kpsi (45 psi on gauge) for 2 discreet passes to form nanoemulsion.

The emulsion is poured into quench (D.I. water) at <5° C. while stirring on stir plate. Ratio of quench to emulsion is 8:1.35% (w/w) Tween 80 is added in water to quench at ratio of 25:1 Tween 80 to drug. The nanoparticles are concentrated through TFF and the quench is concentrated on TFF with 500 kDa Pall cassette (2 membrane) to ~100 mL. Diafiltering is used using ~20 diavolumes (2 liters) of cold DI water, and the volume is brought down to minimal volume then collect final slurry, ~100 mL. The solids concentration of unfiltered final slurry is determined by the using tared 20 mL scintillation vial and adding 4 mL final slurry and dry under vacuum on lyo/oven and the weight of nanoparticles in the 4 mL of slurry dried down is determined. Concentrated sucrose (0.666 g/g) is added to final slurry sample to attain 10% sucrose.

Solids concentration of 0.45 um filtered final slurry was determined by filtering about 5 mL of final slurry sample before addition of sucrose through 0.45 μm syringe filter; to tared 20 mL scintillation vial add 4 mL of filtered sample and dry under vacuum on lyo/oven.

The remaining sample of unfiltered final slurry was frozen with sucrose. Vinorelbine Formulations:

| % Solids | In-vitro release conducted | Polymer Type: | % Vinorelbine Load (HPLC) | Particle Size (nm) |
|------|------|------|------|------|
| 5% | | 16-5 PLA-PEG | 4.27 | 143.3 |
| | | 16-5 PLA-PEG + PLA | 3.39 | 105.7 |
| 15% | | 16-5 PLA-PEG | 6.2 | 100.3 |
| | | 16-5 PLA-PEG + PLA | 15.95 | 141.3 |
| 30% | | 16-5 PLA-PEG (n = 3) | 10.41 | 90.8 |
| | | | 10.31 | 84.4 |
| | * | | 12.01 | 95 |
| | * | 16-5 PLA-PEG + PLA | 15.03 | 125.5 |
| | * | 16-5 PLGA-PEG + PLA | 14.66 | 120.3 |

* = in-vitro release done on samples

Figure 19:
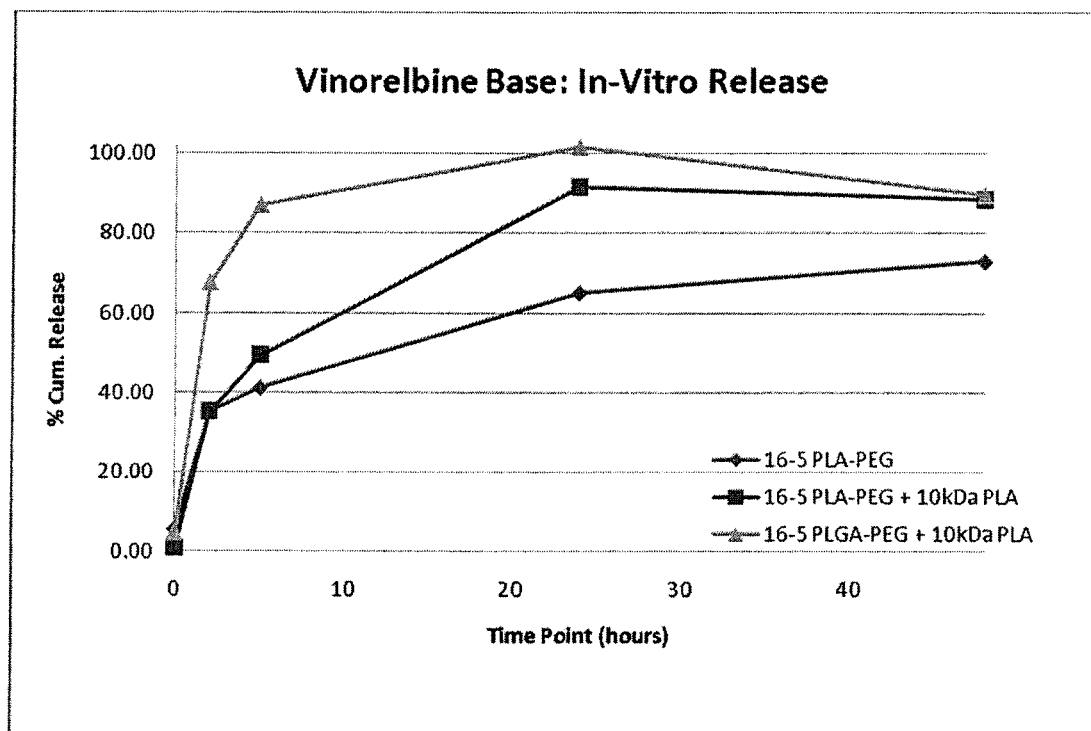
FIG. 19 depicts in vitro release properties of an exemplary disclosed nanoparticle that includes vinorelbine.

In-vitro release was conducted on three formulations at 30% totals solids: 16-5 PLA-PEG; 16-5 PLA-PEG+PLA; and 16-5 PLGA-PEG+PLA, and the in-vitro release data was collected at 37° C. in an air chamber using 10% urea in PBS solution as the release media. The table below and FIG. 19 depicts the results:

| Time Point (hours) | 16-5 PLA-PEG | 16-5 PLA-PEG + 10 kDa PLA | 16-5 PLGA-PEG + 10 kDa PLA |
|------|------|------|------|
| 0 | 5.62 | 0.84 | 4.79 |
| 2 | 35.29 | 35.35 | 67.63 |
| 5 | 41.28 | 49.58 | 87.05 |
| 24 | 65.20 | 91.81 | 101.62 |
| 48 | 73.02 | 88.63 | 89.57 |
| 144 | 81.08 | 84.98 | 91.46 |

Example 20

Vincristine

Nanoparticle formulations that include vincristine were prepared using the general procedure of Example 8.

Vincristine Formulations:

| Ref. No. | Components | Composition by Wt.(%) |
|---|---|---|
| 50-103-3-5 | mPEG(5k)-lPLA(16K)/Vincristine | 96/4 |
| 50-117-1-5 | mPEG(5k)-lPLA(16K)/Vincristine | 95/5 |
| 50-117-2-5 | mPEG(5k)-lPLA(16K)/Vincristine | 96/4 |
| 50-103-4 | mPEG(5k)-lPLA(16K)/lPLA(16K)/Vincristine | 46/46/8 |
| 50-103-2 | mPEG(5k)-lPLA(16K)/lPLA(16K)/Vincristine | 47/47/6 |

Analytical Characterisation of Vincristine Formulations:

| Ref. No. | Size (nm) | Drug Load (%) | Encapsulation Efficiency (%) |
|---|---|---|---|
| 50-103-3-5 | 103 | 4.4 | 21.8 |
| 50-117-1-5 | 110 | 4.6 | 22.8 |
| 50-117-2-5 | 115 | 4.2 | 20.8 |
| 50-103-4 | 146 | 8.3 | 41.6 |
| 50-103-2 | 98 | 6.0 | 30.0 |

Figure 20:
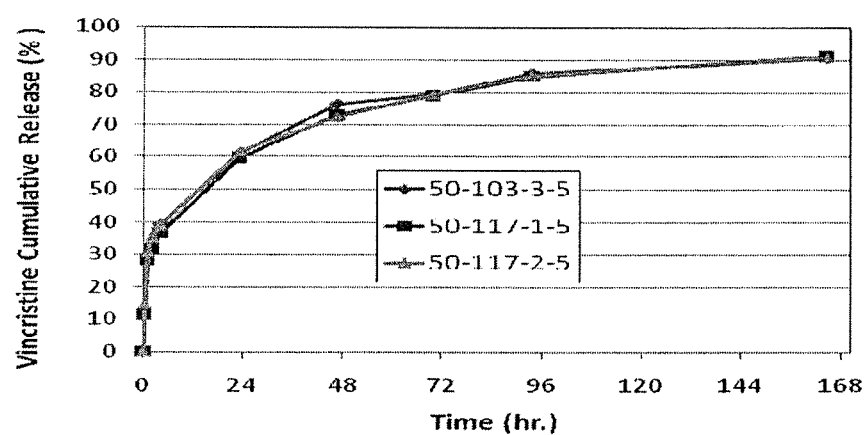
FIG. 20 depicts in vitro release properties of disclosed nanoparticles that include vincristine or docetaxel.

In vitro release was conducted on the vincristine formulations, and the in vitro release data was collected at 37° C. in an air chamber using 10% urea in PBS solution as the release media. FIG. 20 depicts in-vitro release for several of the lots referenced.

Example 21

Pharmacokinetics

The pharmacokinetics (PK) of nanoparticles having vincristine as prepared in Example 20 and having docetaxel as prepared in Example 8 were determined in Sprague-Dawley (SD) rats. Rats (male Sprague Dawley, approximately 300 g with jugular cannulae) were given a single intravenous dose of 0.5 mg/kg free drug or passively targeted nanoparticles encapsulating drug (10 wt % drug, 90 wt polymer (PLA-PEG, Mn PLA=16 Da; Mn PEG-5 Da, PTNP) with 5 mg/kg drug and PTNP at time=0. At various times after dosing, blood samples were collected from the jugular cannulae into tubes containing lithium heparin, and plasma was prepared. Plasma levels were determined by extraction of the drugs from plasma followed by LCMS analysis.

Figure 21:
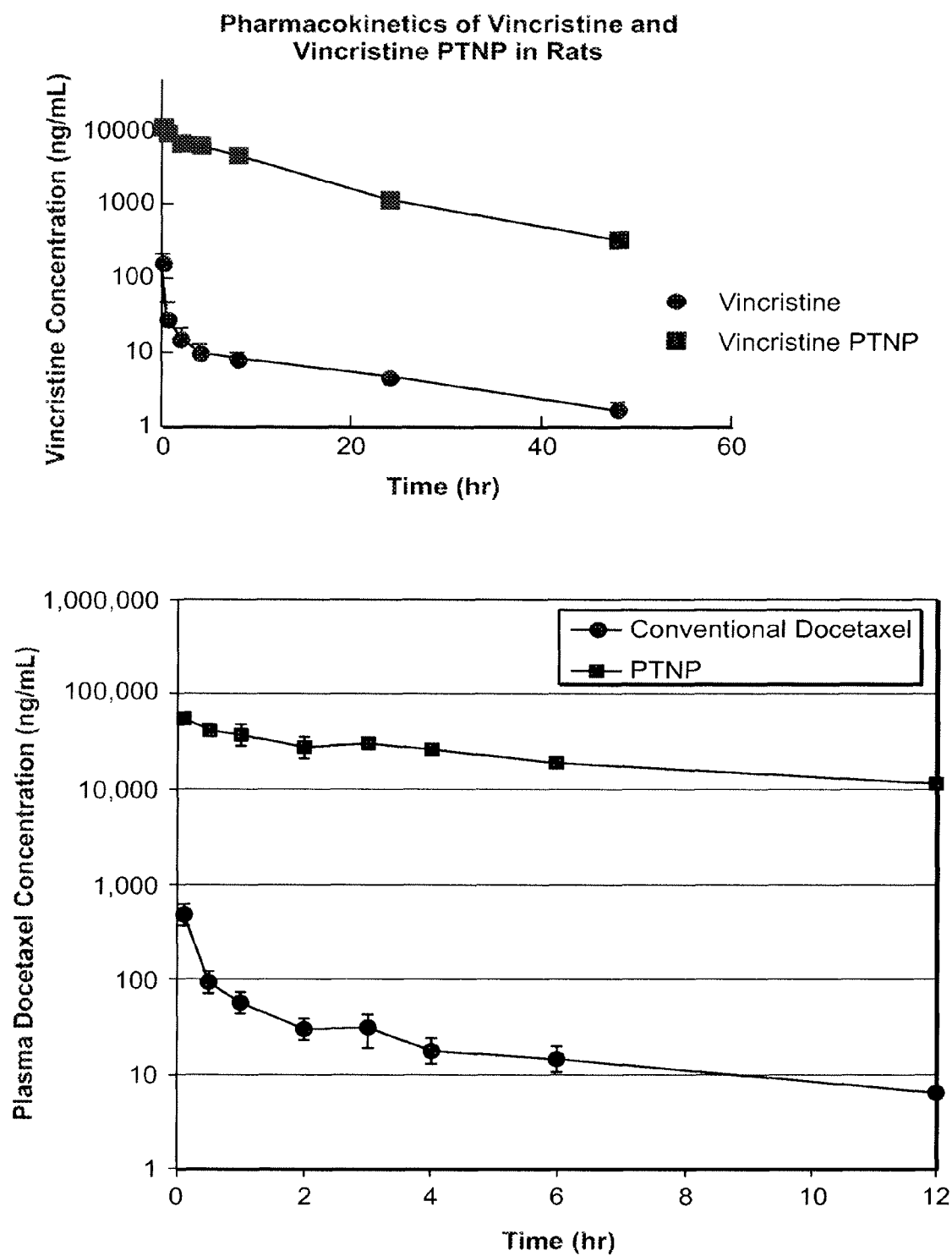
FIG. 21 depicts the pharmacokinetics of vincristine and vincristine PTNP in rats.

FIG. 21 depicts the PK profiles of vincristine and vincristine PTNP, and docetaxel and docetaxel PTNP.

Example 22

Particle Size Analysis

Particle size is analyzed by two techniques—dynamic light scattering (DLS) and laser diffraction. DLS is performed using a Brookhaven ZetaPals instrument at 25° C. in dilute aqueous suspension using a 660 nm laser scattered at 90° and analyzed using the Cumulants and NNLS methods (TP008). Laser diffraction is performed with a Horiba LS950 instrument in dilute aqueous suspension using both a HeNe laser at 633 nm and an LED at 405 nm, scattered at 90° and analyzed using the Mie optical model (TP009). The output from the DLS is associated with the hydrodynamic radius of the particles, which includes the PEG 'corona', while the laser diffraction instrument is more closely associated with the geometric size of the PLA particle 'core'.

Example 23

Ligand Density

Assuming an overall particle diameter is equivalent to the hydrodynamic diameter as measured by the Brookhaven particle sizer, nanoparticles are perfect spheres, and all of the hydrophilic PEG and ligand is expressed on the surface as well as that all of the PEG is fully hydrated, a model of the particle surface can be built, as shown in Table I:

TABLE I

Nanoparticle surface model for 100 nm particles of 16/5 co-polymer and 6.5 kDa homopolymer

| Ligand % | Polymer (molecules or SA/particle) | | | Ligand Coverage | | |
|---|---|---|---|---|---|---|
| mol % of co-polymer | Homo-polymer | Co-polymer | $nm^2$/PEG | mol/g NP | Molecules/particle | $nm^2$/ligand |
| 0% (NTNP) | 7050 | 2182 | 14.40 | 0 | 0 | NA |
| 1% GL2 | 7049 | 2183 | 14.39 | $1.72 \times 10^{-07}$ | 22 | 1439 |
| 5% GL2 | 7047 | 2187 | 14.37 | $8.63 \times 10^{-07}$ | 109 | 287 |
| 10% GL2 | 7043 | 2191 | 14.34 | $1.73 \times 10^{-07}$ | 219 | 143 |

Example 24

Breast Cancer Tumor Targeting

Figure 22:
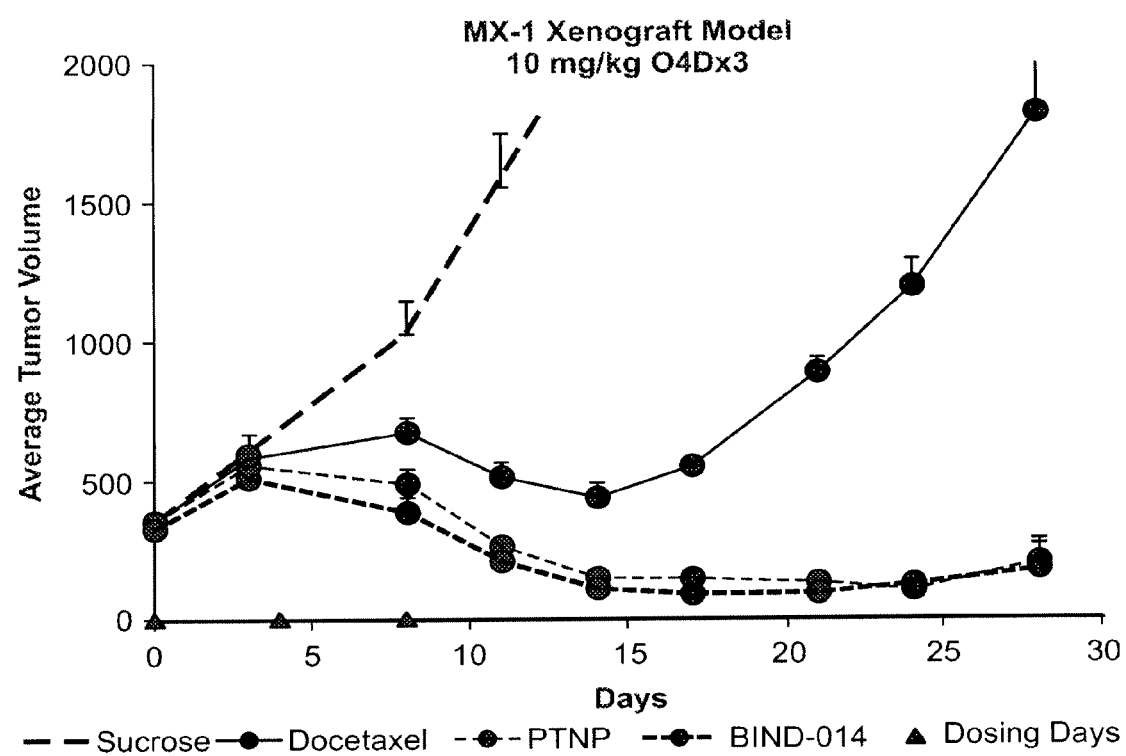
FIG. 22 depicts the average tumor volume after administration of disclosed nanoparticles that include docetaxel in a MX-1 xenograft mouse model of breast cancer.

The ability of intravenously administered nanoparticles prepared as in Example 8 (10 wt % docetaxel, 90 wt polymer (~1.25 wt % PLA-PEG-GL2; and ~98.75% PLA-PEG, Mn PLA=16 Da; Mn PEG=5 Da) (labeled as BIND-14) to inhibit non-prostate tumor growth was assessed in comparison to conventional docetaxel and non-targeted control particles having same drug/polymer composition (PTNP) in mice implanted with MX-1 xenografts. When tumors reached an average volume of 300 mm³, mice were administered test articles (sucrose, docetaxel, PTNP, BIND-14) every 4 days for 3 doses. Average tumor volumes over time for each treatment group is shown in FIG. 22.

Figure 23:
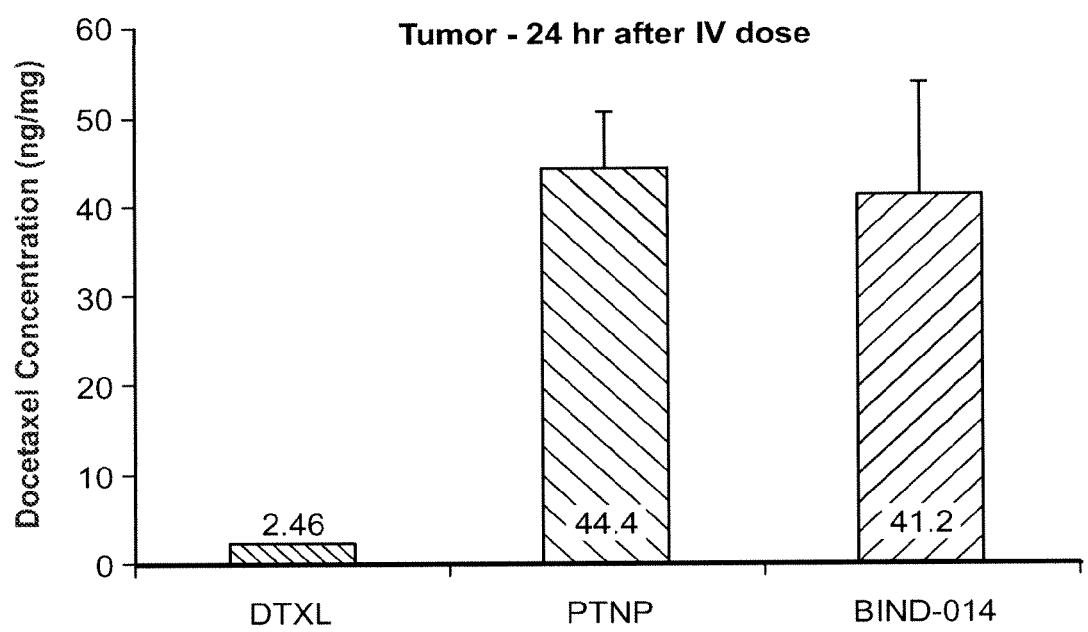
FIG. 23 depicts the docetaxel concentration in mouse tumors in a breast cancer MX-1 xenograft mouse model 24 hours after an intravenous dose of disclosed nanoparticles that include docetaxel.

The ability of targeted nanoparticles (BIND-14) to enhance the delivery of docetaxel to tumors after intravenous administration was assessed in mice bearing human MX-1 breast cancer xenografts, with an average tumor volume of 1700 mm³. The docetaxel concentrations(ng/mg) in tumors excised 24 hours after the IV dose from animals dosed with BIND-14, PTNP, and conventional docetaxel were analyzed for docetaxel content using LC/MS/MS and are presented in FIG. 23.

Example 24

Prostate Cancer Tumor Targeting

Nanoparticle delivery of docetaxel using nanoparticles prepared as in Example 8 (10 wt % docetaxel, 90 wt polymer (~1.25 wt % PLA-PEG-GL2; and ~98.75% PLA-PEG, Mn PLA=16 Da; Mn PEG=5 Da; BIND-14) to tumors after intravenous administration was assessed in male SCID mice bearing human LNCaP prostate cancer xenografts. Male SCID mice were subcutaneously inoculated with human LNCaP prostate cancer cells. Three to four weeks after inoculation, a single IV dose of 5 mg/kg docetaxel was administered as either BIND-014 or conventional docetaxel. Mice were sacrificed 2 h or 12 h post-dose. The tumors from each group were excised and assayed for docetaxel by an LC-MS method.

Figure 24:
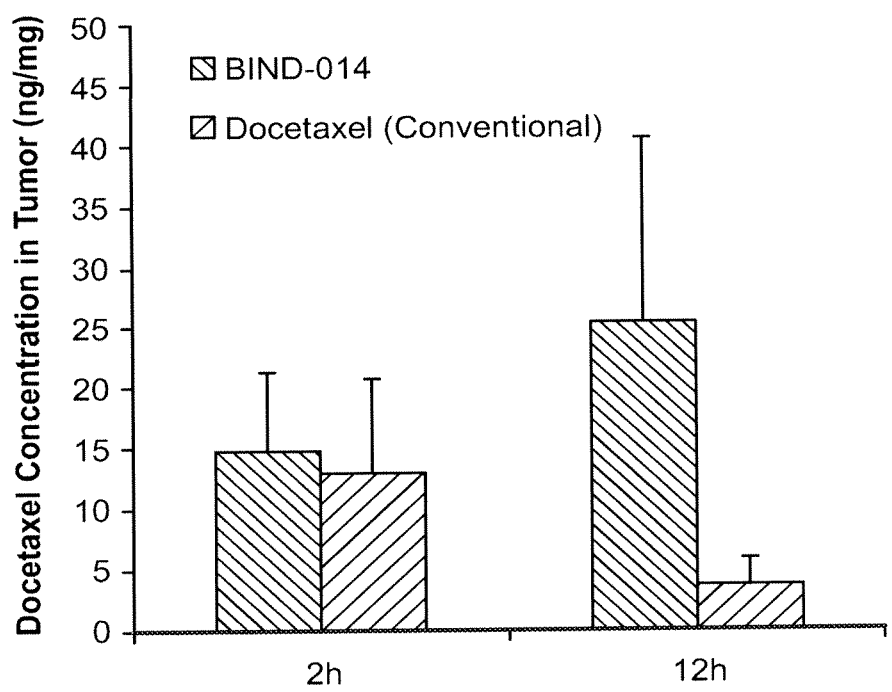
FIG. 24 depicts prostate tumor distribution of disclosed nanoparticles having docetaxel after administration to mice inoculated with human LNCaP prostate cancer cells.

Twelve hours after a single dose of 50 mg/kg of BIND-14, tumor docetaxelconcentration in animals receiving BIND-014 was approximately 7-times higher than in animals receiving conventional DTXL, indicating that long-circulating PSMA-targeted nanoparticles deliver more DTXL to the tumor site as shown in FIG. 24.

Figure 25:
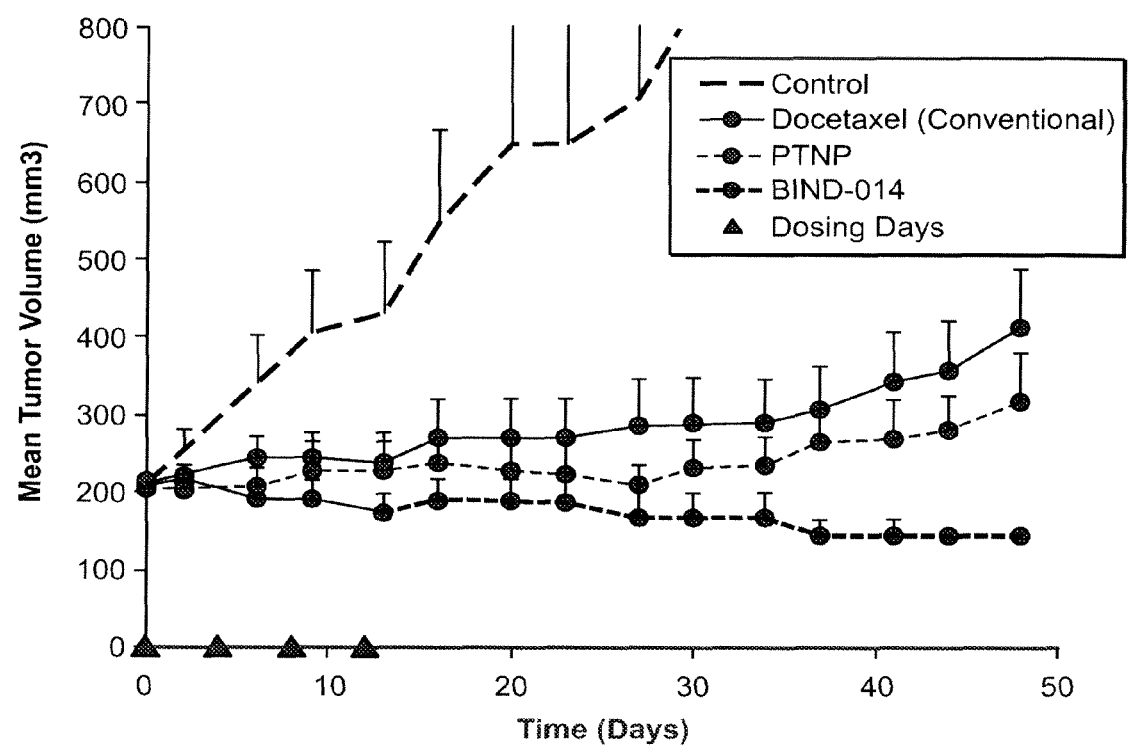
FIG. 25 shows tumor growth suppression in mice inoculated with human LNCaP prostate cancer cells after administration of disclosed nanoparticles with docetaxel.

The ability of repeat doses of BIND-014 to suppress tumor growth was also assessed in the LNCaP xenograft tumor model as shown in FIG. 25. Male SCID mice were subcutaneously inoculated with human LNCaP prostate cancer cells. Three to four weeks after inoculation, the mice were treated every other day for four doses with BIND-014, conventional docetaxel (DTXL), DTXL encapsulated in non-targeted nanoparticles (PTNP), and vehicle (Control). After four doses of 5 mg/kg, tumor volume reduction was greater in animals receiving BIND-014 compared to conventional docetaxel or non-targeted particles (PTNP). The increase in tumor docetaxel concentration results in a more pronounced cytotoxic effect.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A therapeutic nanoparticle comprising:
about 0.2 to about 35 weight percent of a therapeutic agent;
about 10 to about 99 weight percent of a diblock poly(lactic) acid-poly(ethylene)glycol copolymer, wherein said poly(lactic) acid-poly(ethylene)glycol copolymer comprises poly(lactic) acid having a number average molecular weight of about 15 to 20 kDa and poly(ethylene)glycol having a number average molecular weight of about 4 to about 6 kDa, or a diblock poly(lactic)-co-poly (glycolic) acid-poly(ethylene)glycol copolymer, wherein said poly(lactic)-co-poly (glycolic) acid-poly(ethylene)glycol copolymer comprises poly(lactic) -co-poly(glycolic) acid having a number average molecular weight of about 8 to about 12 kDa and poly(ethylene) glycol having a number average molecular weight of about 4 to about 6 kDa; and
about 1 to about 50 weight percent poly(lactic) acid or poly(lactic) acid-co-poly (glycolic) acid, and
wherein the therapeutic nanoparticle releases less than about 10% of the therapeutic agent over 24 hours when placed in a phosphate buffer solution at room temperature.

2. The therapeutic nanoparticle of claim 1 wherein said therapeutic agent is a taxane.

3. The therapeutic nanoparticle of claim 1, wherein the therapeutic agent is a vinca alkaloid.

4. The therapeutic nanoparticle of claim 3, wherein the therapeutic agent is vincristine or vinorelbine.

5. The therapeutic nanoparticle of claim 1, wherein said therapeutic agent is a mTOR inhibitor.

6. The therapeutic nanoparticle of claim 5, wherein the therapeutic agent is sirolimus, temsirolimus, or everolimus.

7. The therapeutic nanoparticle of claim 1, wherein the hydrodynamic diameter of therapeutic nanoparticle is about 60 to about 120 nm.

8. The therapeutic nanoparticle of claim 1, wherein the hydrodynamic diameter is about 70 to about 120 nm.

9. The therapeutic nanoparticle of claim 1, wherein the therapeutic nanoparticles substantially retains the therapeutic agent for at least 5 days at 25° C.

10. The therapeutic nanoparticle of claim 1, comprising about 10 to about 20 weight percent of a taxane agent.

11. The therapeutic nanoparticle of claim 1, comprising about 10 to about 20 weight percent of a vinca alkaloid.

12. The therapeutic nanoparticle of claim 1, comprising about 10 to about 20 weight percent of sirolimus.

13. The therapeutic nanoparticle of claim 1, comprising about 40 to about 90 weight percent poly(lactic) acid-poly (ethylene)glycol copolymer.

14. The therapeutic nanoparticle of claim 1, wherein the particle substantially immediately releases less than about 5% of the therapeutic agent over 1 hour when placed in a phosphate buffer solution at room temperature.

15. A pharmaceutical composition comprising:
a plurality of polymeric nanoparticles each comprising about 0.2 to about 35 weight percent of a therapeutic agent, about 70 to about 99 weight percent of a biocompatible polymer, and optionally a fatty alcohol; wherein the biocompatible polymer is selected from the group consisting of: a combination of poly(lactic) acid-poly (ethylene)glycol copolymer; and poly (lactic) acid or polylactic -co-glycolic acid copolymer;
wherein said poly(lactic) acid-poly(ethylene)glycol copolymer comprises poly(lactic) acid having a number average molecular weight of about 15 to 20 kDa and poly(ethylene)glycol having a number average molecular weight of about 4 to about 6 kDa; and
a pharmaceutically acceptable excipient, wherein the particle substantially immediately releases less than about 10% of the therapeutic agent over 24 hours when placed in a phosphate buffer solution at room temperature.

16. The pharmaceutical composition of claim 15, wherein the pharmaceutically acceptable excipient is sucrose.

17. The pharmaceutical composition of claim 15, wherein said nanoparticles substantially retains the therapeutic agent for at least 5 days at 25° C.

18. The pharmaceutical composition of claim 15, wherein the therapeutic agent is selected from docetaxel, vincristine, vinorelbine, sirolimus, and temsirolimus.

19. A method of treating prostate or breast cancer comprising administering to a patient in need thereof an effective amount of any of the therapeutic nanoparticles or compositions of claim 1.

20. A method of treating prostate or breast cancer, comprising administering to a patient in need thereof an effective amount of therapeutic nanoparticles comprising:
- about 0.2 to about 35 weight percent of docetaxel;
- about 30 to about 90 weight percent poly(lactic) acid-poly(ethylene)glycol copolymer, wherein said poly(lactic) acid-poly(ethylene)glycol copolymer comprises poly(lactic) acid having a number average molecular weight of about 15 to 20 kDa and poly(ethylene)glycol having a number average molecular weight of about 4 to about 6 kDa, or poly(lactic)-co-poly (glycolic) acid-poly (ethylene)glycol copolymer, wherein said poly(lactic)-co-poly (glycolic) acid-poly (ethylene)glycol copolymer comprises poly(lactic) -co-poly(glycolic) acid having a number average molecular weight of about 8 to about 12 kDa and poly(ethylene)glycol having a number average molecular weight of about 4 to about 6 kDa; and
- about 5 to about 75 weight percent poly(lactic) acid or poly(lactic) acid-co-poly (glycolic) acid, wherein the therapeutic nanoparticles release less than about 10% of the therapeutic agent over 24 hours when placed in a phosphate buffer solution at room temperature.

* * * * *